US011478518B2

(12) United States Patent
Thorne

(10) Patent No.: US 11,478,518 B2
(45) Date of Patent: Oct. 25, 2022

(54) IMMUNO-ONCOLYTIC THERAPIES

(71) Applicant: UNIVERSITY OF PITTSBURGH-OF THE COMMONWEALTH SYSTEM OF HIGHER EDUCATION, Pittsburgh, PA (US)

(72) Inventor: Stephen Howard Thorne, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 15/048,698

(22) Filed: Feb. 19, 2016

(65) Prior Publication Data
US 2016/0235793 A1 Aug. 18, 2016

Related U.S. Application Data

(63) Continuation of application No. PCT/US2014/052308, filed on Aug. 22, 2014.

(60) Provisional application No. 61/868,978, filed on Aug. 22, 2013.

(51) Int. Cl.
*A61K 35/768* (2015.01)
*A61K 45/06* (2006.01)
*C12N 7/00* (2006.01)
*A61K 39/00* (2006.01)

(52) U.S. Cl.
CPC ............ *A61K 35/768* (2013.01); *A61K 45/06* (2013.01); *C12N 7/00* (2013.01); *A61K 2039/572* (2013.01); *A61K 2039/575* (2013.01); *A61K 2039/585* (2013.01); *C12N 2710/24121* (2013.01); *C12N 2710/24122* (2013.01); *C12N 2710/24132* (2013.01); *C12N 2710/24171* (2013.01)

(58) Field of Classification Search
CPC ........ C12N 7/00; A61K 45/06; A61K 35/768; A61K 39/12
See application file for complete search history.

(56) References Cited

U.S. PATENT DOCUMENTS

| | | | |
|---|---|---|---|
| 2011/0038843 A1* | 2/2011 | Kusmartsev | A61K 48/005 424/93.71 |
| 2012/0276053 A1* | 11/2012 | Kirn | A61K 38/193 424/93.2 |
| 2013/0183271 A1 | 7/2013 | Kirn et al. | |
| 2013/0202639 A1 | 8/2013 | Kousoulas et al. | |
| 2015/0250837 A1* | 9/2015 | Nolin | C07K 16/2818 424/281.1 |

FOREIGN PATENT DOCUMENTS

| | | |
|---|---|---|
| AU | 2012/244210 A1 | 11/2012 |
| EP | 2269618 A1 | 1/2011 |
| JP | 2009-507853 A | 2/2009 |
| JP | 2010-521497 A | 6/2010 |
| JP | 4796299 B2 | 10/2011 |
| JP | 2013-504601 A | 2/2013 |
| JP | 2016-527920 A | 9/2016 |
| JP | 6912199 B2 | 8/2021 |
| JP | 7021154 B2 | 2/2022 |
| WO | WO 2004/014314 A2 | 2/2004 |
| WO | WO 2007/023725 A1 | 3/2007 |
| WO | WO 2007/030668 A2 | 3/2007 |
| WO | WO 2008/113078 A1 | 9/2008 |
| WO | WO 2011/032180 A1 | 3/2011 |
| WO | WO 2011/119925 A2 | 9/2011 |
| WO | WO 2012/142529 A2 | 10/2012 |
| WO | WO 2015/027163 A1 | 2/2015 |

OTHER PUBLICATIONS

Kaliberova et al 2009, Mol Cancer Ther 8:3130-3139.*
Wan et al 2010, Veterinary Immunology and Immunopathology 137:47-53.*
Weintraub et al (1977, Virology 78:315-322.*
Getachew , Ph. D. Thesis, 2011, Abstract.*
Lee et al., Cancer Gene Therapy, 2010, 17: 73-79.*
Takeshita et al. J. Virol., 2006, 80: 6218-6224.*
Perdiguero et al., J. Interferon & Cytokine Res., 2009, 9: 581-598.*
Kelly et al., Mol. Ther., 2007, 15: 651-659.*
Zhang, Cancer Res., 2007, 67: 10038-10046.*
Rojas et al., Theranostics, 2012, 2: 363-373.*
Shah, J. Neuro-Oncol., 2003, 65: 203-226.*
Hawkins, Lancet Oncology, 2002, 3: 17-26.*
Hermiston, Cancer Gene Therapy, 2002, 9: 1022-1035.*
McGee, Br. J. Anaesthesia, 2002, 88: 130-140.*
Thorne, Current Gene Therapy, 2005, 5: 429-443.*
Hu, Clin. Cancer Res., 2006, 12: 6737-6747.*
Langenmayer, Biologicals, 2018, 54:58-62.*
Kalinsky, J. Immunol., 2012, 188: 21-28.*
Ahmadi, Cancer Res., 2008, 68: 7520-7529.*
Yu, Mol. Cancer Ther., 2009, 8: 141-151.*

(Continued)

*Primary Examiner* — Ileana Popa
(74) *Attorney, Agent, or Firm* — Baker Botts L.L.P.

(57) ABSTRACT

The present invention relates to oncolytic vaccinia viruses which have been modified to promote anti-tumor immunity and/or reduce host immunity and/or antibody response against the virus. It is based, at least in part, on the discovery that oncolytic vaccinia virus (i) bearing a genome deletion of a gene that reduces T cell immunity (interleukin-18 binding protein); (ii) treated with a sialidase enzyme which is believed to reduce TLR2 activation and therefore the antibody response; (iii) carrying a gene that enhances cytotoxic T lymphocyte induction (e.g., TRIF) and/or (iv) reduces tumor myeloid-derived suppressor cells by reducing prostaglandin E2 reduces tumor growth. Accordingly, the present invention provides for immunooncolytic vaccinia viruses and methods of using them in the treatment of cancers.

24 Claims, 62 Drawing Sheets

(56) References Cited

OTHER PUBLICATIONS

Figure 1A:
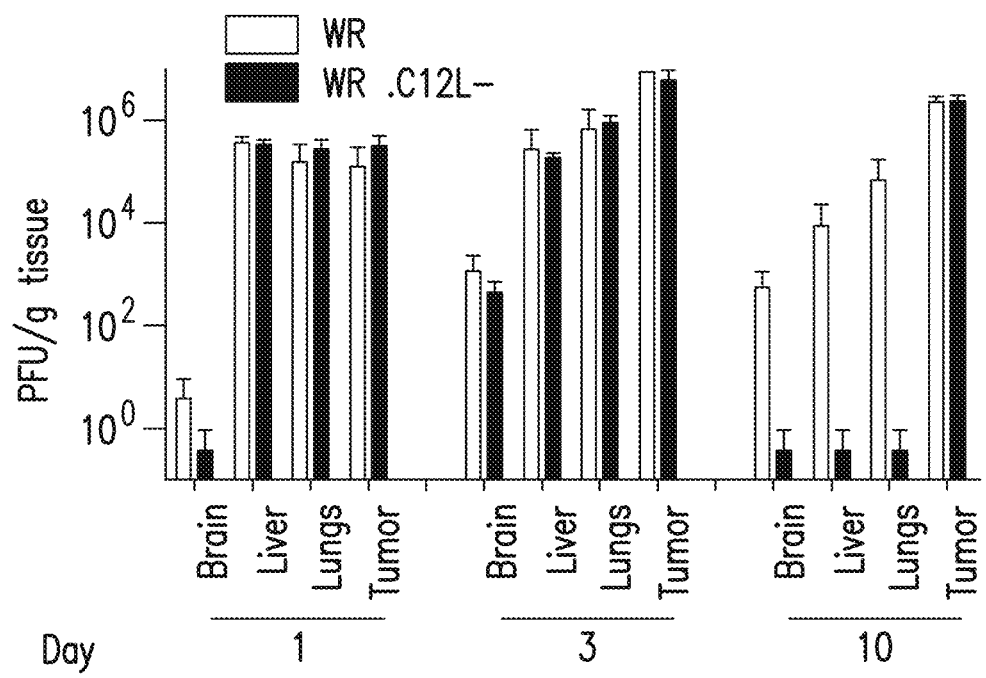

Arai, Yonago Acta Medica, 2012, 55: 1-9.*
Khuri, Nat. Med., 2000, 6: 879-885.*
Alvarez-Breckenridge et al., "NK cells impede glioblastoma virotherapy through NKp30 and NKp46 natural cytotoxicity receptors," Nature Medicine 18(12):1827-1834 (2012).
Bahar et al., "Structure and Function of A41, a Vaccinia Virus Chemokine Binding Protein," PLoS Pathog 4(1):e5:0055-0068 (2008).
Banaszynski et al., "Chemical control of protein stability and function in living animals," Nat Med 14(10):1123-1127 (2008).
Banchereau et al., "Dendritic cells as therapeutic vaccines against cancer," Nat Rev Immunol 5:296-306 (2005).
Belyakov et al., "What Role Does the Route of Immunization Play in the Generation of Protective Immunity Against Mucosal Pathogens?", Journal of Immunology 183:6883-6892 (2009).
Bernard et al., "Chronic Inhibition of Cyclooxygenase-2 Attenuates Antibody Responses against Vaccinia Infection," Vaccine 28(5):1363-1372 (2010).
Bischoff et al., "An adenovirus mutant that replicates selectively in p53-deficient human tumor cells," Science 274:373-376 (1996).
Brader et al., "Imaging of Lymph Node Micrometastases Using an Oncolytic Herpes Virus and [18F]FEAU PET," PLoS One 4(3):e4789 (2009).
Breitbach et al., "Intravenous delivery of a multi-mechanistic cancer-targeted oncolytic poxvirus in humans," Nature 477:99-102 (2011).
Buller et al., "Poxvirus pathogenesis," Microbiological Reviews 55(1):80-122 (1991).
Chang et al., "Treatment with Cyclooxygenase-2 Inhibitors Enables Repeated Administration of Vaccinia Virus for Control of Ovarian Cancer," Molecular Therapy 17(8):1365-1372 (2009).
Charafe-Jauffret et al., "Breast Cancer Cell Lines Contain Functional Cancer Stem Cells with Metastatic Capacity and a Distinct Molecular Signature," Cancer Research 69(4):1302-1313 (2009).
Chen et al., "Cancers take their Toll—the function and regulation of Toll-like receptors in cancer cells," Oncogene 27:225-233 (2008).
Chen et al., "Regulating Cytokine Function Enhances Safety and Activity of Genetic Cancer Therapies," Molecular Therapy 21(1):167-174 (2013).
Cheng et al., "Anticancer Function of Polyinosinic-Polycytidylic Acid," Cancer Biology & Therapy 10(12):1219-1223 (2010).
Cho et al., "Isolation and Molecular Characterization of Cancer Stem Cells in MMTV-Wnt-1 Murine Breast Tumors," Stem Cells 26:364-371 (2008).
Contag et al., "Definition of an enhanced immune cell therapy in mice that can target stem-like lymphoma cells," Cancer Research 70(23):9837-45 (2010).
Eisenberg et al., "Real-Time Intraoperative Detection of Breast Cancer Axillary Lymph Node Metastases Using a Green Fluorescent Protein-Expressing Herpes Virus," Annals of Surgery 243:824-832; discussion 830-832 (2006).
Enzler et al., "Deficiencies of GM-CSF and Interferon gamma link inflammation and cancer," The Journal of Experimental Medicine 197(9):1213-1219 (2003).
Ercolini et al., "Recruitment of latent pools of high-avidity CD8(+) T cells to the antitumor immune response," The Journal of Experimental Medicine 201(10):1591-1602 (2005).
Errington et al., "Fusogenic membrane glycoprotein-mediated tumour cell fusion activates human dendritic cells for enhanced IL-12 production and T-cell priming," Gene Ther 13:138-149 (2006).
Falivene et al., "Improving the MVA vaccine potential by deleting the viral gene coding for the IL-18 binding protein," PLoS One 7(2):e32220 (2012).
Feoktistova et al., "cIAPs Block Ripoptosome Formation, a RIP1/caspase-8 Containing Intracellular Cell Death Complex Differentially Regulated by cFLIP Isoforms," Molecular Cell 43:449-463 (2011).
Filipazzi et al., "Identification of a New Subset of Myeloid Suppressor Cells in Peripheral Blood of Melanoma Patients With Modulation by a Granulocyte-Macrophage Colony-Stimulation Factor-Based Antitumor Vaccine," Journal of Clinical Oncology 25(18):2546-2553 (2007).
Fujita et al., "COX-2 blockade suppresses gliomagenesis by inhibiting myeloid-derived suppressor cells," Cancer Research 71(7):2664-2674 (2011).
Fukata et al., "Role of Toll-like receptors in gastrointestinal malignancies," Oncogene 27:234-243 (2008).
Galon et al., "Type, Density, and Location of Immune Cells Within Human Colorectal Tumors Predict Clinical Outcome," Science 313:1960-1964 (2006).
Garber, "China approves world's first oncolytic virus therapy for cancer treatment," J Natl Cancer Inst 98(5):298-300 (2006).
Ginestier et al., "CXCR1 blockade selectively targets human breast cancer stem cells in vitro and in xenografts," The Journal of Clinical Investigation 120(2):485-497 (2010).
Gnant et al., "Tumor-specific gene delivery using recombinant vaccinia virus in a rabbit model of liver metastases," J Natl Cancer Inst 91(20):1744-1750 (1999).
Godin-Ethier et al., "Indoleamine 2,3-Dioxygenase Expression in Human Cancers: Clinical And Immunologic Perspectives," Clinical Cancer Research 17(22):6985-6991 (2011).
Green et al., "Immunogenic and Tolerogenic Cell Death," Nature Reviews Immunology 9(5):353-363 (2009).
Gulley et al., "A Pilot Study to Evaluate the Safety and Clinical Outcomes of Vaccination with Recombinant CEA-MUC-1-TRICOM (PANVAC) Poxviral-based Vaccines in Patients with Metastatic Carcinoma," Clin Cancer Res 14(10):3060-3069 (2008).
Guo et al., "The Enhanced Tumor Selectivity of an Oncolytic Vaccinia Lacking the Host Range and Antiapoptosis Genes SPI-1 and SPI-2," Cancer Res 65(21):9991-9998 (2005).
Guo et al., "Oncolytic Virotherapy: Molecular Targets in Tumor-Selective Replication and Carrier Cell-Mediated Delivery of Oncolytic Viruses," Biochim Biophys Acta 1785(2):217-231 (2008).
Guy et al., "Expression of the neu protooncogene in the mammary epithelium of transgenic mice induces metastatic disease," Proc. Natl. Acad. Sci. USA 89:10578-10582 (1992).
Hennessy et al., "Targeting Toll-like receptors: Emerging therapeutics?", Nature Reviews Drug Discovery 9:293-307 (2010).
Hokey et al., "Tumor cell loaded type-I polarized dendritic cells induce Th1-Mediated Tumor Immunity," Cancer Research 65(21):10059-10067 (2005).
International Search Report and Written Opinion dated Nov. 7, 2014 in International Application No. PCT/US2014/052308.
Iwasaki et al., "Enhanced CTL responses mediated by plasmid DNA immunogens encoding costimulatory molecules and cytokines," Journal of Immunology 158:4591-4601 (1997).
Jiang et al., "Toll-like receptor 3-mediated activation of NF-kB and IRF3 diverges at Toll-IL-1 receptor domain-containing adapter inducing IFN-β," PNAS 101(10):3533-3538 (2004).
Jinushi et al., "MFG-E8-mediated uptake of apoptotic cells by APCs links the pro- and antiinflammatory activities of GM-CSF," The Journal of Clinical Investigation 117(7):1902-1913 (2007).
Jones et al., "Therapeutic strategies for the clinical blockade of IL-6/gp130 signaling," The Journal of Clinical Investigation 121(9):3375-3383 (2011).
Kalinski et al., "Polarized dendritic cells as cancer vaccines: directing effector-type T cells to tumors," Semin Immunol. 22(3):173-182 (2010).
Kalinski et al., "T-cell priming by type-1 and type-2 polarized dendritic cells: the concept of a third signal," Immunol Today 20(12):561-7 (1999).
Kalinski, "Regulation of Immune Responses by Prostaglandin E2," Journal of Immunology 188:21-28 (2012).
Kelly et al., "Real-time intraoperative detection of melanoma lymph node metastases using recombinant vaccinia virus GLV-1h68 in an immunocompetent animal model," International Journal of Cancer 124(4):911-918 (2009).
Khuri, "A controlled trial of intratumoral Onyx-015, a selectively replicating adenovirus, in combination with cisplatin and 5-fluorouracil in patients with recurrent head and neck cancer," Nature Medicine 6(8):879-885 (2000).

(56) References Cited

OTHER PUBLICATIONS

Kim et al., "Systemic Armed Oncolytic and Immunologic Therapy for Cancer with JX-594, a Targeted Poxvirus Expressing GM-CSF," Mol Ther 14(3):361-70 (2006).
Kim et al., "Antibody association with HER-2/neu-targeted vaccine enhances CD8+ T cell responses in mice through Fc-mediated activation of DCs," The Journal of Clinical Investigation 118(5):1700-1711 (2008).
Kim et al., "Oncolytic and immunotherapeutic vaccinia induces antibody-mediated complement-dependent cancer cell lysis in humans," Science Translational Medicine 5(185):185ra63 (2013).
Kirn et al., "Replication-selective virotherapy for cancer: Biological principles, risk management and future directions," Nat Med 7(7):781-787 (2001).
Kirn et al., "Targeting of interferon-beta to produce a specific, multi-mechanistic oncolytic vaccinia virus," PLoS Med 4(12):e353:2001-2012 (2007).
Kirn et al., "Enhancing poxvirus oncolytic effects through increased spread and immune evasion," Cancer Res 68(7):2071-2075 (2008).
Kirn et al., "Targeted and armed oncolytic poxviruses: a novel multi-mechanistic therapeutic class for cancer," Nat Rev Cancer 9:64-71 (2009).
Laporte, "Enhancing the oncolytic efficacy of vaccinia virus by mutagenic augmentation of EEV production," MSc Thesis, 2012, University of Ottawa, Ontario, Canada.
Le et al., "CD8(+) Foxp3(+) tumor infiltrating lymphocytes accumulate in the context of an effective anti-tumor response," International Journal of Cancer 129(3):636-647 (2011).
Lemoine et al., "Massive expansion of regulatory T-cells following interleukin 2 treatment during a phase I-II dendritic cell-based immunotherapy of metastatic renal cancer," International Journal Of Oncology 35:569-581 (2009).
Li et al., "Chemokine expression from oncolytic vaccinia virus enhances vaccine therapies of cancer," Molecular Therapy 19:650-657 (2011).
Liu et al., "The targeted oncolytic poxvirus JX-594 demonstrates antitumoral, antivascular, and anti-HBV activities in patients with hepatocellular carcinoma," Mol Ther 16(9):1637-1642 (2008).
Longhi et al., "Dendritic cells require a systemic type I interferon response to mature and induce CD4+ Th1 immunity with poly IC as adjuvant," The Journal of Experimental Medicine 206(7):1589-1602 (2009).
Mailliard et al., "α-type-1 polarized dendritic cells: a novel immunization tool with optimized CTL-inducing activity," Cancer Res 64:5934-5937 (2004).
McCart et al. "Systemic Cancer Therapy with a Tumor-selective Vaccinia Virus Mutant Lacking Thymidine Kinase and Vaccinia Growth Factor Genes," Cancer Res 61:8751-8757 (2001).
Nestle et al., "Cancer vaccines: the next generation of tools to monitor the anticancer immune response," PLoS Med 2(10):e339:951-952 (2005).
Ning et al., "Cancer Stem Cell Vaccination Confers Significant Antitumor Immunity," Cancer Research 72(7):1853-1864 (2012).
O'Gorman et al., "Alternate mechanisms of initial pattern recognition drive differential immune responses to related poxviruses," Cell Host Microbe 8(2):174-185 (2010).
Okada et al., "Induction of CD8+ T-cell Responses Against Novel Glioma-Associated Antigen Peptides and Clinical Activity by Vaccinations With α-Type I Polarized Dendritic Cells and Polyinosinic-Polycytidylic Acid Stabilized by Lysine and Carboxymethylcellulose in Patients with Recurrent Malignant Glioma," Journal Of Clinical Oncology 29(3):330-336 (2011).
Okamura et al., "Cloning of a new cytokine that induces IFN-gamma production by T cells," Nature 378:88-91 (1995).
O'Neill et al., "Therapeutic Targeting of Toll-Like Receptors for Infectious and Inflammatory Diseases and Cancer," Pharmacological Reviews 61:177-197 (2009).
Parato et al., "The Oncolytic Poxvirus JX-594 Selectively Replicates in and Destroys Cancer Cells Driven by Genetic Pathways Commonly Activated in Cancers," Molecular Therapy 20(4):749-758 (2012).
Park et al., "Use of a targeted oncolytic poxvirus, JX-594, in patients with refractory primary or metastatic liver cancer: a phase I trial," Lancet Oncol 9:533-42 (2008).
Prestwich et al., "Immune-mediated antitumor activity of reovirus is required for therapy and is independent of direct viral oncolysis and replication," Clin Cancer Res 15(13):4374-4381 (2009).
Prestwich et al., "Tumor infection by oncolytic reovirus primes adaptive antitumor immunity," Clinical Cancer Research 14(22):7358-7366 (2008).
Puhlmann et al., "Vaccinia as a vector for tumor-directed gene therapy: biodistribution of a thymidine kinase-deleted mutant," Cancer Gene Ther 7:66-73 (2000).
Pulido et al., "Using virally expressed melanoma cDNA libraries to identify tumor-associated antigens that cure melanoma," Nature Biotechnology 30(4):337-343 (2012).
Pütz et al., "Quantification of antibody responses against multiple antigens of the two infectious forms of Vaccinia virus provides a benchmark for smallpox vaccination," Nat Med 12(11):1310-5 (2006).
Rakoff-Nahoum et al., "Toll-like receptors and cancer," Nature Reviews Cancer 9:57-63 (2009).
Reading et al., "Vaccinia virus interleukin-18-binding protein promotes virulence by reducing gamma interferon production and natural killer and T-cell activity," J Virol 77(18):9960-9968 (2003).
Rommelfanger et al., "Systemic Combination Virotherapy for Melanoma with Tumor Antigen-Expressing Vesicular Stomatitis Virus and Adoptive T-Cell Transfer," Cancer Research 72(18):4753-4764 (2012).
Rosenberg et al., "Cancer immunotherapy: moving beyond current vaccines," Nat Med 10(9):909-915 (2004).
Samuelsson et al., "Survival of lethal poxvirus infection in mice depends on TLR9, and therapeutic vaccination provides protection," J Clin Invest 118(5):1776-1784 (2008).
Sasaki et al., "Regulation of DNA-Raised Immune Responses by Cotransfected Interferon Regulatory Factors," Journal of Virology 76(13):6652-6659 (2002).
Sato et al., "Toll/IL-1 Receptor Domain-Containing Adaptor Inducing IFN-β (TRIF) Associates with TNF Receptor-Associated Factor 6 and TANK-Binding Kinase 1, and Activates Two Distinct Transcription Factors, NF-kB and IFN-Regulatory Factor-3, in the Toll-Like Receptor Signaling," Journal of Immunology 171:4304-4310 (2003).
Sautès-Fridman et al. "Tumor microenvironment is multifaceted," Cancer Metastasis Reviews 30:13-25 (2011).
Schmidt, "Amgen spikes interest in live virus vaccines for hard-to-treat cancers," Nature Biotechnology 29(4):295-6 (2011).
Senzer et al., "Phase II clinical trial of a granulocyte-macrophage colony-stimulating factor-encoding, second-generation oncolytic herpes virus in patients with unresectable metastatic melanoma," J Clin Oncol 27(34):5763-5771 (2009).
Setoguchi et al., "Homeostatic maintenance of natural Foxp3(+) CD25(+) CD4(+) regulatory T cells by interleukin (IL)-2 and induction of autoimmune disease by IL-2 neutralization," The Journal of Experimental Medicine 201(5):723-735 (2005).
Silva et al., "Aldehyde Dehydrogenase in Combination with CD 133 Defines Angiogenic Ovarian Cancer Stem Cells That Portend Poor Patient Survival," Cancer Research 71(11):3991-4001 (2011).
Smith et al., "Vaccinia Virus Immune Evasion: Mechanisms, Virulence And Immunogenicity," Journal of General Virology 94:2367-2392 (2013).
Smith et al., "Infectious poxvirus vectors have capacity for at least 25000 base pairs of foreign DNA," Gene 25:21-28 (1983).
Smith et al., "Immune modulation by proteins secreted from cells infected by vaccinia virus," Arch Virol Suppl 15:111-29 (1999).
Symons et al., "The vaccinia virus C12L protein inhibits mouse IL-18 and promotes virus virulence in the murine intranasal model," J Gen Virol 83:2833-2844 (2002).

(56) References Cited

OTHER PUBLICATIONS

Symons et al., "Vaccinia Virus Encodes a Soluble Type I Interferon Receptor of Novel Structure and Broad Species Specificity," Cell 81:551-60 (1995).
Takeshita et al., "Toll-Like Receptor Adaptor Molecules Enhance DNA-Raised Adaptive Immune Responses against Influenza and Tumors through Activation of Innate Immunity," Journal of Virology 80(13):6218-6224 (2006).
Terajima et al., "Role of Indoleamine 2,3-Dioxygenase in Antiviral Activity of Interferon-gamma Against Vaccinia Virus," Viral Immunology 18(4):722-729 (2005).
Thorne et al., "Immunotherapeutic potential of oncolytic vaccinia virus," Frontiers in Oncology: Tumor Immunity 4(155):1-5 (2014).
Thorne, "Enhancing biological therapy through conditional regulation of protein stability," Expert Reviews in Molecular Medicine 12:e2 (2010).
Thorne et al., "Rational strain selection and engineering creates a broad-spectrum, systemically effective oncolytic poxvirus, JX-963," J Clin Invest 117(11):3350-3358 (2007).
Thorne et al., "Targeting Localized Immune Suppression Within the Tumor Through Repeat Cycles of Immune Cell-Oncolytic Virus Combination Therapy," Molecular Therapy 18(9):1698-1705 (2010).
Trumpfheller et al., "The microbial mimic poly IC induces durable and protective CD4+ T cell immunity together with a dendritic cell targeted vaccine," PNAS 105(7):2574-2579 (2008).
Tsukamoto et al., "Expression of the int-1 Gene in Transgenic Mice Is Associated with Mammary Gland Hyperplasia and Adenocarcinomas in Male and Female Mice," Cell 55:619-625 (1988).
Umemura et al., "Defective NF-kB signaling in metastatic head and neck cancer cells leads to enhanced apoptosis by dsRNA," Cancer Research 72(1):45-55 (2012).
Vella et al., "Healthy individuals have T-cell and antibody responses to the tumor antigen cyclin B1 that when elicited in mice protect from cancer," PNAS 106(33):14010-14015 (2009).
Visus et al., "Targeting ALDH(bright) human carcinoma initiating cells with ALDH1A1-specific CD8(+) T cells," Clinical Cancer Research 17(19):6174-6184 (2011).
Wang et al., "Treating Tumors With a Vaccinia Virus Expressing IFNβ Illustrates the Complex Relationships Between Oncolytic Ability and Immunogenicity," Molecular Therapy 20(4):736-748 (2012).
Wei et al., "Interleukin-2 Administration Alters the CD4+FOXP3+ T-Cell Pool and Tumor Trafficking in Patients with Ovarian Carcinoma," Cancer Research 67(15):7487-7494 (2007).
Weiss et al., "Trafficking of High Avidity HER-2/neu-Specific T cells into HER-2/neu-Expressing Tumors after Depletion of Effector/Memory-Like Regulatory T Cells," PLoS One 7(2):e31962 (2012).
Wesa et al., "Polarized Type-1 Dendritic Cells (DC1) Producing High Levels of IL-12 Family Members Rescue Patient TH1-type Antimelanoma CD4+ T Cell Responses In Vitro," J Immunother 30(1):75-82 (2007).
Wong et al., "Helper Activity of NK Cells During the Dendritic Cell mediated Induction of Melanoma-specific Cytotoxic T Cells," Journal of Immunotherapy 34(3):270-278 (2011).
Worschech et al., "Systemic treatment of xenografts with vaccinia virus GLV-Ih68 reveals the immunologic facet of oncolytic therapy," BMC Genomics 10:301 (2009).

Yang et al., "Persistent Toll-like receptor signals are required for reversal of regulatory T cell-mediated CD8 tolerance," Nature Immunology 5(5):508-515 (2004).
Yu et al., "Visualization of tumors and metastases in live animals with bacteria and vaccinia virus encoding light-emitting proteins," Nat Biotechnol 22(3):313-20 (2004).
Zhang et al., "Eradication of solid human breast tumors in nude mice with an intravenously injected light-emitting oncolytic vaccinia virus," Cancer Res 67(20):10038-1046 (2007).
Zhu et al., "High-throughput screening for TLR3-IRF3 signaling pathway modulators identifies several antipsychotic drugs as TLR inhibitors," Journal of Immunology 184(10):5768-5776 (2010).
Zhu et al., "Innate immunity against vaccinia virus is mediated by TLR2 and requires TLR-independent production of IFN-β," Blood 109(2):619-625 (2007).
Weintraub et al., "Biogenesis of Vaccinia. Effects of Inhibitors of Glycosylation on Virus-Mediated Activities," Virology 78:315-322 (1977).
Rojas et al., "Manipulating TLR Signaling Increases the Anti-tumor T Cell Response Induced by Viral Cancer Therapies," Cell Reports 15:264-273 (2016).
Supplementary Partial European Search Report dated Mar. 21, 2017 in EP Application No. 14837931.
Baoquan Zhu, Biopharmaceutical Technology, Chemical Industry Press, p. 55-56, Jun. 2004 [with English translation].
Jun Dou, Tumor Stem Cells, Southeast University Press, p. 142, 2009 [with English translation].
Tasuwaki et al., "Significance of 15-Hydroxyprostaglandin Dehydrogenase in Gastric Cancer," Prog. Med., 30:791-796 (2010) [with English translation].
Zheng Jie, Cellular and Molecular Biology of Cancer, Shanghai Science and Technology Press, Chapter 10, p. 188-189, Jan. 2011 [with English translation].
Thorne et al., "Immunotherapeutic potential of oncolytic vaccinia virus," Immunologic Research, 50:286-293 (2011).
European Search Report dated Jun. 30, 2017 in EP Application No. 14837931.6.
Gutman et al., "Development of recombinant vesicular stomatitis virus for use as oncolytic vector," Cytokine 56:84 (2011).
Hirvinen et al., "DAI-Armed Double Deleted Oncolytic Vaccinia Virus Displays Enhanced Anti-Tumor Activity by Eliciting a More Robust Anti-Tumor Immune Response," Molecular Therapy 21(Suppl. 1):S193-S194 (2013).
Rojas et al., "Manipulating TLR Pathways Activated By Oncolytic Vaccinia Virus Elicits a Potent Immune Response Against Tumors," Molecular Therapy 22(Suppl. 1):S12-S13 (2014).
Alcami, et al., "A Soluble Receptor for Interleukin-1β Encoded by Vaccinia Vims: A Novel Mechanism of Vims Modulation of the Host Response to Infection", Cell, 71:153-167(1992).
Breiman, et al., "Vaccinia vims B5 protein affects the glycosylation, localization and stability of the A34 protein", Journal of General Virology, 91:1823-1827 (2010).
Herrera, et al., "Functional Analysis of Vaccinia Vims B5R Protein: Essential Role in Virus Envelopment Is Independent of a Large Portion of the Extracellular Domain", Journal of Virology, 72(1):294-302 (1998).

* cited by examiner

REGULATORY T-CELLS

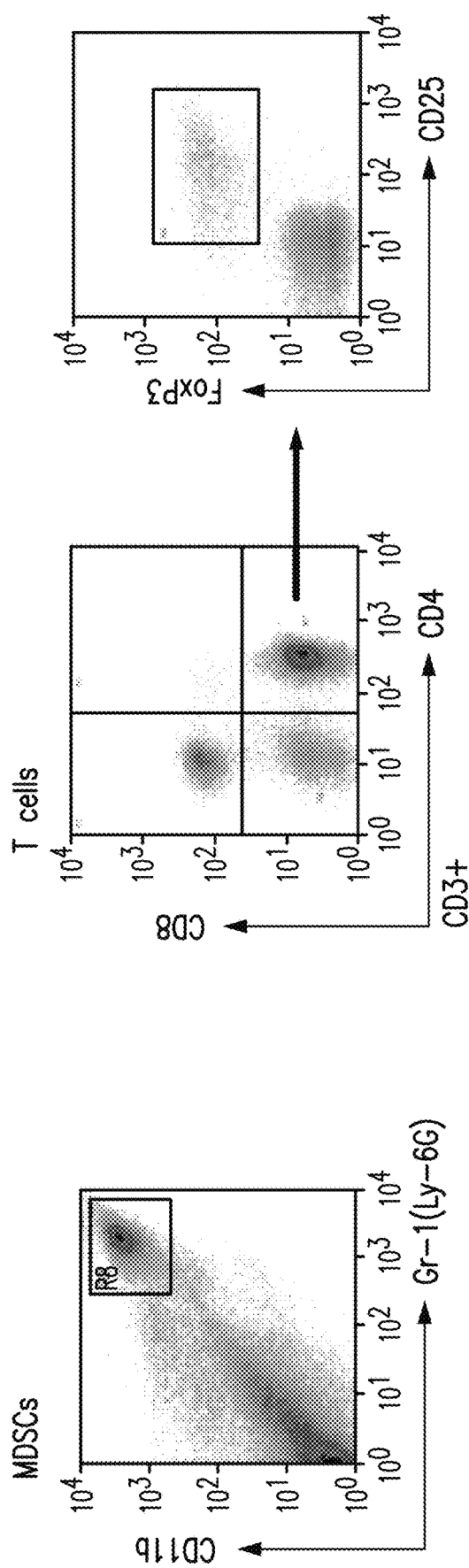
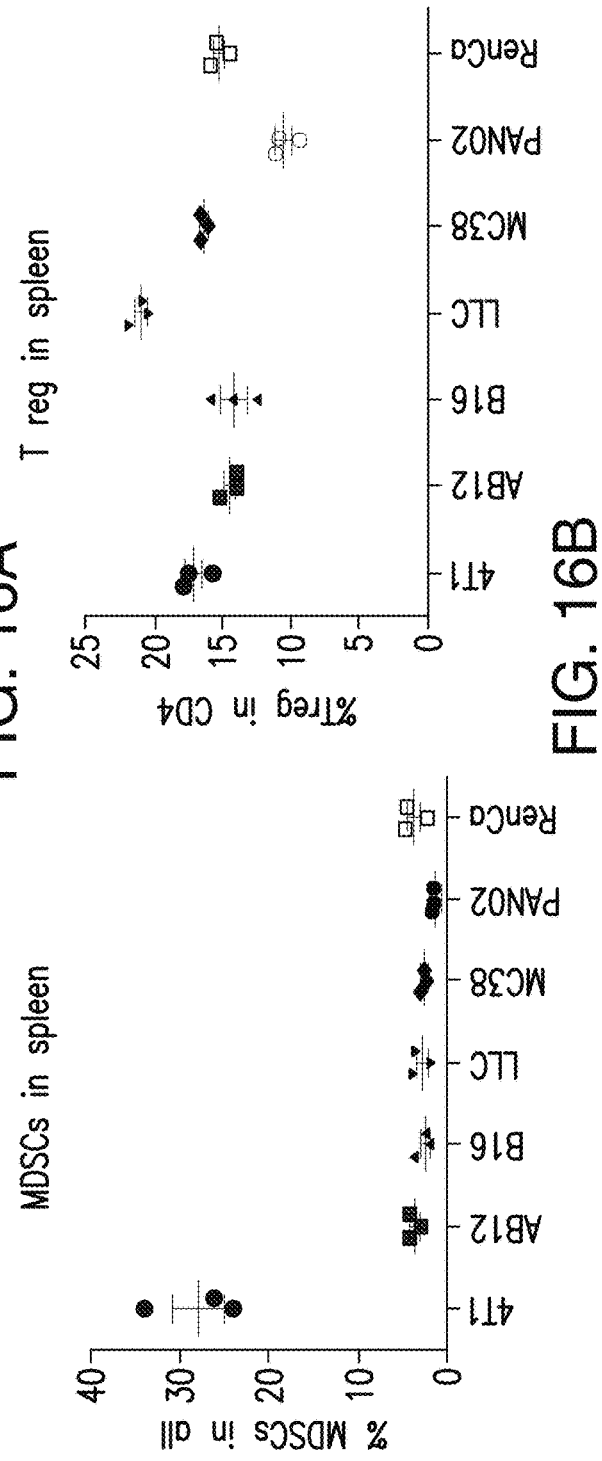
FIG. 16A
FIG. 16B

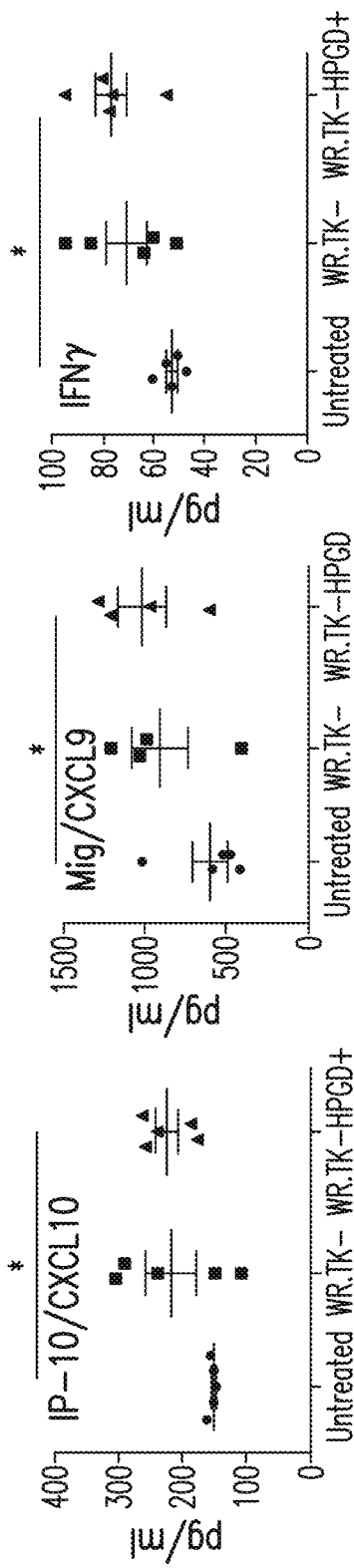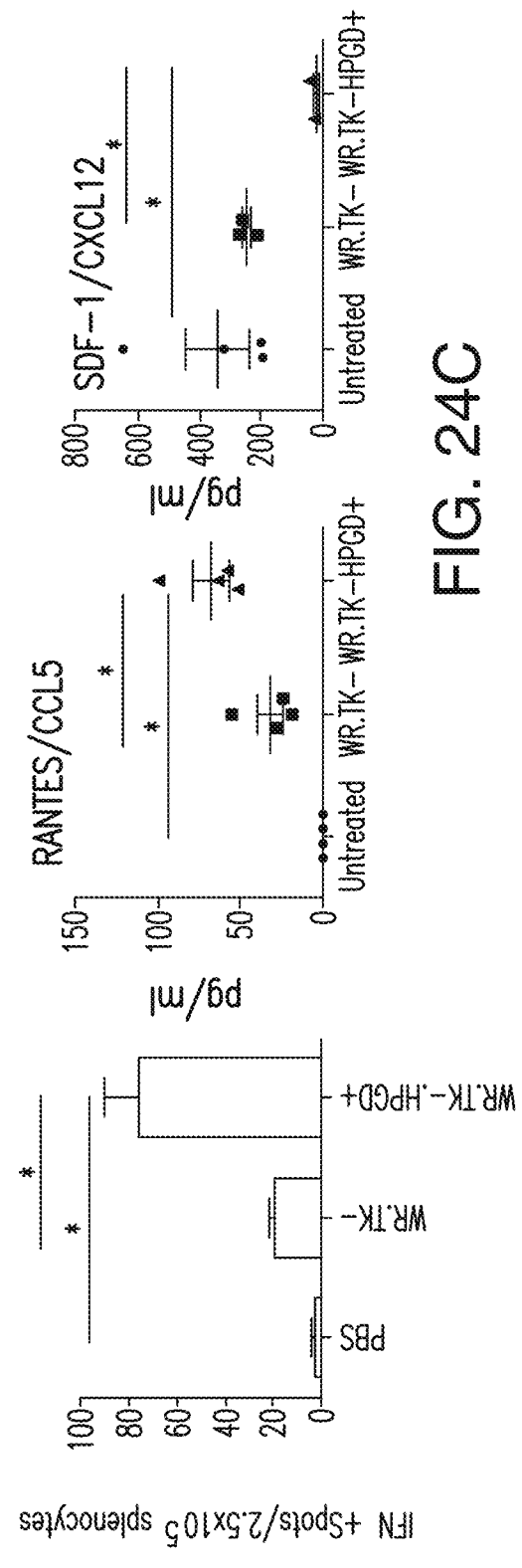
FIG. 24A  FIG. 24B  FIG. 24C

IMMUNO-ONCOLYTIC THERAPIES

CROSS-REFERENCE TO RELATED APPLICATIONS

This application is a continuation of International Patent Application No. PCT/US2014/052308, filed Aug. 22, 2014 and claims priority to U.S. Provisional Application Ser. No. 61/868,978, filed Aug. 22, 2013, to both of which priority is claimed and the contents of both of which are incorporated herein in their entireties.

1. INTRODUCTION

The present invention relates to oncolytic vaccinia viruses which have been modified to promote anti-tumor immunity and/or reduce host antibody response against the virus.

2. BACKGROUND OF THE INVENTION

Oncolytic viruses (OV) are viruses with replication that is naturally or engineered to be selective for tumor cells[1-3]. A variety of different viral backbones have been examined as OV, including strains of vaccinia virus (VV)[4-11]. At least three separate oncolytic vaccinia vectors have completed Phase I testing, including strain vvDD.[6-7] The VV OV, JX-594[4,12] (Jennerex), has recently demonstrated highly encouraging responses in Phase II trials for hepatocellular carcinoma (HCC), including systemic tumor delivery[13,14]. Further, encouraging Phase III results have been reported for the herpes virus HSV OV (T-Vec, Amgen[15,16]) in therapy of melanoma (16% responses, compared to 2% in control arm). As such, the true potential of OVs in the treatment of cancer has begun to be revealed (beyond that of the original ONYX-015 (H-101) adenovirus strain[17,18] that remains the only approved OV therapy in any market[19]).

Despite this promise, complete responses with OV remain rare. Significantly, the first and second generation OV strains were primarily designed to destroy tumor cells through selective replication leading directly to cell lysis. Additionally, JX-594 and T-Vec both express a cytokine transgene (GM-CSF) which would be expected to boost host lymphocytes.[12,14,20,21] Pre-clinical studies have demonstrated the critical importance of the immune response in the therapeutic activity of oncolytic VV, with (i) mice being uniformly resistant to re-challenge following a complete response after VV therapy, indicating an absolute requirement for induction of anti-tumor adaptive immunity[22]; (ii) the vaccine effects of VV demonstrating greater therapeutic benefit than equivalent DC vaccines[23]; (iii) VV infection of the tumor producing a hallmark cytokine profile (the 'Immunologic Constant of Rejection'[24]); (iv) VV therapy reducing the number of immunosuppressive cells in the tumor (MDSC, T-reg and M2 macrophages)[25]; (v) the immune response raised by VV therapy being capable of eradicating residual tumor and metastases well after the virus has been cleared, providing long-term immune surveillance to prevent relapse[22,25,26]; and (vi) in some studies it appears that robust viral replication is not actually needed for therapeutic effect[27,28]. Therefore, the immunotherapeutic effects of OVs, particularly VV, are at least as important as the directly oncolytic effects and that these vectors should probably be considered principally as immunotherapies.

Notably, the current clinical vectors were not designed as immunotherapeutics (beyond the expression of single cytokines) and this area has remained relatively underexplored. As such, there is huge unmet potential to enhance oncolytic vectors through optimizing their interactions with the host immune system and to create vectors capable of in situ vaccination against relevant tumor antigens. Alternatively, most traditional therapeutic cancer vaccine approaches have had limited success in the clinic especially against larger tumors, despite evidence of successful immunization[29-31]. Novel vaccine approaches are therefore also needed, ideally mediating induction of responses against relevant antigens in every tumor, overcoming suppression even within large tumors and enhancing T-cell homing to the tumor targets.

3. SUMMARY OF THE INVENTION

The present invention relates to "immuno-oncolytic" vaccinia viruses which have been modified to promote anti-tumor immunity and/or reduce host immune and antibody response against the virus. It is based, at least in part, on the discovery of improved inhibition of tumor growth by oncolytic vaccinia virus that has been treated with an agent that reduces the amount of glycosylation and/or treated with a sialidase enzyme (which are believed to reduce TLR2 activation and to decrease host antibody response against the virus); and/or carries modifications or deletions of viral genomic nucleic acid encoding a product that reduces T cell immunity (viral interleukin-18 binding protein); and/or carries nucleic acid encoding a product that (i) enhances cytotoxic T lymphocyte induction (TRIF) and/or (ii) reduces tumor myeloid-derived suppressor cells (MDSCs) by reducing prostaglandin E2. Accordingly, the present invention provides for immuno-oncolytic vaccinia viruses and methods of using them in the treatment of cancers.

4. BRIEF DESCRIPTION OF THE FIGURES

Figure 1B:
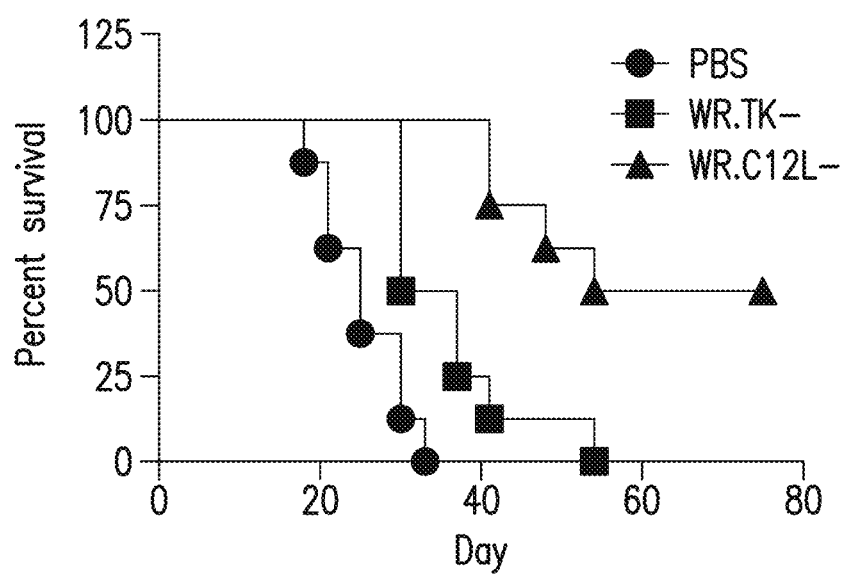
Figure 1C:
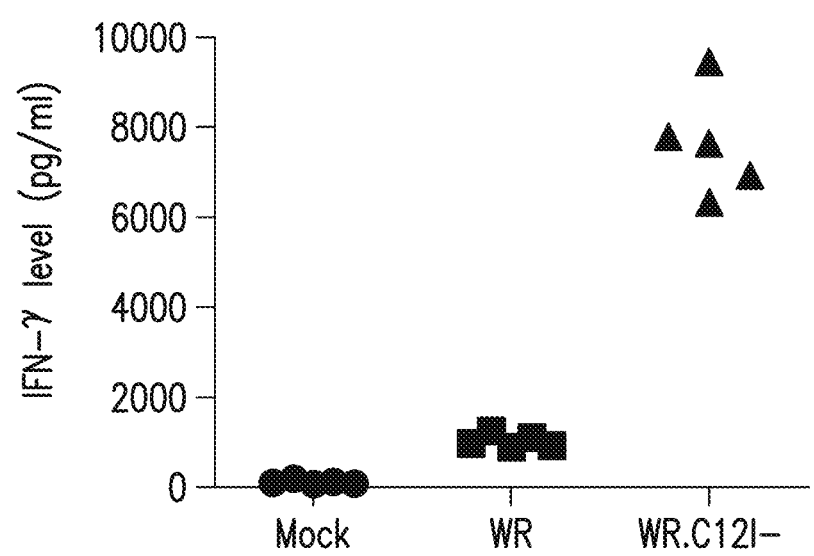

FIG. 1A-C. (A) WR.ΔC12L virus displayed tumor selectivity in vivo relative to WR parental virus. C57BL/6 mice bearing CMT-93 tumors were treated IV with 5e8 PFU of viruses, and mice sacrificed at pre-determined times after therapy. Viral PFU were quantified in different tissues post mortem after homogenization. (B) Enhanced anti-tumor effects of WR.ΔC12L. Mice bearing subcutaneous CMT-93 tumors were treated IV with a single dose (1e8 PFU) of virus and survival followed (defined as time to tumor volume reaching 1000 mm$^3$ as determined by caliper measurement). (C) Production of IFN-γ (as a marker of effector T-cell production) from splenocytes recovered from mice previously treated with indicated virus and after ex vivo exposure to WR.

FIG. 2A-E. Deglycosylation of Vaccinia Virus envelope. (A) Immunoblot showing deglycosylation of Vaccinia virus envelope protein. Purified WR and WR deglycosylated viruses were disrupted and blotted using an anti-B5R antibody. Decrease in protein weight corresponds to deglycosylation of the B5R protein. (B) Deglycosylation of virus envelope has no effect on Vaccinia virus infectivity. Different mouse tumor cell lines were infected with TK- or its deglycosylated version at an MOI of 1, and viral luciferase expression was measured 3 hours after infection by bioluminescence imaging. Mean values +SD of 3 independent experiments are plotted. (C) Deglycosylation reduces TLR2 activation in vitro. HEK293 cells expressing mouse TLR2 were transfected with pNiFty (TLR-signaling reporter plasmid). 24 hours after transfection, cells were infected at an MOI of 1 with WR or WR deglycosylated and TLR2 activation was quantified 24 hours after infection by bioluminescence imaging. Means+SD of 3 independent experiments (performed in quadruplicate) are depicted. (D) STAT3 phosphorylation is depleted in splenic lymphocytes of mice injected with deglycosylated Vaccinia. Percentage of pSTAT1-pSTAT3+ lymphocytes was determined by flow cytometry. PBS and PAM(3)CSK(4) were used as controls. Values of individual mice and means±SEM of the different treatments are plotted. (E) Deglycosylation of Vaccinia envelope increases viral gene expression from tumors in vivo. BALB/c mice harboring subcutaneous xenografts of Renca cells (mouse renal adenocarcinoma) were randomized and injected with a single intravenous dose of $1 \times 10^8$ PFU per mouse of TK- or TK-deglycosylated. Kinetics of viral gene expression from within the tumor was monitored by bioluminescence imaging of viral luciferase expression. Mean values of 12-13 animals +SD are plotted. *, significant P<0.05 compared with PBS or Control. #, significant P<0.05 compared with TK- or WR group. φ, significant P<0.05 compared with PAM(3)CSK(4) group.

FIG. 3A-D. Ablating TLR2 activation through deglycosylation leads to increased therapeutic effects. (A) Treatment of vaccinia strain WR with a sialidase enzyme (DS) results in loss of TLR2 signaling pathway activation in an in vitro model (NF-kB activation in HEK293 cells transfected to express TLR2). (B) DS WR virus displayed significantly enhanced systemic delivery to mouse tumors (4T1 subcutaneous tumors in BALB/c mice with virus delivered IV and viral luciferase transgene expression in the tumor determined 24 h later by bioluminescence imaging (N.B. non-tumor tissues displayed no difference in viral uptake). (C) Anti-tumor effect in the same model demonstrated therapeutic advantage of DS the virus. (D) Loss of TLR2 activation (in a TLR2 knock out transgenic mouse) after infection with vaccinia leads to significantly reduced induction of anti-viral neutralizing antibody (neutralizing antibody measured as the ability of different dilutions of mouse serum collected 14 d after treatment with WR to prevent viral luciferase transgene expression after mixing with WR.TK-Luc+ and infection of a BSC-1 cell layer).

Figure 4A:
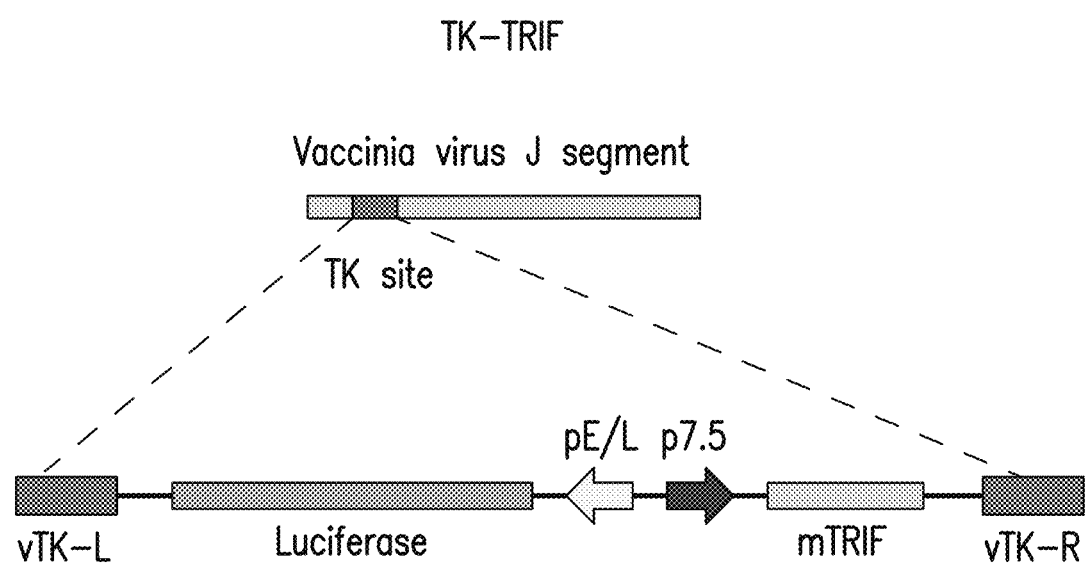
Figure 4A:
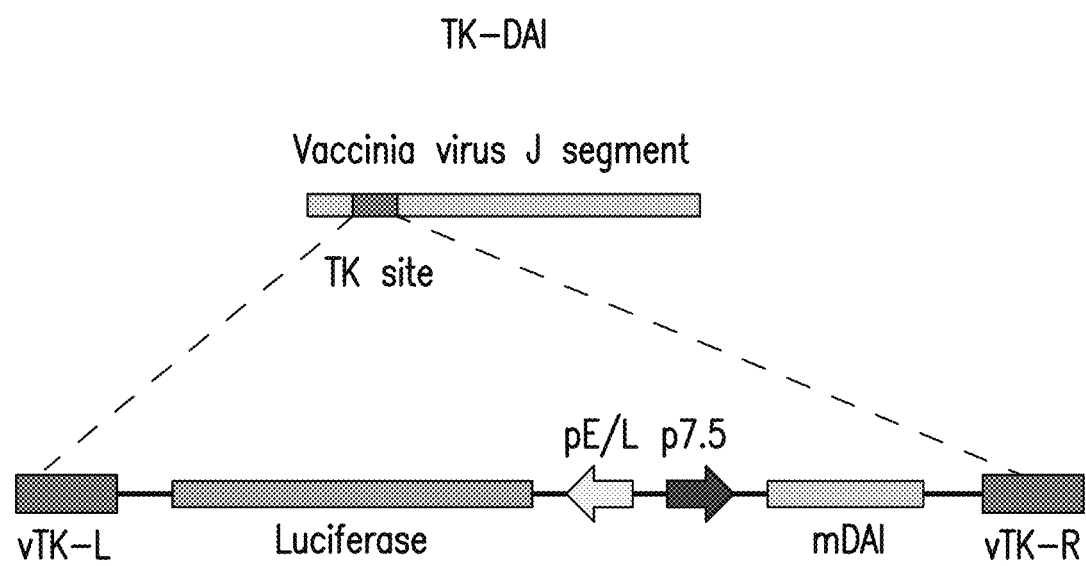
Figure 4B:
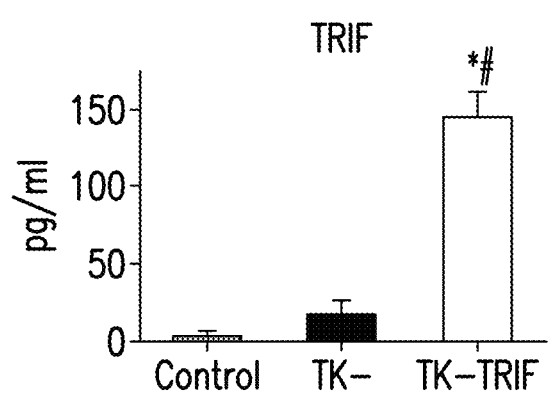
Figure 4C:
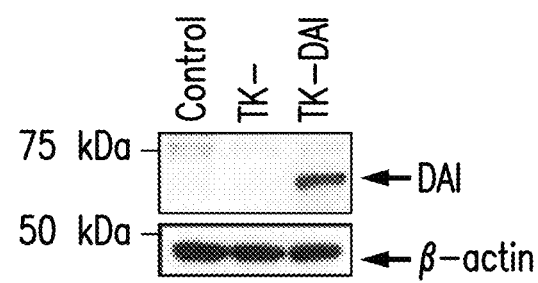

FIG. 4A-C. (A) Schematic diagram representing the construct of the TK-TRIF virus and a schematic diagram representing the construct of the TK-DAI virus. (B) ELISA assays were utilized to determine concentrations of TRIF in cells with infected with TK- and TK-TRIF. (C) Western blot showing the expression of DAI from the TK-DAI reference.

Figure 5A:
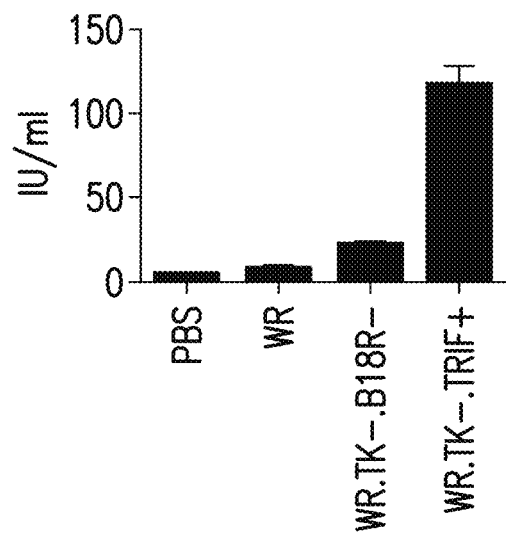
Figure 5B:
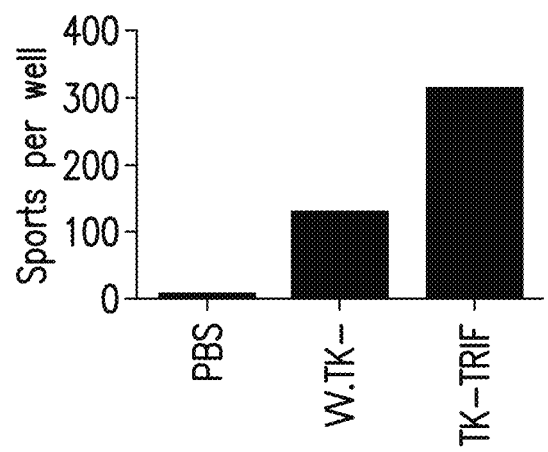
Figure 5C:
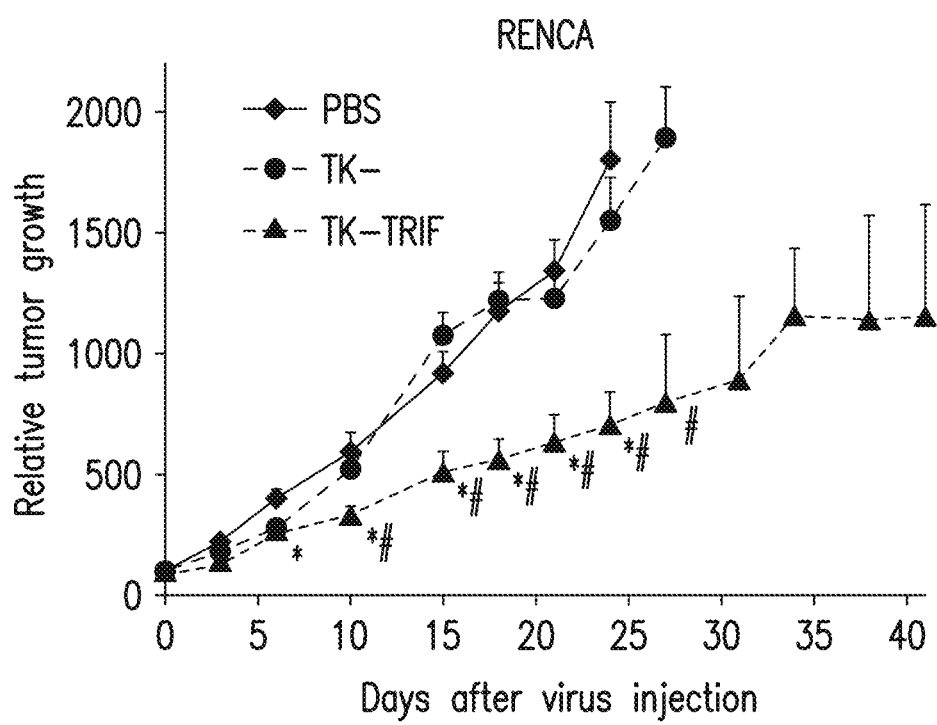

FIG. 5A-C. (A) TRIF expression from vaccinia enhances type I IFN production in vitro, even beyond that of the B18R-strain. (B) TRIF expression increased production of CTL in vivo. (C) Further enhanced therapeutic effect in vivo after single IV delivery of 1e8 PFU of virus to BALB/c mice bearing subcutaneous Renca tumors.

FIG. 6A-D. Oncolytic Vaccinia virus expressing the mouse TRIF protein increased activation of TLR-responding pathways and the release of proinflammatory cytokines and chemokines. (A-B) Activation of NF-κB (A) and IRF3 (B) pathways after infection with TK-TRIF and TK-DAI. ELISA assays were utilized to determine concentrations of pIKKβ and IRF3 on cytoplasmic and nuclear extracts, respectively, of 4T1 or MEF cells infected with TK-, TK-TRIF, or TK-DAI at an MOI of 1. Analyses were performed 24 hours after infection. Data was obtained in quadruplicated from 2 independent experiments, and is plotted as fold change vs TK-+SD. Dashed line indicates TK-activation level. (C) Release of cytokines and chemokines in vitro after TK-TRIF and TK-DAI infection. IL-6, IP-10, TNF-α, and IFN-β concentrations in the supernatant of Renca, 4T1, MC38 and MEF cells was evaluated by Luminex assay 24 hours after infection with TK-, TK-TRIF or TK-DAI (MOI of 1). Data is depicted as fold change vs TK-+SD (2 independent experiments). Dashed line indicates TK-concentrations. (D) In vivo intratumoral concentration of cytokines and chemokines. BALB/c mice with established Renca subcutaneous xenografts were randomized and injected with a single intravenous dose of $1 \times 10^8$ PFU per mouse of TK- or TK-TRIF. Fold change vs TK-from 4-5 mice+SD is plotted. Dashed line indicates TK-concentrations. *, significant P<0.05 compared with TK-group. #, significant P<0.05 compared with TK-DAI group.

FIG. 7A-E. ELISA assays were utilized to determine concentration of NF-κB (A), HMGB1 (B) and Hsp-70 (C) in cells infected with TK-, TK-TRIF or TK-DAI at an MOI of 1. Analyses were performed 24 hours after infection. Data was obtained and plotted as fold change vs TK-+SD. Dashed line indicates TK-activation level. The level of helper T-cells (D) and regulatory T-cells (E) were analyzed in response to infection with TK- or TK-TRIF virus.

FIG. 8A-D. Replication and antitumor activity of TK-TRIF and TK-DAI. (A) Viral production of TK-TRIF and TK-DAI in mouse tumor cells. Different tumor cell lines were infected with an MOI of 1 and virus production was measured by plaque-assay at different time points. Viral yield was evaluated in quadruplicate for each cell line, by carrying out two independent experiments. Means+SD are plotted. (B) Comparative cytotoxicity of TK-TRIF and TK-DAI. Cells were infected with the indicated viruses at doses ranging from 75 to 0.00025 PFU/cell. $EC_{50}$ values (MOI required to cause a reduction of 50% in cell culture viability) at day 4 after infection is shown. Four different replicates were quantified for each cell line and mean for each MOI is depicted. (C-D) Viral gene expression and antitumor efficacy in vivo. Renca or MC38 xenografts were implanted in BALB/c or C57BL/6 mice, respectively, and mice were injected with PBS or $1 \times 10^8$ PFU of TK-, TK-TRIF or TK-DAI through the tail vein. Viral luciferase expression in the tumors (C) and tumor volumes (D) were measured at indicated time points. n=12-15 mice/group+SE. *, significant P<0.05 compared with PBS group. #, significant P<0.05 compared with TK-group. φ, significant P<0.05 compared with TK-DAI group.

FIG. 9A-F. (A) Viral gene expression of TK-TRIF and TK-DAI in mouse tumor cells. Different tumor cell lines were infected with an MOI of 1 and viral luciferase expression was quantified by bioluminescence imaging at different time points. Luciferase expression was evaluated in quadruplicate for each cell line, by performing two independent experiments. Means+SD are plotted. (B) Percentage of apoptotic cells after infection with TK-TRIF and TK-DAI. A panel of mouse tumor cell lines was infected with the indicated viruses using an MOI of 1. At 48 hours after infection, percentage of nectrotic and apoptotic cells were determined by flow cytometry by PI and Annexin V staining. Two independent experiments were performed and means+SD are plotted. (C-D) TK-TRIF improves the antitumor efficacy of TK-GMCSF in a mammary semi-orthotopic model. 4T1 cells were implanted in the mammary fat pad of BALB/c mice and, once the tumor was established, mice were injected with PBS or $1 \times 10^8$ pfu of TK-, TK-TRIF, or TK-GMCSF through the tail vein. Viral luciferase expression from within the tumors (C) and tumor volumes (D) were measured at indicated time points. n=12-14 mice/group+SE. (E-F) TK-TRIF improves survival of mice bearing tumors. BALB/c or C57BL/6 mice harboring Renca (E) or MC38 (F) xenografts, respectively, were treated as in FIG. 3d and end point was established at a tumor volume of ≥750 mm³. Kaplan-Meyer survival curves are plotted. n=12-15 mice/group. *, significant P<0.05 compared with PBS or control. #, significant P<0.05 compared with TK-group. φ, significant P<0.05 compared with TK-GMCSF group. ω, significant P<0.05 compared with TK-DAI group.

FIG. 10A-E. (A) Body weight variation after intravenous TK-TRIF deglycosylated administration. BALB/C mice were injected intravenously with $1 \times 10^8$ PFU per mouse of TK-, TK-TRIF, or TK-TRIF deglycosylated. Phosphate-buffered saline (PBS) administration was used in the control group. TK-injected mice presented more than 10% reduction in body-weight at day 6 after virus injection, whereas TK-TRIF and TK-TRIF deglycosylated-injected mice presented a similar weight profile than those injected with PBS. (B) Viral gene expression in vivo after TK-TRIF deglycosylated administration. Renca tumors were implanted in BALB/c mice, and mice were injected with PBS or $1 \times 10^8$ pfu of TK-, TK-TRIF, or TK-TRIF deglycosylated through the tail vein. Viral luciferase expression from within the tumors was measured at indicated time points. n=12-14 mice/group+SE. (C-D) Survival of tumor-bearing mice treated with TK-TRIF deglycosylated. (C-D) Renca (C) or MC38 (D) xenografts were established in BALB/C or C57BL/6 mice, respectively, and treated with a single intravenous dose of $1 \times 10^8$ PFU of indicated viruses or PBS. End point was established at a tumor volume of ≥750 mm³ and Kaplan-Meyer survival curves are plotted. n=12-15 mice/group. (E) TK-TRIF deglycosylated improved survival compared with TK-GMCSF treatment. Mice (BALB/c harboring subcutaneous Renca tumors) were treated via tail vein injection of PBS or a single dose of $1 \times 10^8$ pfu of TK-GMCSF or TK-TRIF deglycosylated (n=10-12 per group). Kaplan-Meyer survival curves were obtained after establishing an end point of ≥750 mm³ for the tumor volume. *, significant P<0.05 compared with PBS group. #, significant P<0.05 compared with TK-group. φ, significant P<0.05 compared with TK-deglycosylated group. ω, significant P<0.05 compared with TK-TRIF group. Ψ, significant P<0.05 compared with TK-GMCSF group.

FIG. 11A-F. Combination of envelope deglycosylation and mouse TRIF expression boosted antitumor cellular responses and exhibited potent antitumor efficacy. (A-B) Cellular immune responses to Vaccinia virus and tumor cells evaluated by IFN-γ ELISpot assay. At day 7 post-virus administration, spleens were harvested from mice injected intravenously with $1 \times 10^8$ PFU of indicated viruses or PBS (BALB/c mice bearing Renca xenografts) and evaluated for the amount of CTLs recognizing Vaccinia virus (A) or Renca cells (B). Values of individual mice and means±SEM are depicted. (C) Serum neutralizing antibody titers. A neutralizing assay was performed to determine circulating anti-Vaccinia antibody levels for mice injected with $1 \times 10^8$ PFU of TK-, TK-TRIF or TK-TRIF deglycosylated. Nabs titers were determined by the highest dilution of serum that resulted in at least 50% inhibition of infection. Values of individual mice and means±SEM are plotted. (D-E) In vivo antitumor activity in different models. BALB/c bearing Renca (D) or C57BL/6 bearing MC38 (E) tumor xenografts were treated with a single intravenous dose of indicated viruses ($1 \times 10^8$ PFU/mouse). Tumor growth was followed by caliper measurements. Means of 12-15 mice per group+SE are depicted. (F) TK-TRIF deglycosylated exhibited greater antitumor activity than TK-GMCSF. BALB/c mice harboring Renca xenografts were injected intravenously with a dose of $1 \times 10^8$ PFU/mouse of TK-GMCSF or TK-TRIF deglycosylated. Relative tumor volume after virus administration is plotted (n=12-15 mice/group+SE). *, significant P<0.05 compared with PBS group. #, significant P<0.05 compared with TK-group. φ, significant P<0.05 compared with TK-deglycosylated group. ω, significant P<0.05 compared with TK-TRIF group.

Figure 12A:
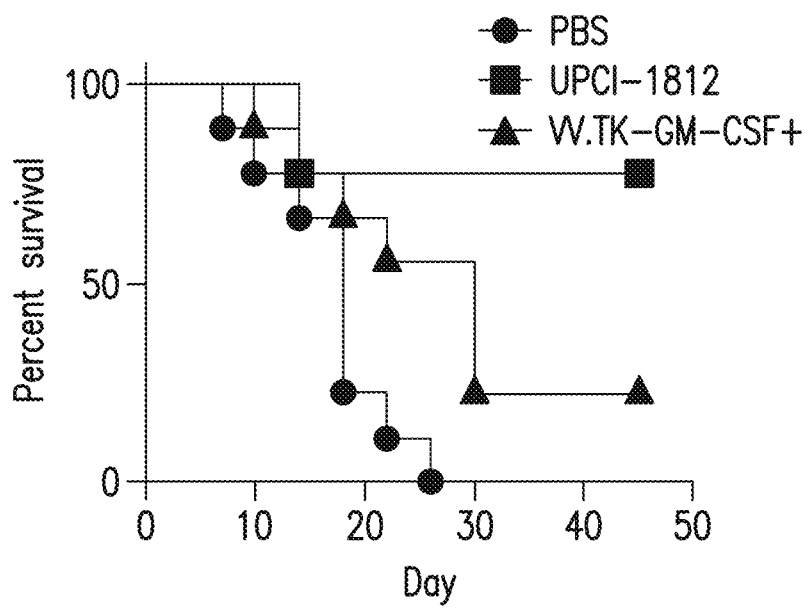
Figure 12B:
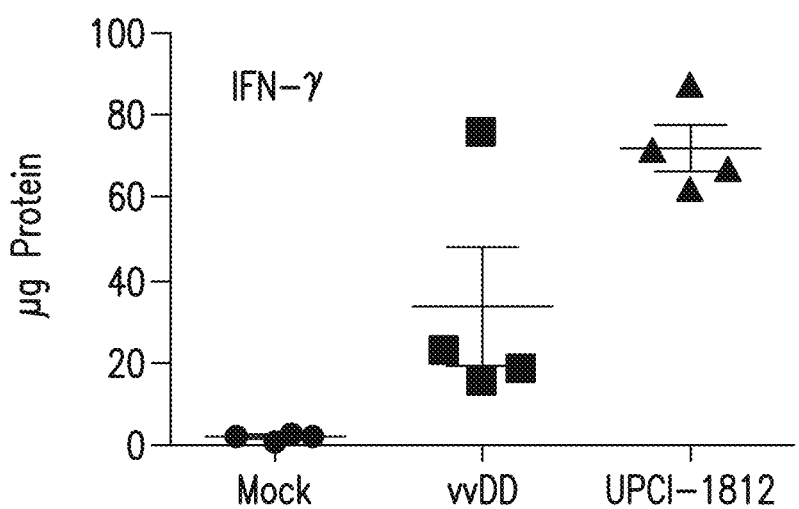
Figure 12C:
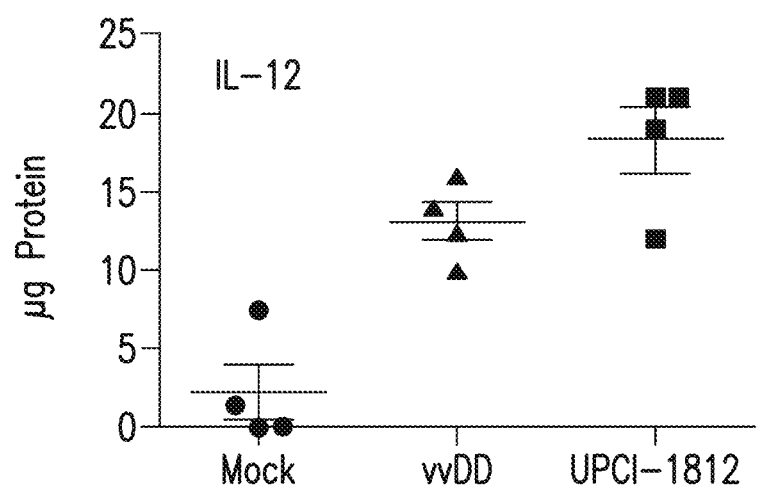

FIG. 12A-C. (A) Vaccinia strain WR with DS treatment, C12L deletion and mTRIF expression (termed UPCI-1812) displayed enhanced anti-tumor effects in BALB/c mice bearing 4T1 tumors relative to current clinical strains WR.TK-GM-CSF+ (as a model of the strain JX-594). The UPCI-1812 virus also displayed increased production of immunotherapeutic cytokines in the tumor microenvironment including (B) interferon gamma and (C) interleukin-12.

Figure 13A:
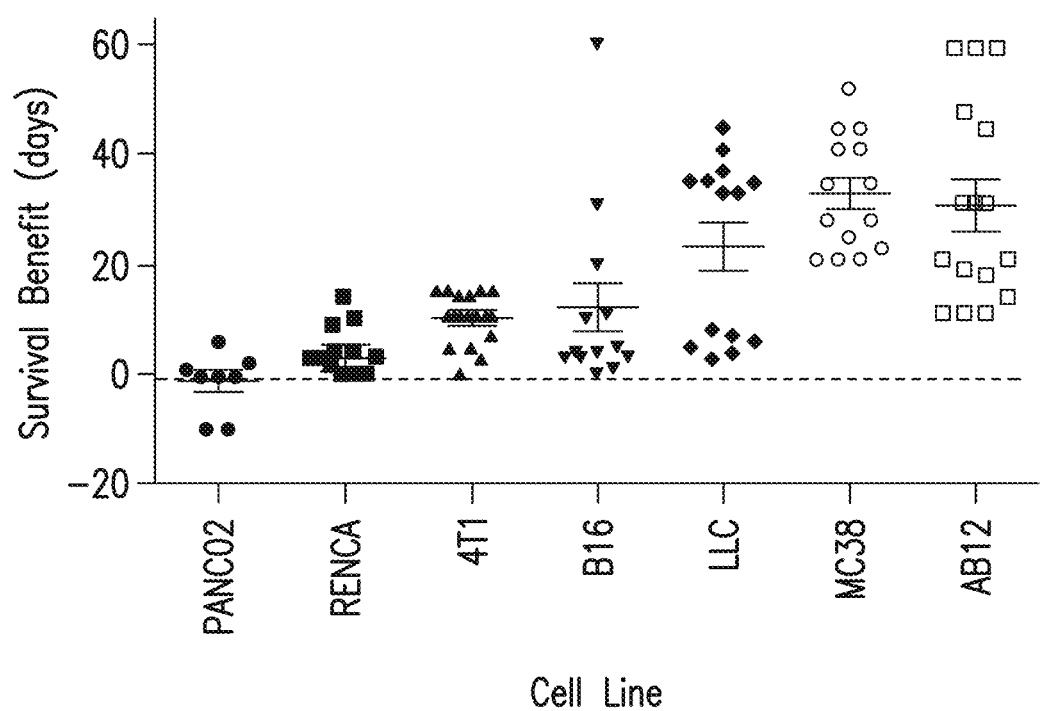
Figure 13B:
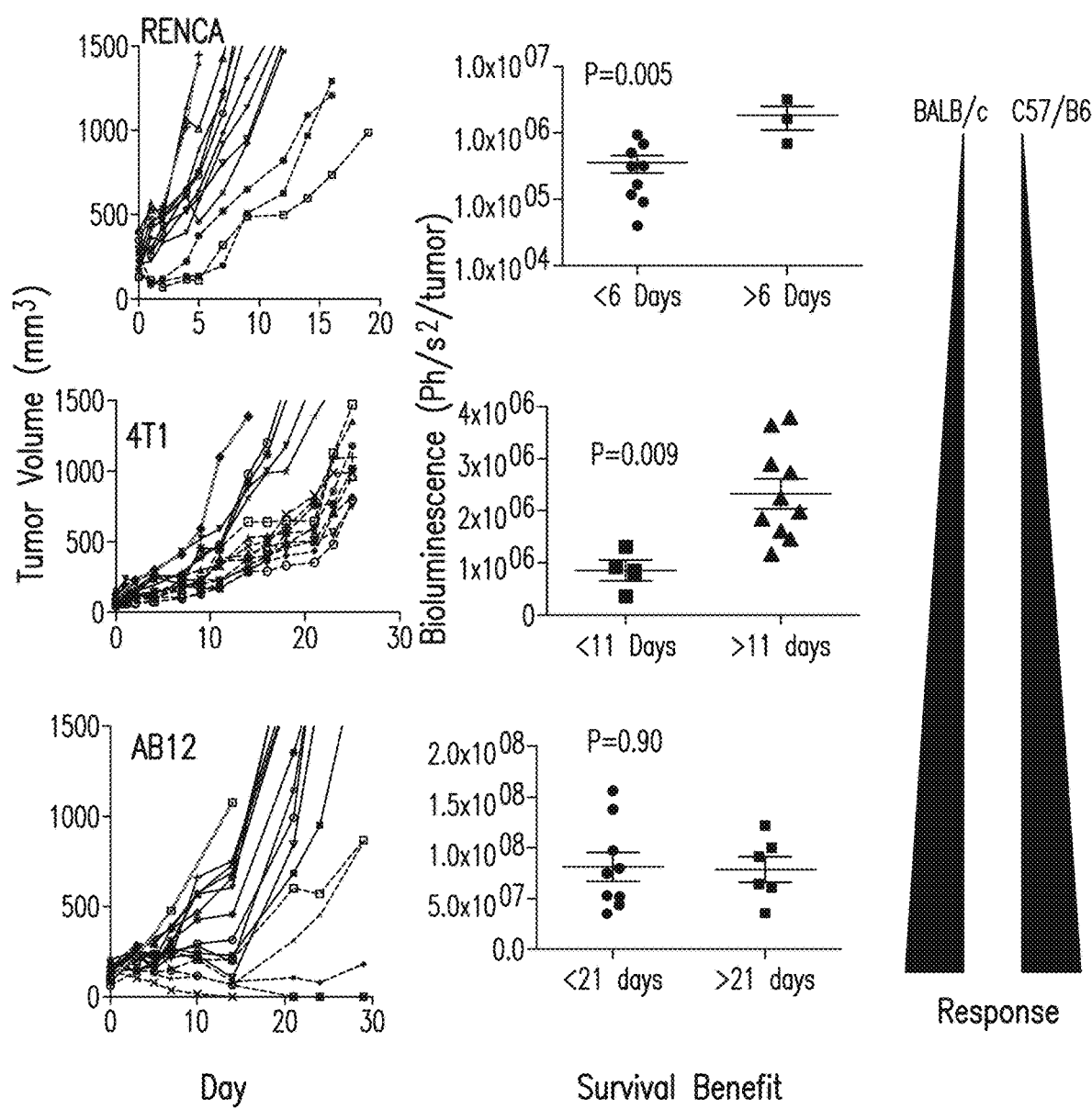
Figure 13B:
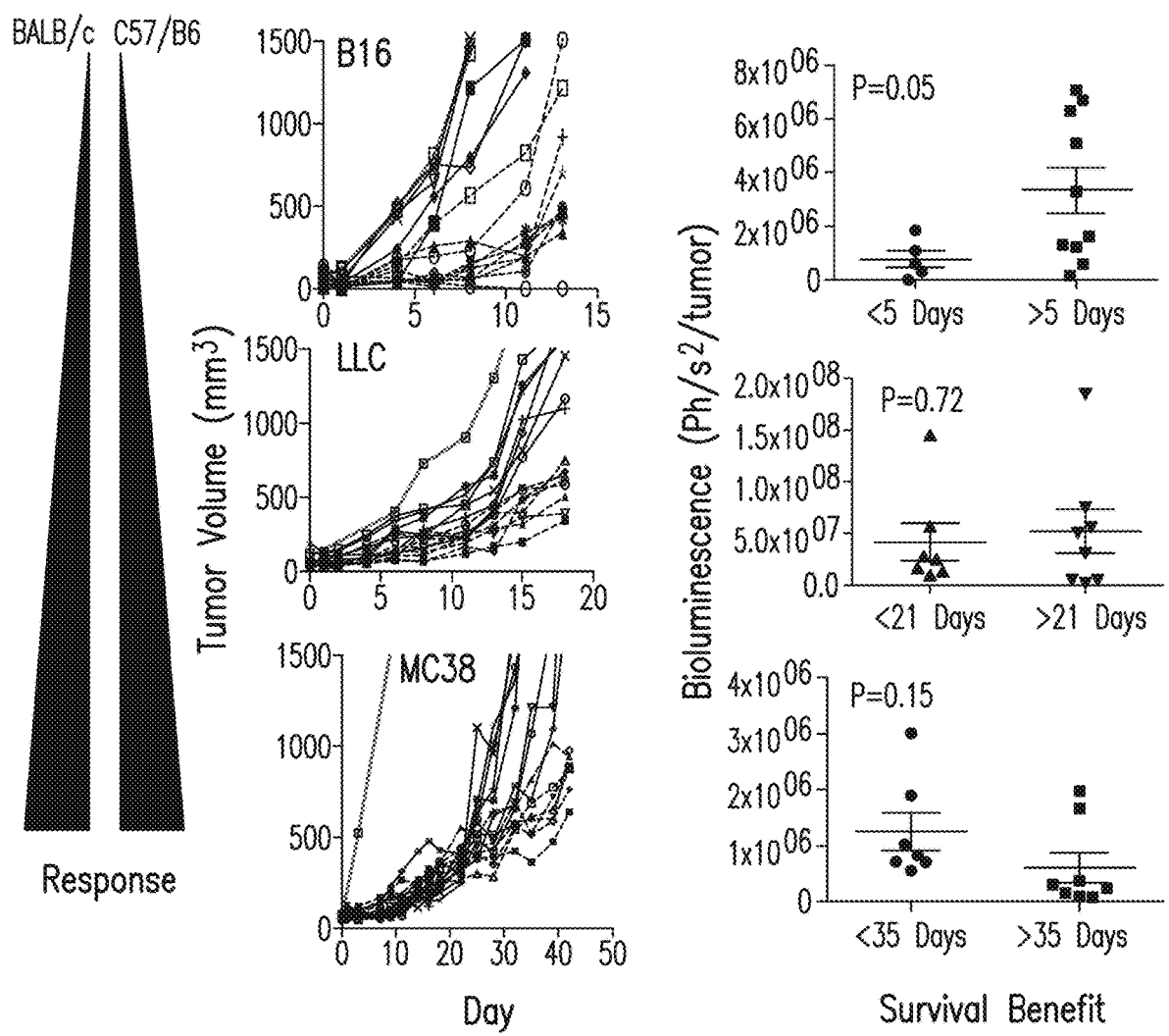
Figure 13C:
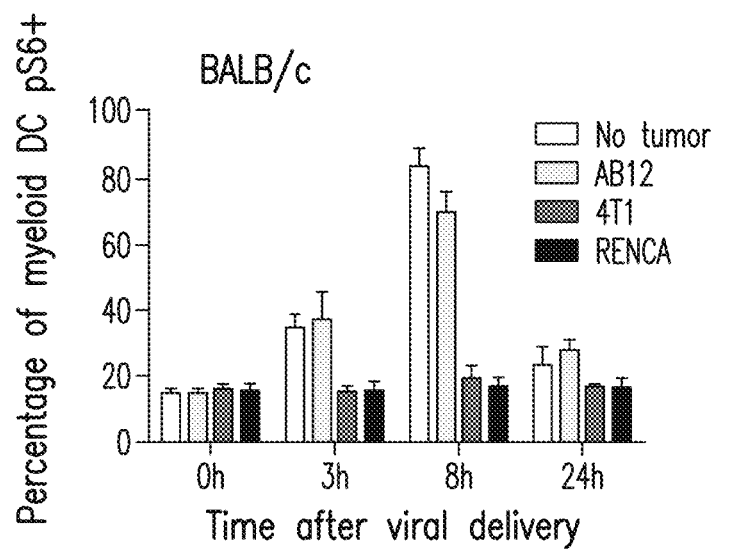
Figure 13C:
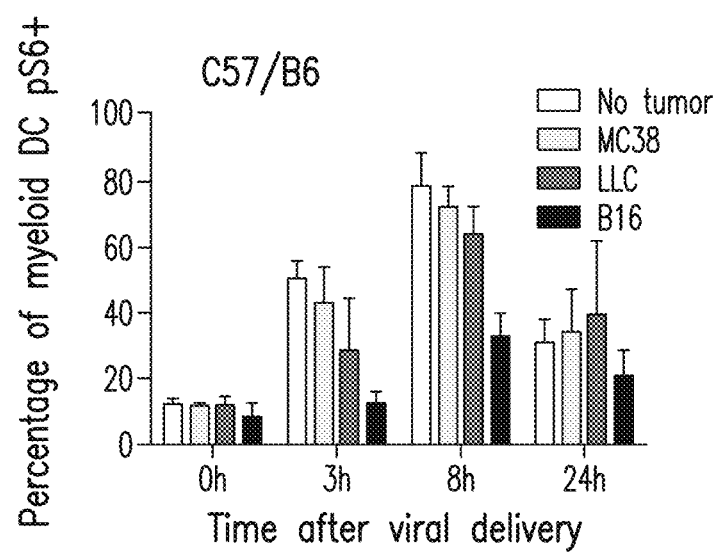

FIG. 13A-C. (A) Survival of various tumor cells lines were analyzed upon viral infection with TK-. (B) Viral gene expression in tumors derived from BALB/c and C57BL/6 mice implanted with certain tumor cell lines, and the volume of tumors obtained from BALB/c and C57BL/6 implanted with certain tumor cell lines and infected with TK-. (C) Detection of phosphorylated Sp6 in myeloid cells in tumors derived from BALB/c and C57BL/6 mice implanted with certain tumor cell lines and treated with TK-.

Figure 14A:
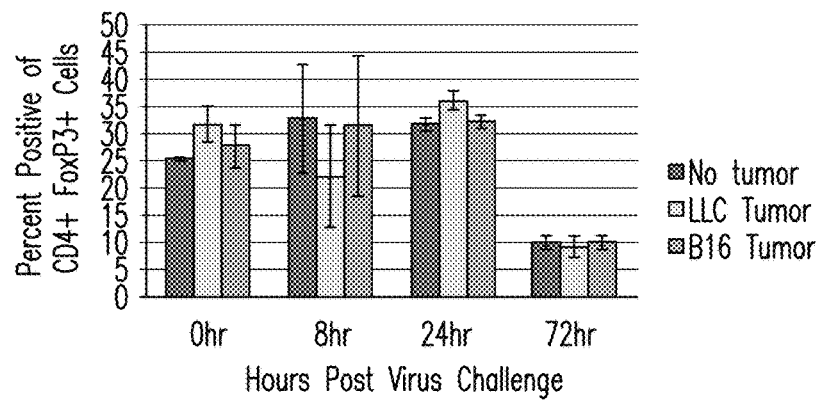
Figure 14A:
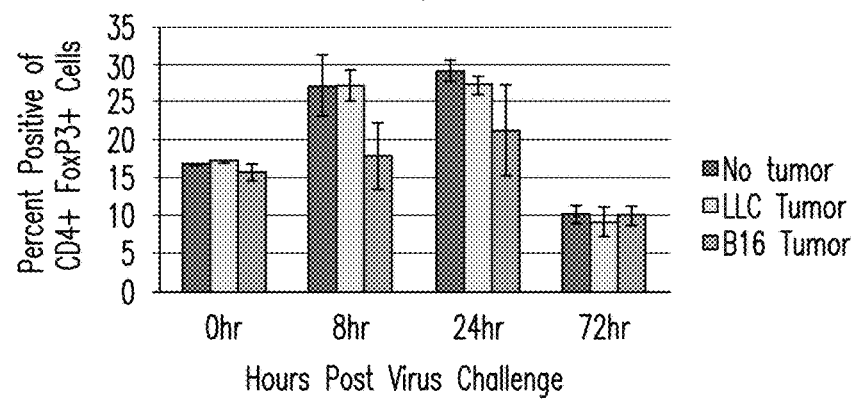
Figure 14A:
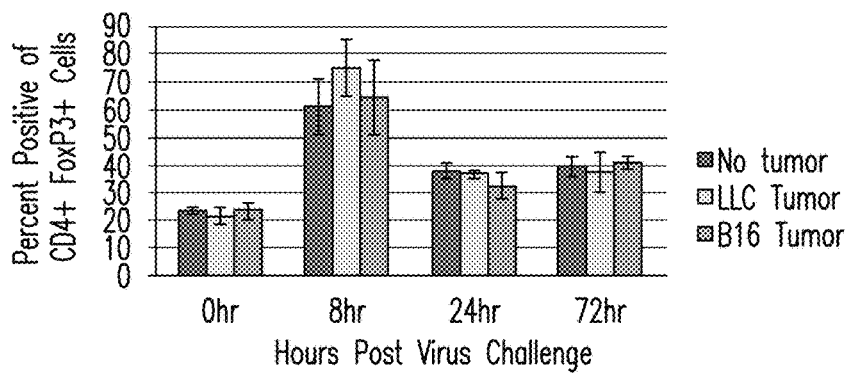
Figure 14A:
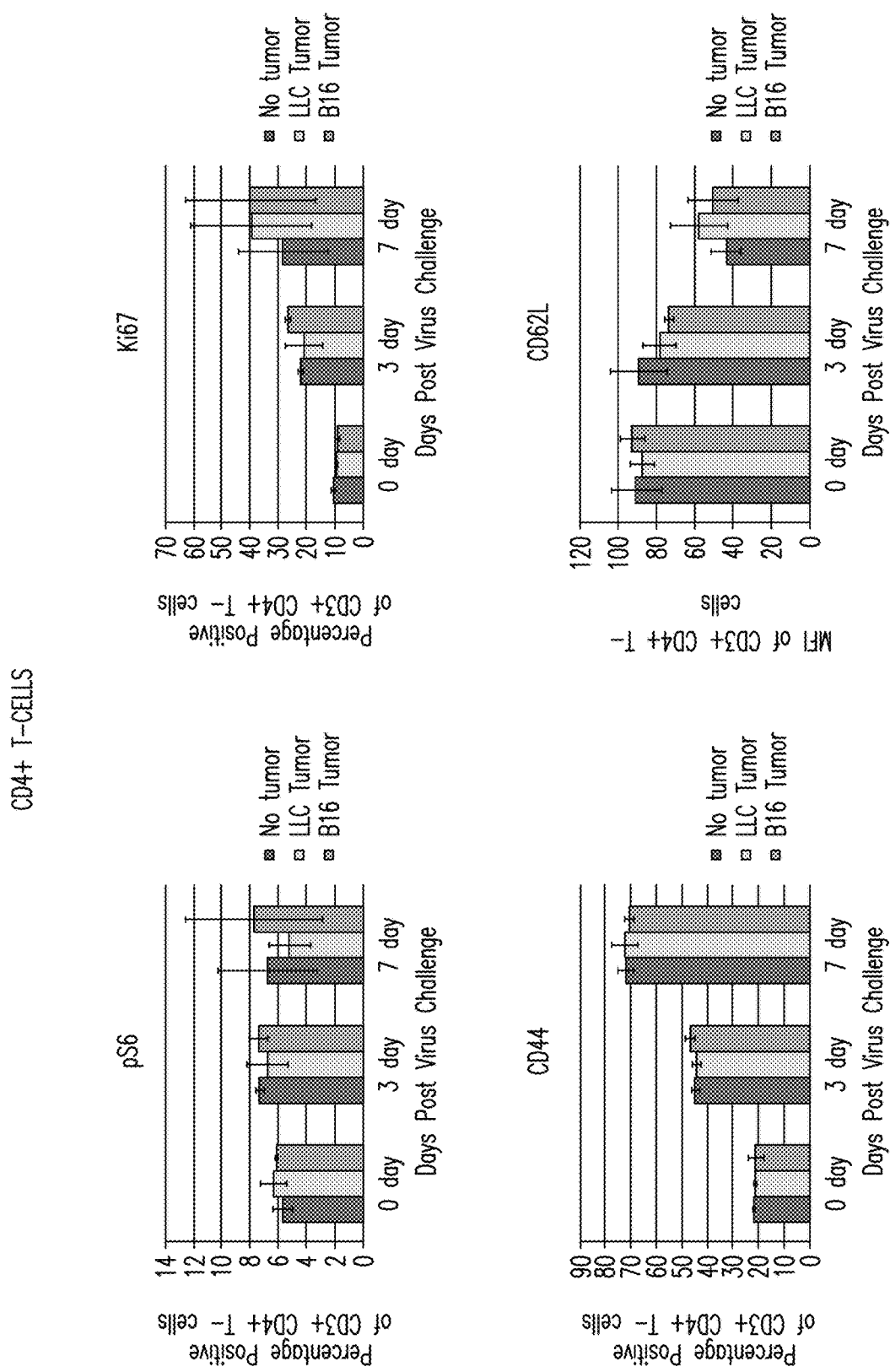
Figure 14A:
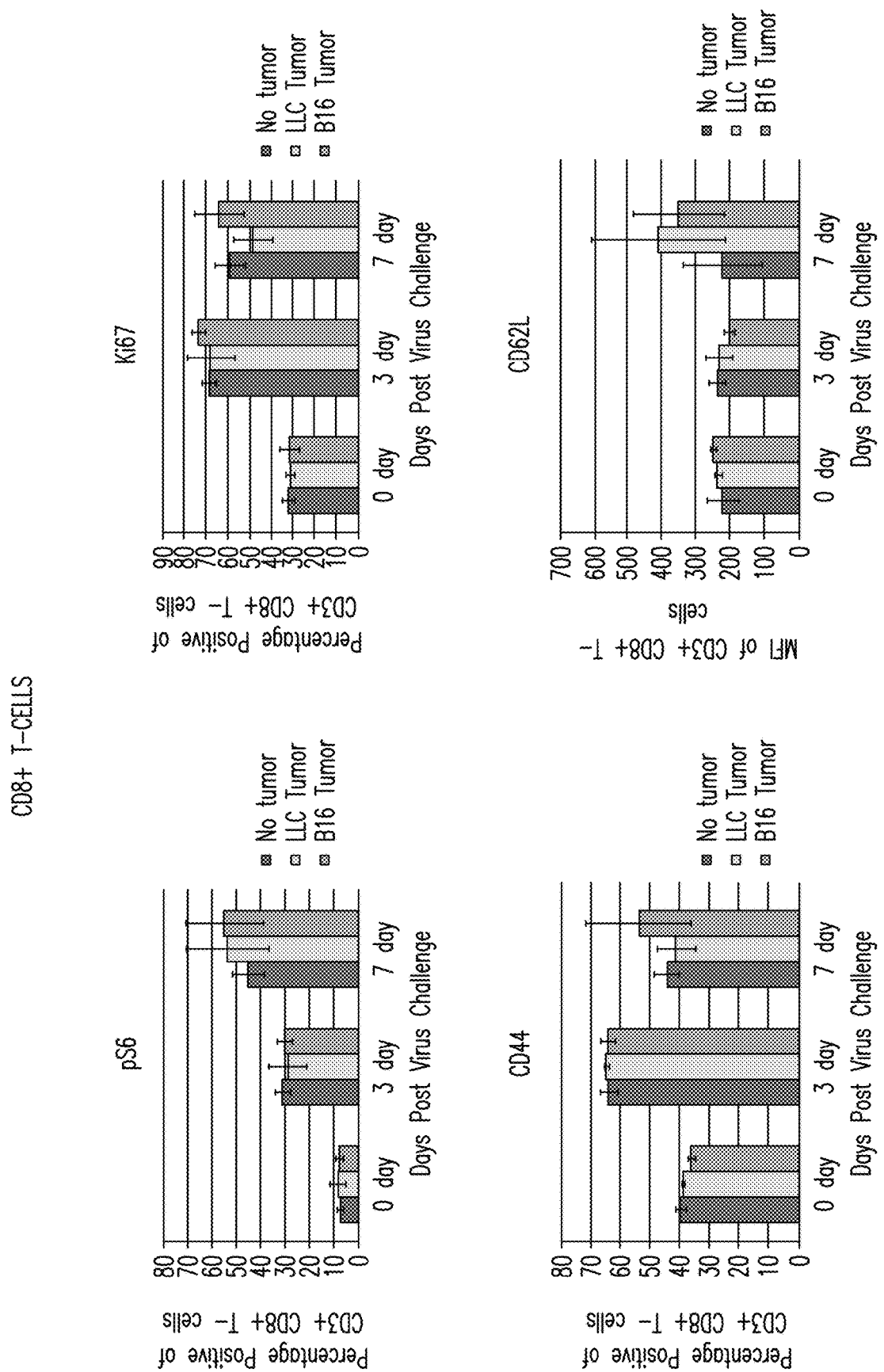
Figure 14B:
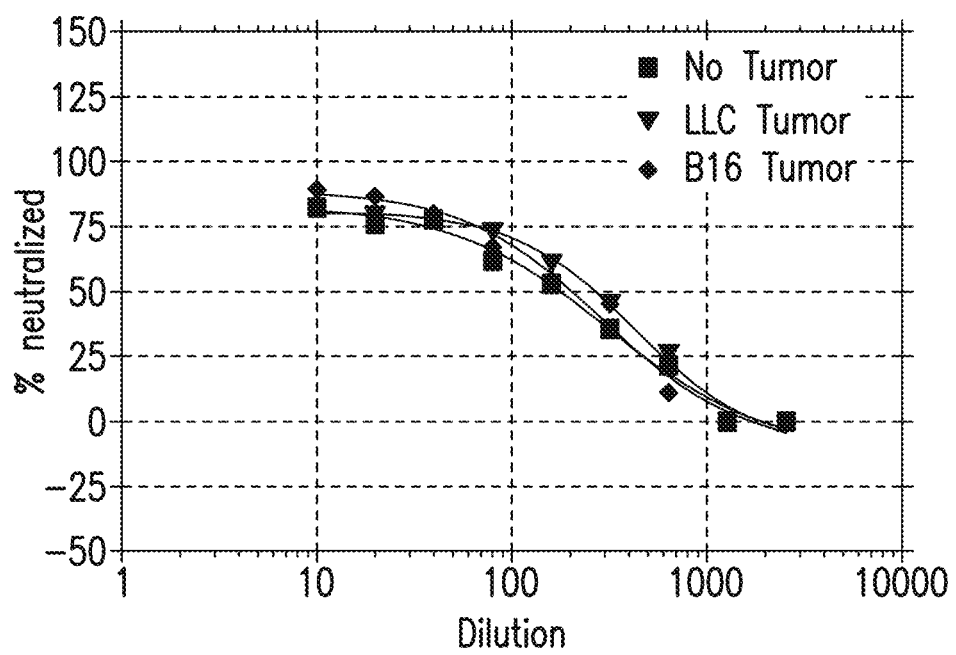

FIG. 14A-B. (A) Mice bearing no tumor or subcutaneous tumors derived from LLC or B16 cells (50-100 mm³) were treated within a single intravenous injection of $1 \times 10^7$ PFU of WR.TK-. Mice (n=3 per group and time) were sacrificed at indicated times and spleens and serum recovered. Splenocytes were rapidly fixed and permeabilized (according to our previously published protocol) and then stained for phosflow to detect activation of signaling pathways. This was performed for Regulatory T-cells (CD3+CD4+CD8-FoxP3+CD25+), with pSTAT5, pS6 and Ki67 analyzed; for CD4 T-cells (CD3+CD4+CD8-FOXP3-), with pS6, Ki67, CD44 and CD62L analyzed; and for CD8 T-cells (CD3+CD4-CD8+FoxP3-), with pS6, Ki67, CD44 and CD62L analyzed. (B) Anti-viral neutralizing antibody levels were also examined in the serum.

Figure 15A:
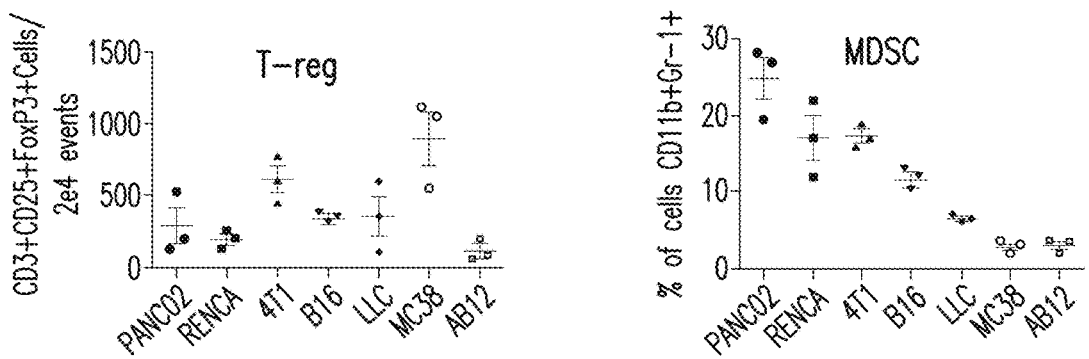
Figure 15B:
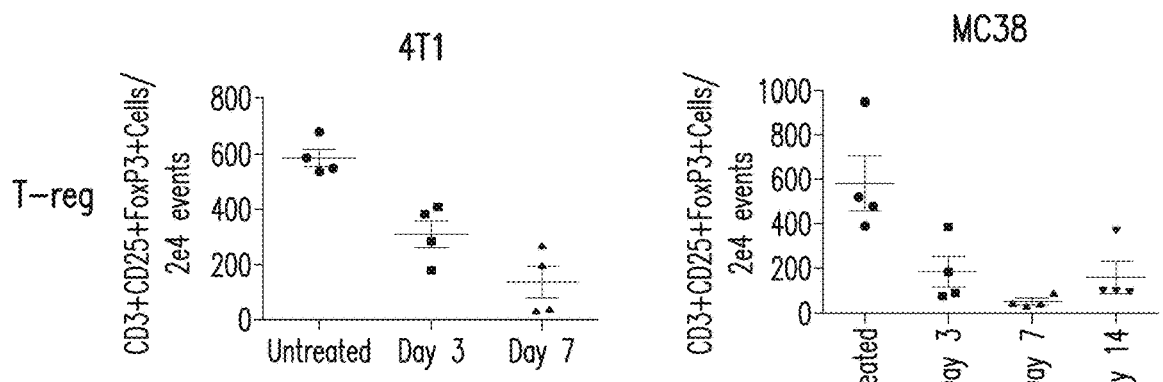
Figure 15B:
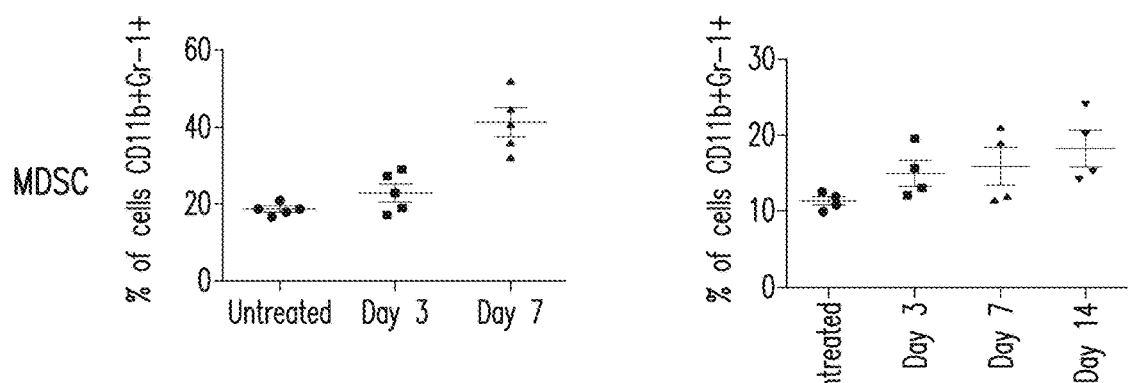
Figure 15B:
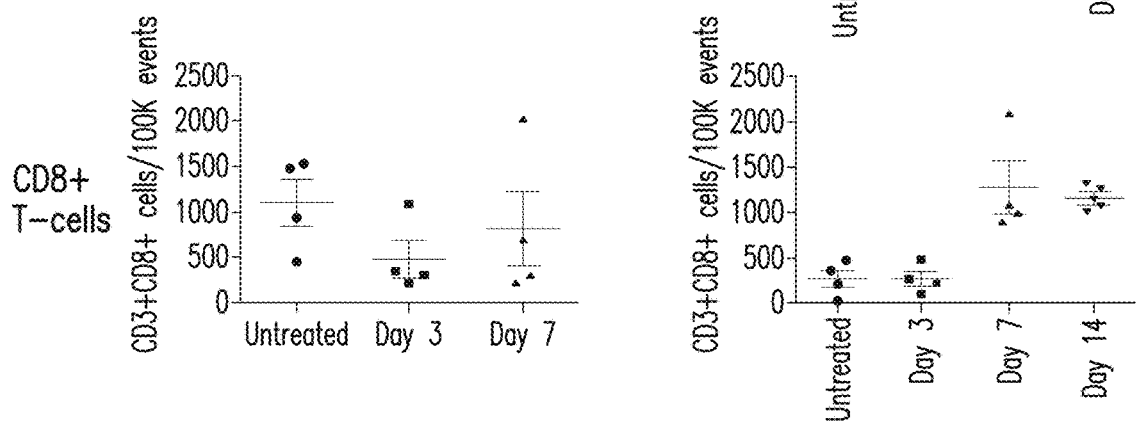

FIG. 15A-B. (A) Concentration of regulatory T-cells and MDSC cells in various mouse tumor models infected with TK-. (B) Concentration of regulatory T-cells, MDSC cells and CD8+ T-cells in 4T1 and MC38 mouse tumor models infected with TK-.

FIG. 16A-B. (A) Gating strategies are shown for detection of MDSC (left) and T-cells and T-regs (right) for splenocytes or cells recovered from disaggregated tumors. (B) The levels of MDSC and T-reg in the spleen are shown for mice bearing different tumors.

Figure 17A:
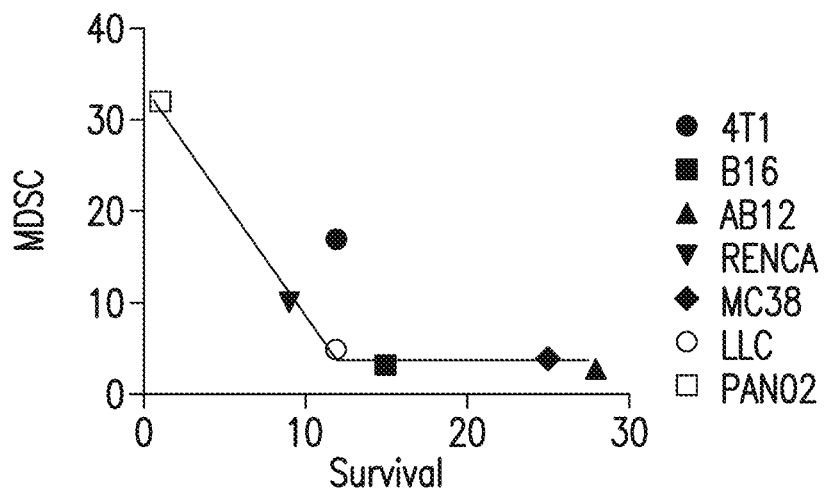
Figure 17B:
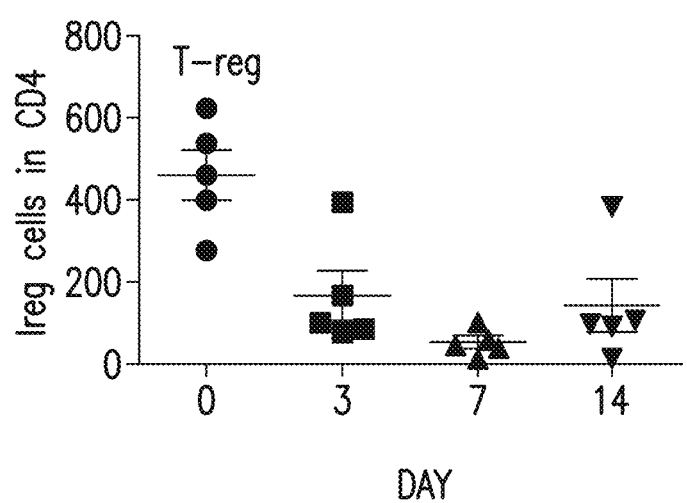
Figure 17C:
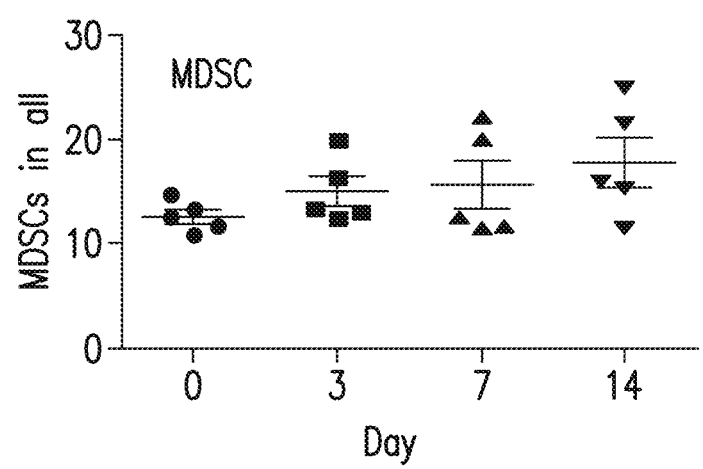

FIG. 17A-C. (A) TK-vaccinia strain displays a very poor ability to increase median survival (relative to PBS control) in mouse tumor models that display high levels of MDSC at baseline. Also, TK-viral therapy can reduce levels of (B) T-reg in treated tumors, but has no impact on (C) MDSC levels.

Figure 18:
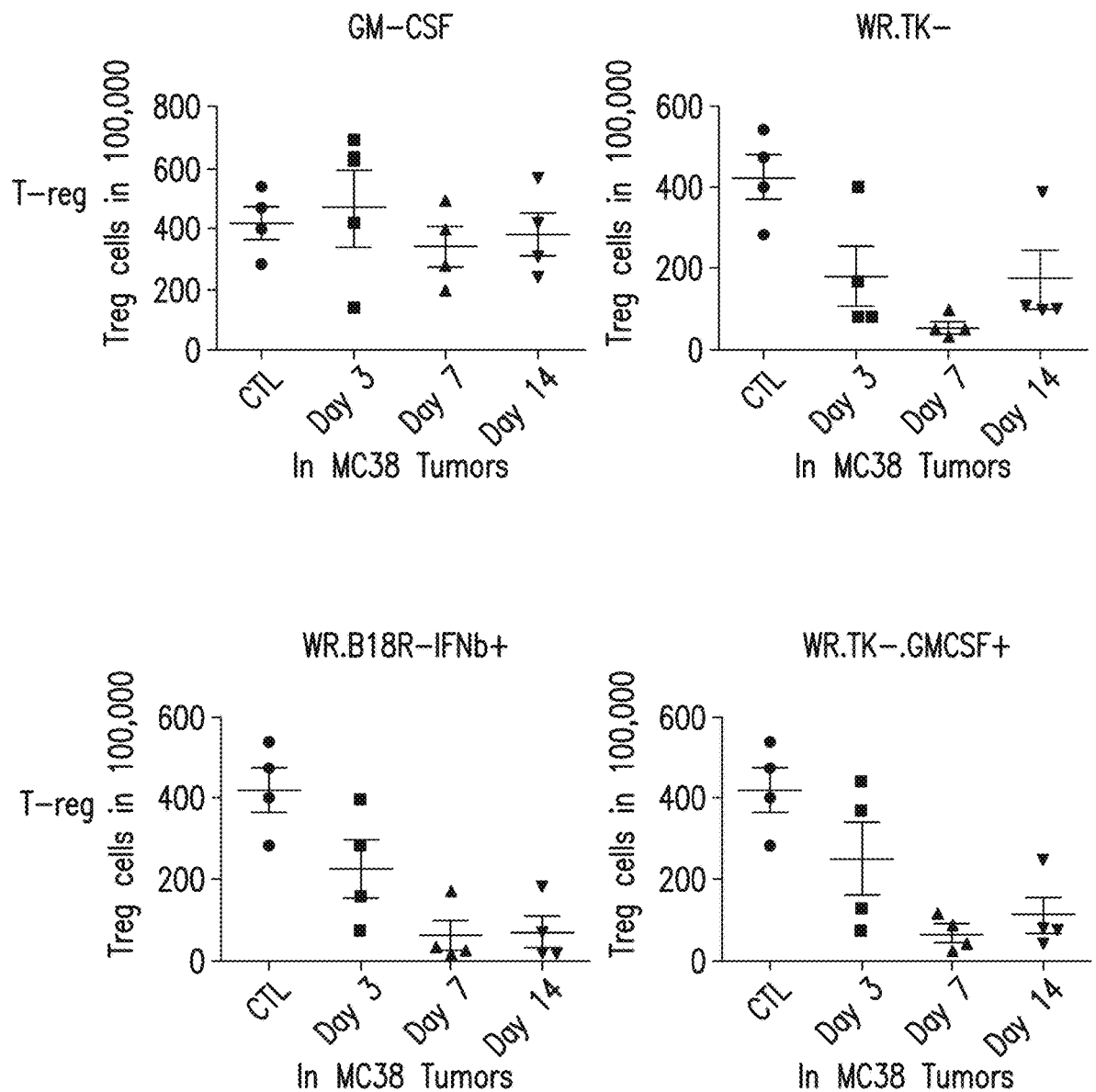
Figure 18:
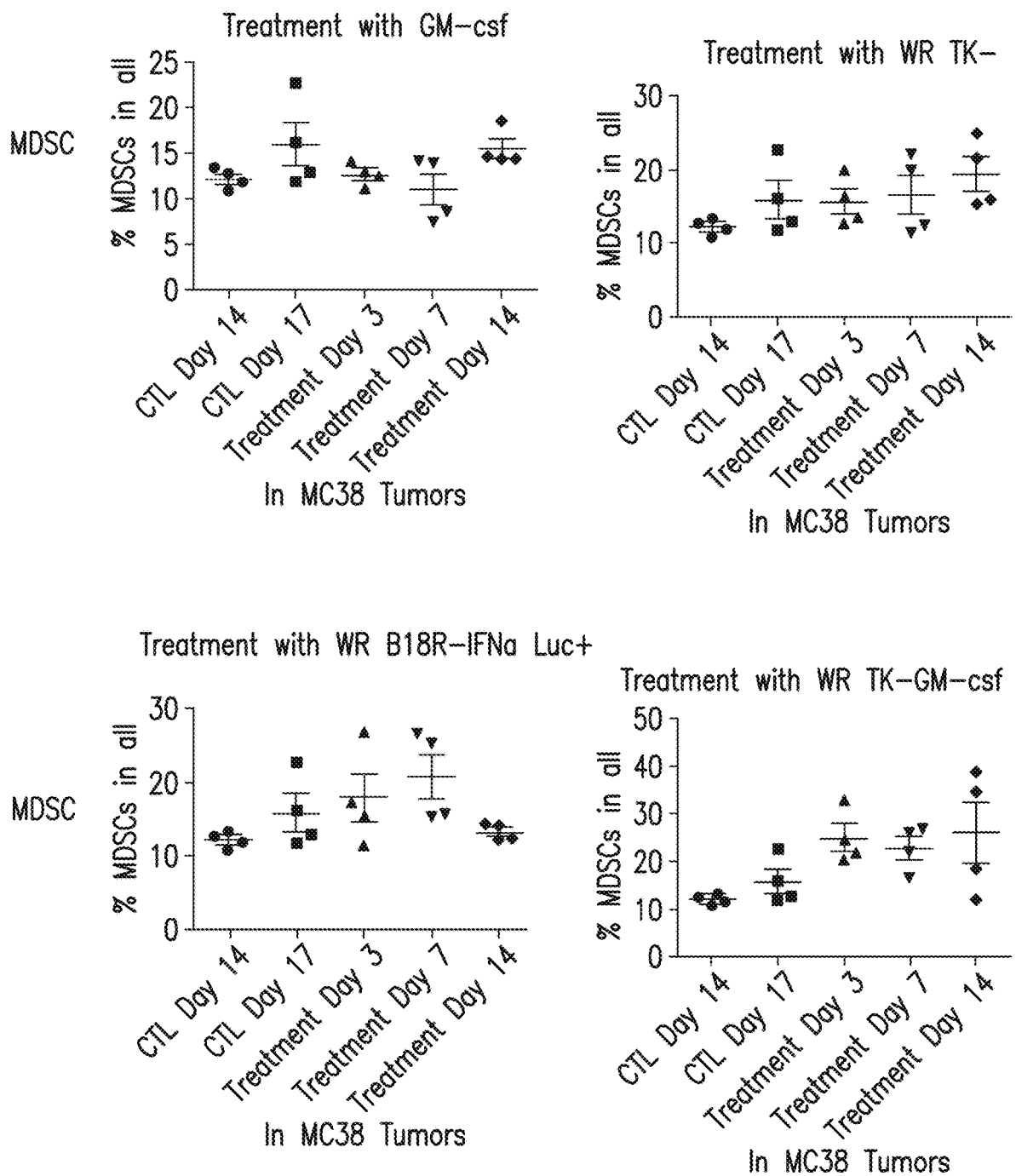
Figure 18:
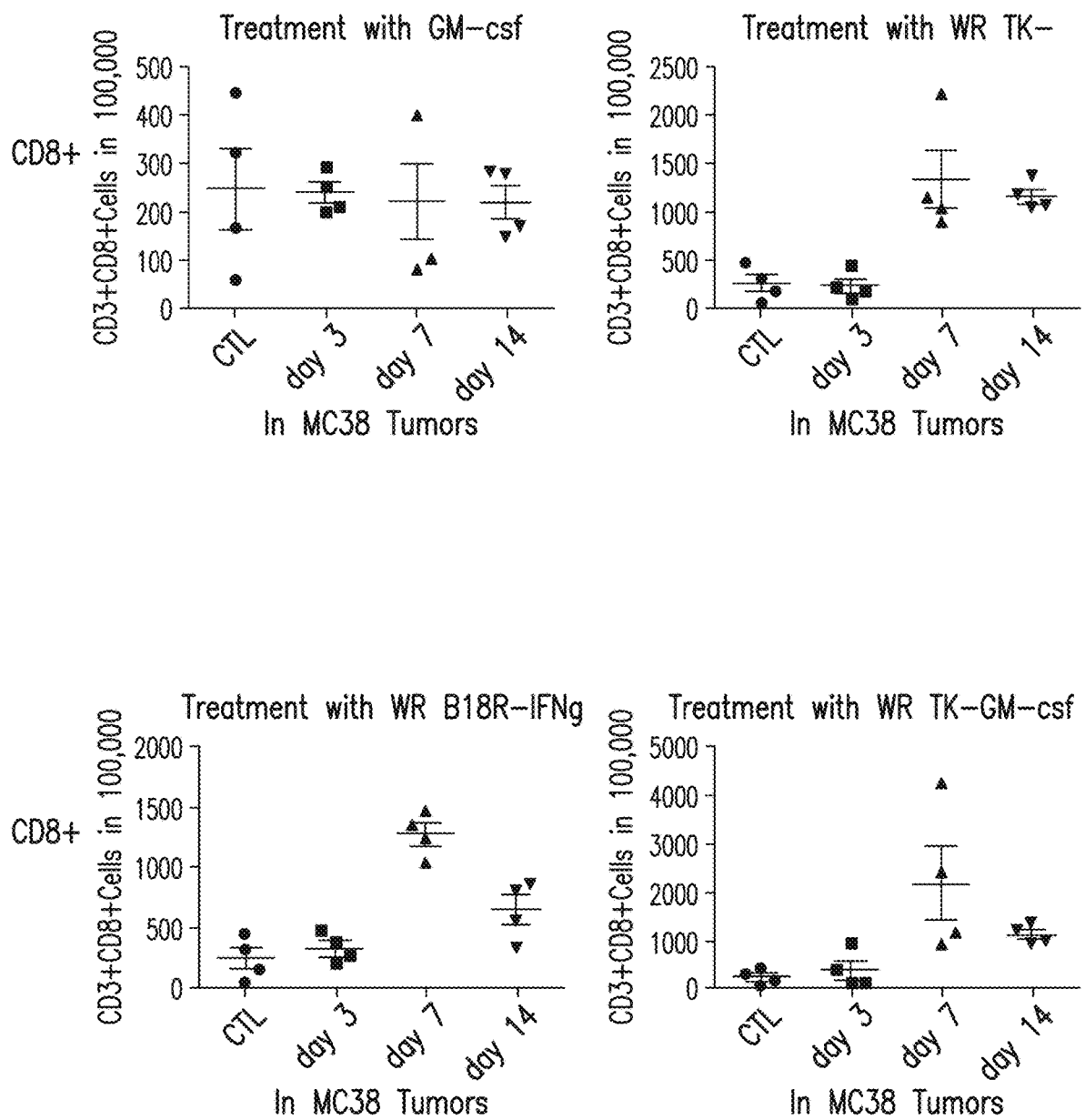

FIG. 18. Analysis of the immune response in mice implanted with MC38 tumor cells upon treatment with the immunogenic vaccinia strains, GM-CSF, WR.TK-GM-CSF, WR.BI8R-IFNα+, WR.B18R-IFNβ+ and WR.B18R-IFNγ+ in comparison to the immune response elicited by TK-infection.

Figure 19:
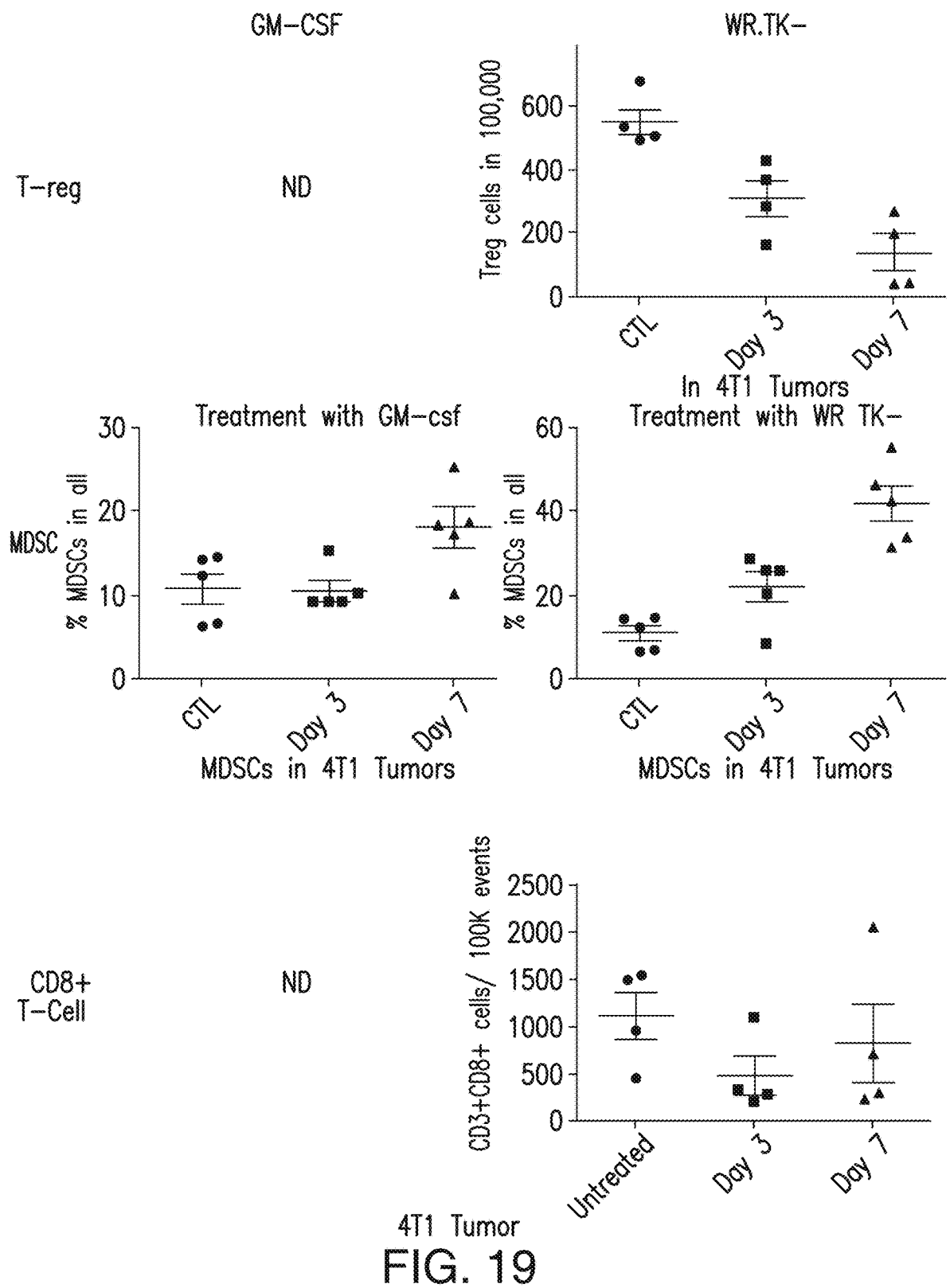
Figure 19:
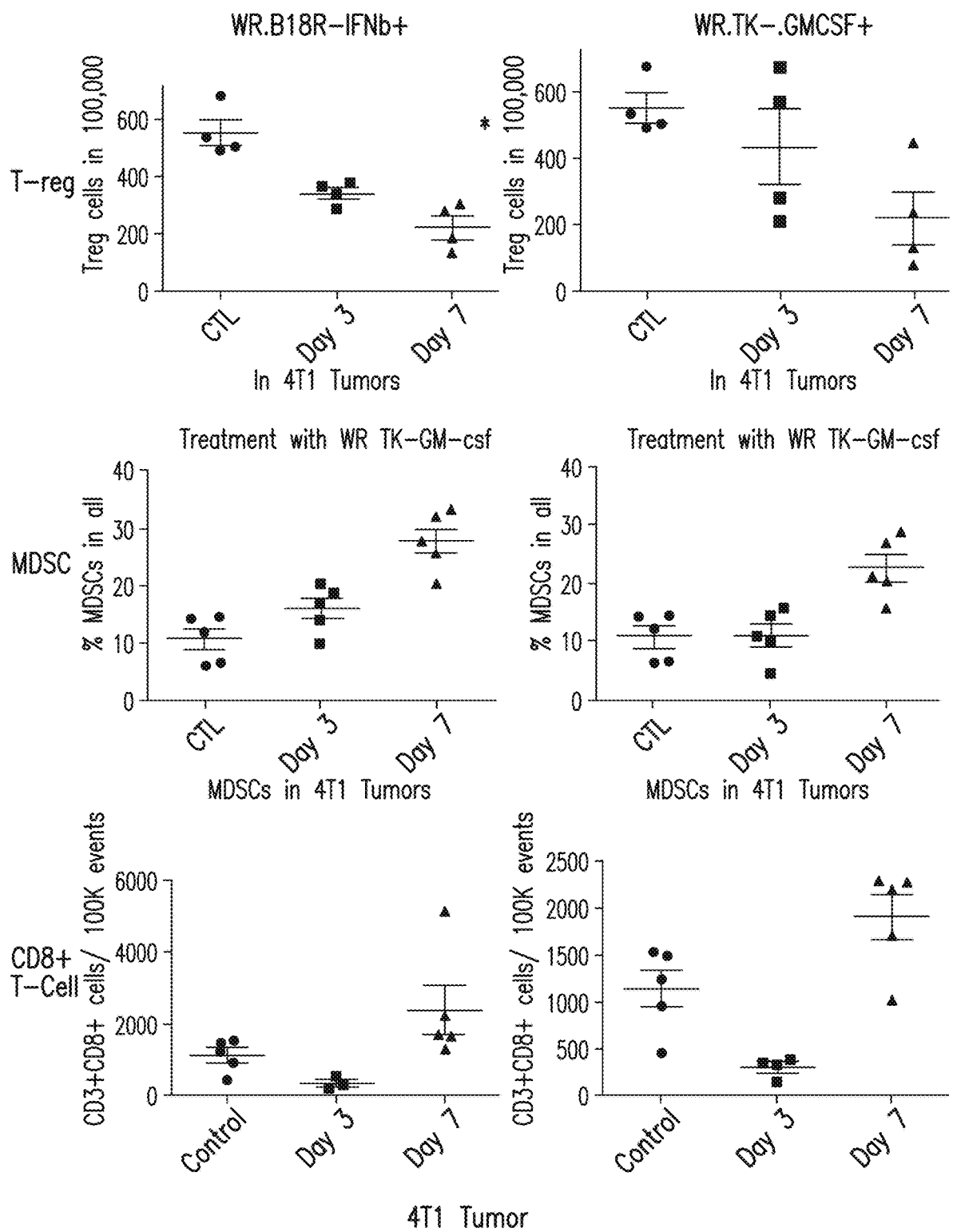

FIG. 19. Analysis of the immune response in mice implanted with 4T1 tumor cells upon treatment with the immunogenic vaccinia strains, GM-CSF, WR.TK-GMCSF and WR.B18R-IFNβ+ in comparison to the immune response elicited by TK-infection.

Figure 20:
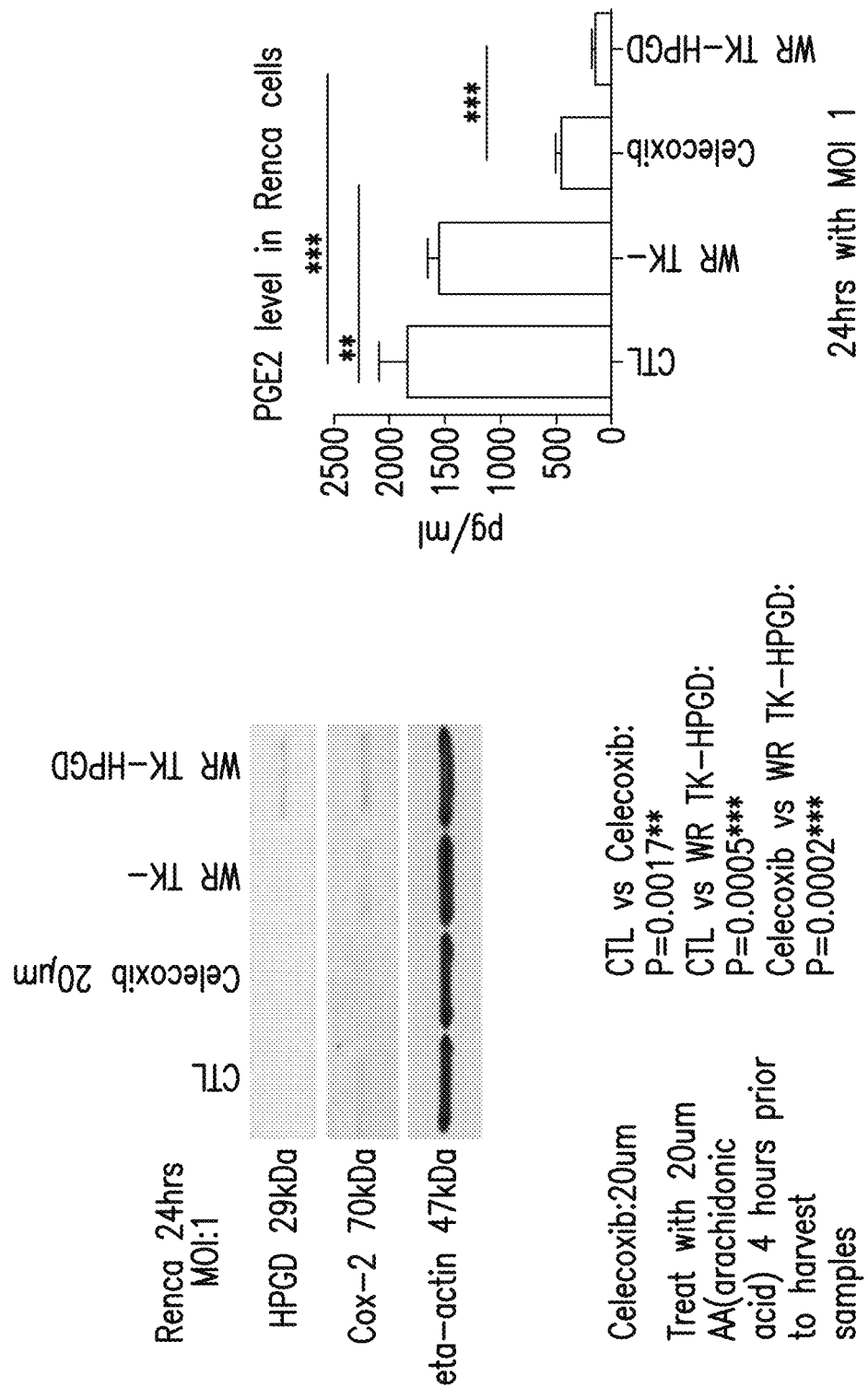

FIG. 20. Expression of COX2 and HPGD upon expression of WR-TK-HPGD or treatment of the Cox 2 inhibitor, Celecoxib. Beta-actin was detected as a loading control.

Expression of PGE2 was determined in Renca cells upon infection with WR-TK-HPGD or WR TK- or treatment of Celecoxib.

FIG. 21A-D. HPGD expression from oncolytic vaccinia reduced MDSC in the tumor and sensitizes resistant tumors to viral therapy. (A) Effect of HPGD expression on T-reg and MDSC levels in the tumor. Mice bearing Renca tumors were treated with intratumoral, low dose ($1 \times 10^7$ PFU) injection of indicated virus and mice sacrificed at indicated times, tumors recovered, disaggregated and analyzed by flow cytometry as before. HPGD expression reduces MDSC and T-reg levels (*p<0.05 compared to control). (B) Enhanced therapeutic activity of WR.TK-.HPGD+. Mice bearing subcutaneous Renca or MC38 tumors were treated with a single intratumoral injection of PBS or $1 \times 10^7$ PFU or WR.TK- or WR.TK-HPGD+ and subsequent tumor growth followed by caliper measurement (n=15 per group; WR.TK-HPGD+ significantly (p<0.05) delayed tumor growth from day 3 (RENCA) or day 7 (MC38) compared WR.TK- and resulted in 3 complete responses for RENCA and 2 for MC38. No mice from any other group displayed a CR). (C) Comparison of tumor growth and viral gene expression for WR.TK-.HPGD+ treatment. Tumor growth for individual mice with Renca tumors and treated with WR.TK-HPGD+ are plotted, compared to PBS control (grey bar) and divide into good (solid line) and best (dashed line) responders. The bioluminescence signal (viral gene expression) from the tumor at day 1 and 5 were normalized to tumor volume and shown for both good and best responders. (D) HPGD expression does not reduce viral gene expression. Viral luciferase gene expression from within the tumor at 24 h after treatment with WR.TK- or WR.TK-HPGD+ is shown.

Figure 22:
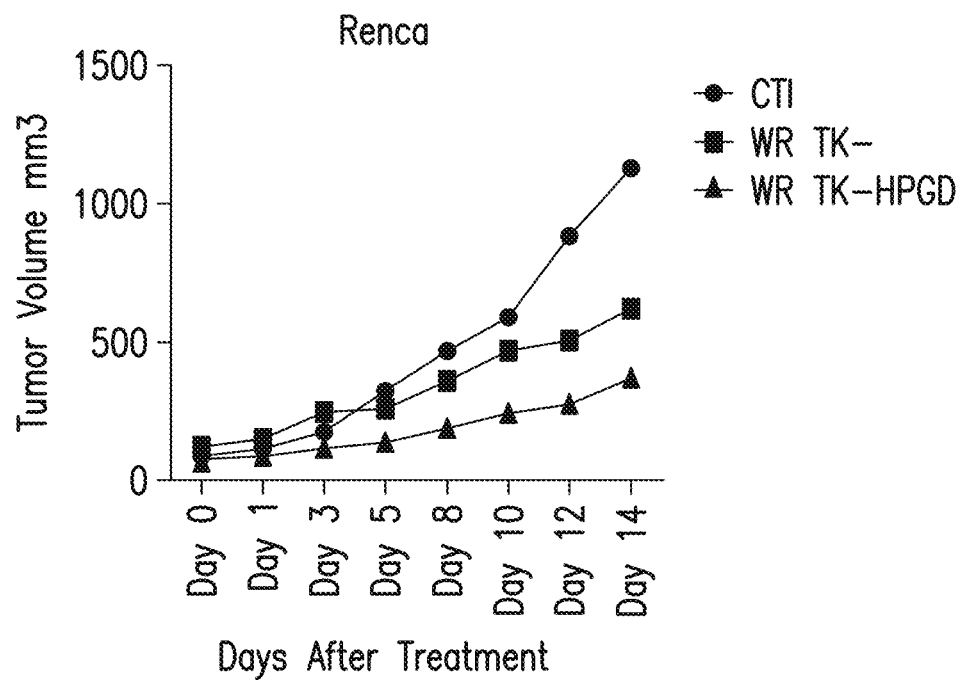
Figure 23A:
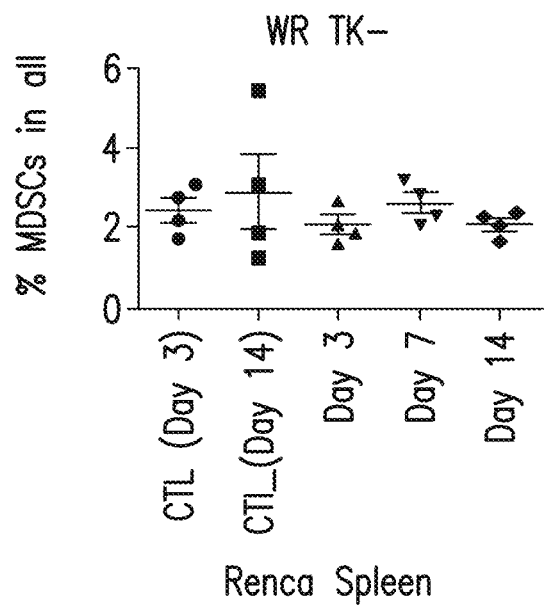
Figure 23B:
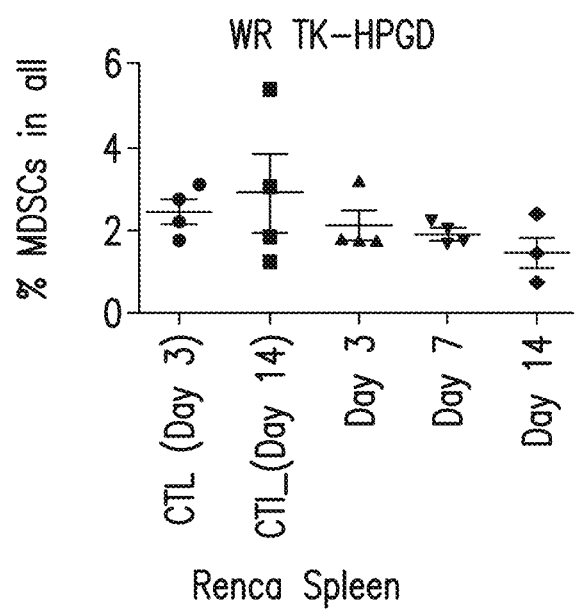
Figure 23C:
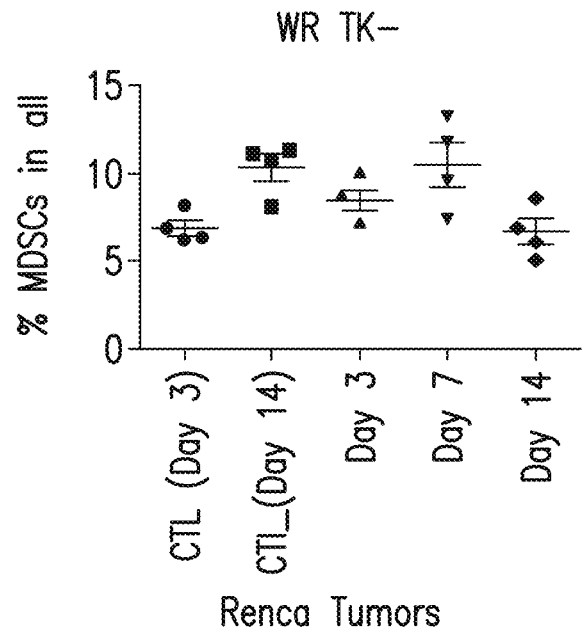
Figure 23D:
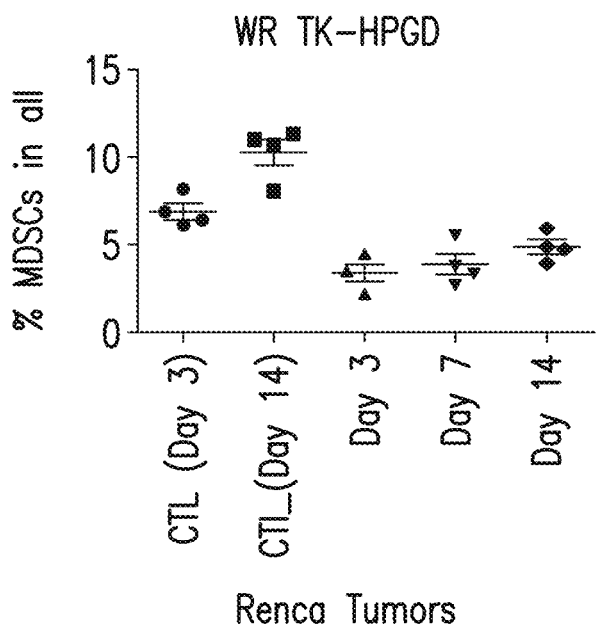

FIG. 22. Tumor volume as a function of days after treatment with PBS control (CTL; circle), thymidine kinase negative Western Reserve VV (WR TK-; square) or thymidine kinase (TK) negative Western Reserve VV carrying HPGD (WR TK-HPGD, triangle) (HPGD is murine equivalent of human 15-PGDH protein).

FIG. 23A-D. Percent MDSCs in (A) spleen of mice infected with WR TK-; (B) spleen of mice infected with WR TK-HPGD; (C) tumor of mice infected with WR TK-; and (D) tumor of mice infected with WR TK-HPGD.

FIG. 24A-D. HPGD expression enhanced the immune response and alters immune cell trafficking to the tumor. (A) Cytokine and chemokine profiles in the tumor after different treatments. Mice bearing RENCA tumors were treated as indicated with $1 \times 10^7$ PFU of different viral strains IT and sacrificed after 3 days. Tumor homogenates were run on Luminex assays to quantify different cytokines and chemokines (*p<0.05). (B) Anti-tumor CTL response is increased with HPGD expression. Splenocytes collected form RENCA tumor bearing mice 7 days after the indicated treatments were quantified for anti-tumor CTL response as determined by ELISPOT (*p<0.06). (C) Systemic alterations in chemokine levels after different treatments. Serum collected from RENCA tumor bearing mice 3 days after the indicated treatments were quantified for chemokine levels by ELISA (p<0.05). (D) Activated immune cells preferentially target tumors infected with HPGD-expressing virus. Mice were implanted with bilateral RENCA tumors and when these reached 50-100 mm³, these were injected with $1 \times 10^7$ PFU of WR.TK- on one flank and WR.TK-HPGD+ on the opposite flank, after 24 h $1 \times 10^7$ activated and Cy5.5 labeled NK T (CIK) cells were delivered via tail vein injection. 24 h later mice were imaged for bioluminescence (Viral gene expression) and fluorescence (NK T cell trafficking to tumors) (*p<0.05). A representative example of fluorescence imaging is shown.

Figure 25:
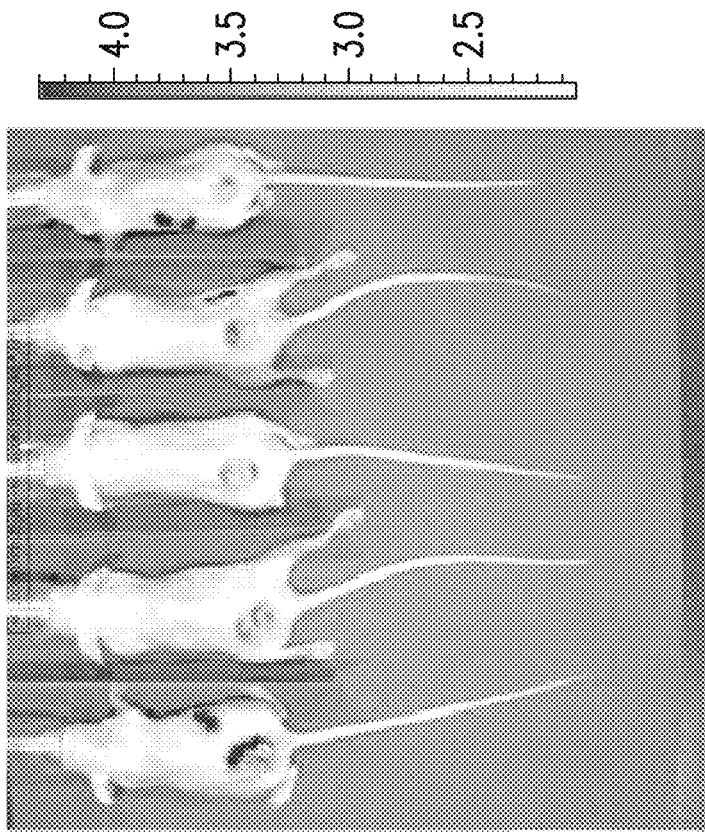
Figure 25:
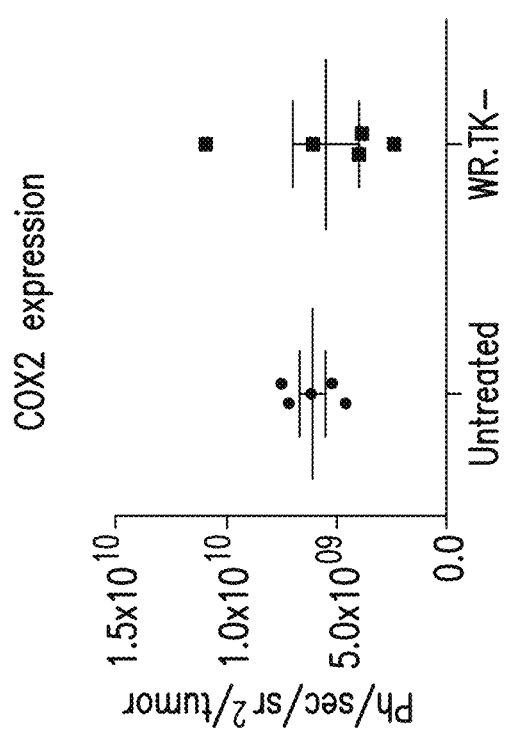

FIG. 25. COX2 expression in tumors infected with WR.TK-compared to untreated tumors.

Figure 26A:
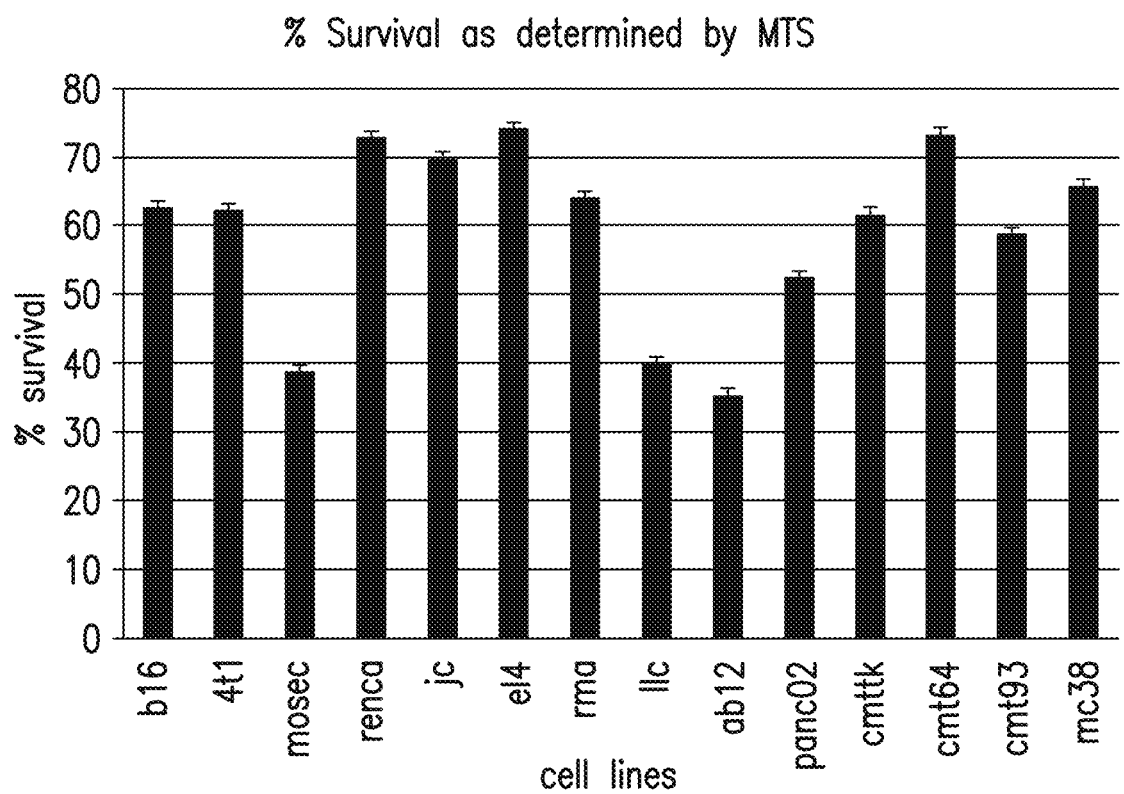
Figure 26B:
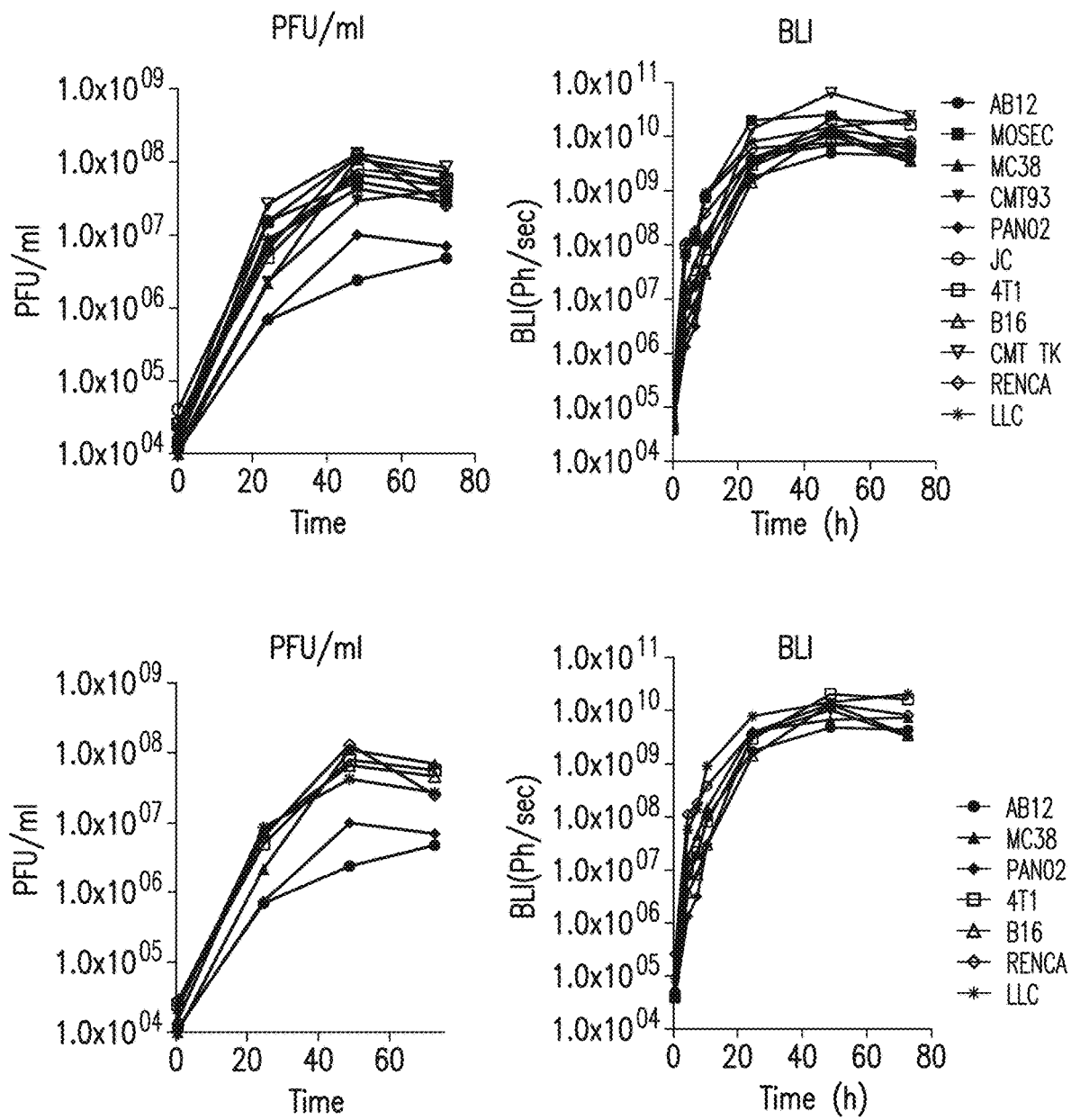

FIG. 26A-B. (A) Survival of various cells lines upon infection with TK-. (B) Viral production and gene expression of TK- in various tumor cells lines.

Figure 27:
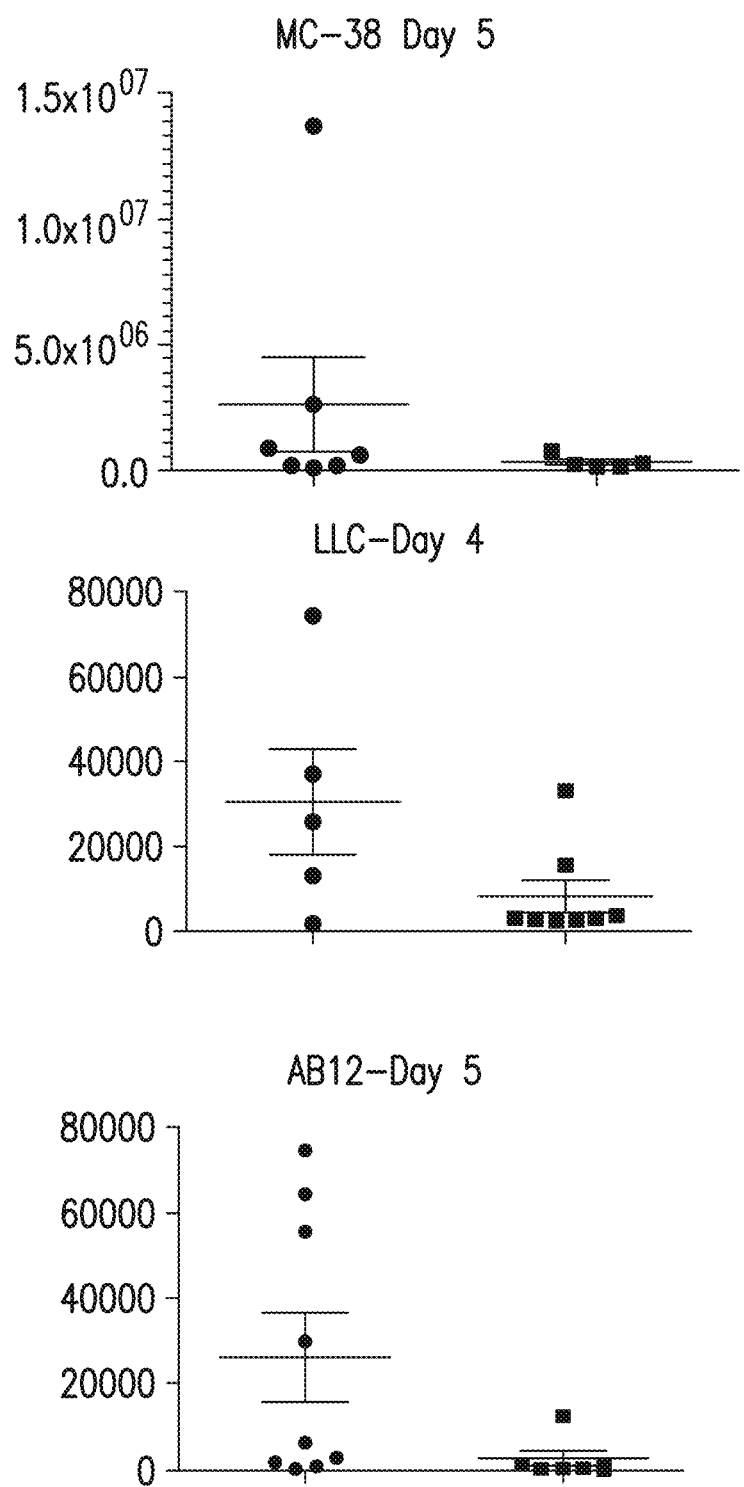

FIG. 27 depicts viral gene expression of TK-infected MC-38, LLC and AB12 mouse tumor models after day 4 or day 5 of infection.

Figure 28:
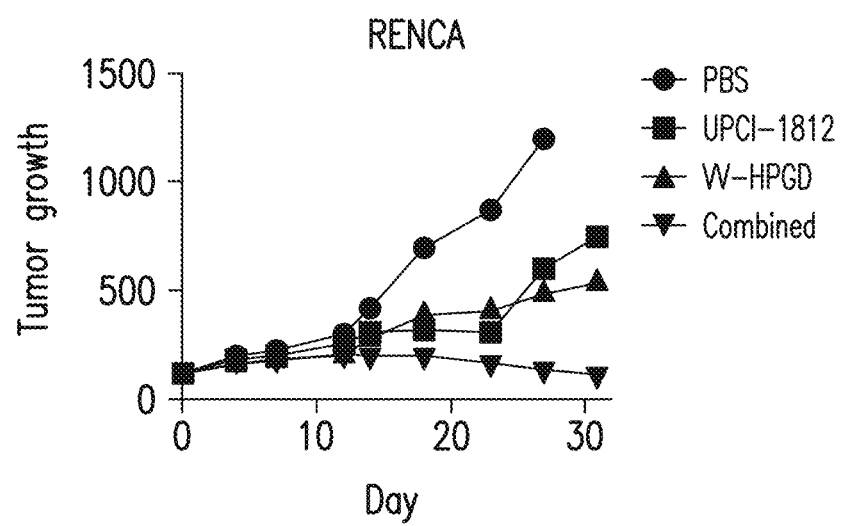

FIG. 28. Tumor growth as a function of days after treatment with PBS or infection with deglycosylated WR.TK-TRIF+-(UPCI-1812), Western Reserve TK- carrying HPGD (VV-HPGD) or UPCI-1812 combined with HPGD expression.

Figure 29:
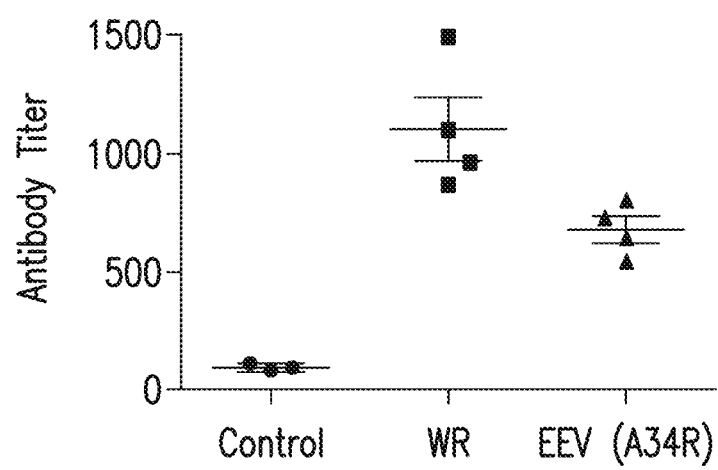

FIG. 29. Enhanced EEV production (A34R mutation K151E) leads to reduced anti-viral neutralizing antibody (14 days after IP delivery of WR or EEV).

Figure 30:
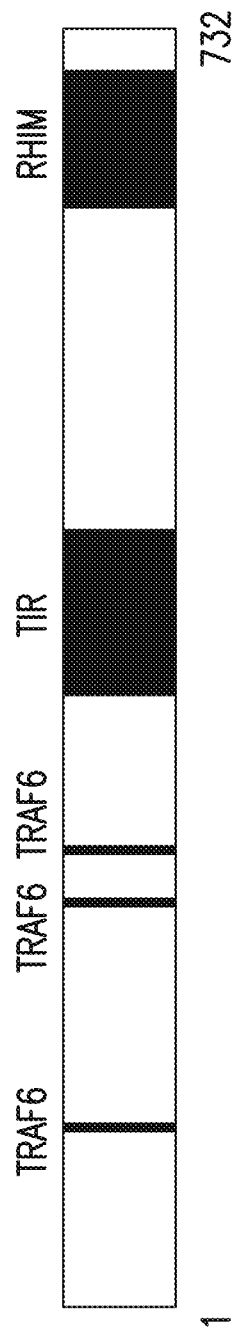

FIG. 30. TRIF domains. In the human TRIF amino acid sequence there are three TRAF binding domains and the RHIM domain that binds RIP1.

5. DETAILED DESCRIPTION OF THE INVENTION

For clarity of description, and not by way of limitation, the detailed description of the invention is divided into the following subsections:
  (i) viral backbone mutations;
  (ii) modification of viral glycosylation;
  (iii) modification that promotes T cell response;
  (iv) modification that inhibits immunosuppression;
  (v) modification that enhances virus spread and activity;
  (vi) modified viruses;
  (vii) methods of treatment; and
  (viii) kits.

The term "homology" as used herein refers to the degree of homology between nucleic acid or amino acid sequences as determined using methods known in the art, for example, but not limited to, software such as BLAST or FASTA.

5.1 Viral Backbone Mutations

In certain non-limiting embodiments of the invention, a VV contains one or more mutations of its genome that favors replication of the virus in a cancer cell and/or increased induction of a Cytotoxic T-Lymphocyte (CTL) immune response. A mutation may be an insertion, deletion, or substitution of one or more nucleic acids of the native virus.

In particular non-limiting embodiments, the mutation results in decreased functional interleukin-18 binding protein ("IL-18BP") expression. As non-limiting examples, (i) the mutation may result in a protein with weaker binding to IL-18 than the native VV protein; (ii) the mutation may result in expression of a truncated protein with decreased or absent functional activity; or (iii) the mutation may delete the IL-18BP gene. In a specific non-limiting example, the mutation may be a C12L deletion (e.g., see Symons et al., 2002, J. Gen. Virol. 83:2833-2844). In certain embodiments, the C12L deletion can be a complete or partial deletion of C12L. For example, and not by way of limitation, a partial deletion of C12L can include a mutation that results in the deletion of at least about 10%, at least about 20%, at least about 30% or at least about 40% or more of the amino acid sequence of the C12L protein.

In further non-limiting embodiments, the viral backbone may contain, separately or in addition to one or more of the mutations in (including deletion of) a nucleic acid encoding IL-18BP described above, a mutation in nucleic acid encoding B8R (IFN gamma binding protein; e.g., see Symons et al., 1995, Cell. 81(4):551-60), B18R (type I IFN binding protein; e.g., see Colamonici et al., 1995, J. Biol. Chem. 270(27):15974-8), A35R (inhibitor of MHC II presentation; e.g., see Rehm et al., 2010, Virology. 397(1):176-86 and Roper et al., 2006, J. Virol. 80(1):306-13), B15R (IL-1β binding protein; e.g., see Alcami et al., 1992, Cell. 71(1): 153-67), Chemokine binding proteins (B29R, G3R, H5R), STAT1 inhibitor (H1L); dsRNA or PKR inhibitors such as E3L (e.g., see Chang et al., 1992, Proc. Natl. Acad. Sci. 89(11):4825-9) or K3L (e.g., see Davies et al., 1993, J. Virol. 67(3):1688-92 and Langland et al., 2002, Virology. 299(1): 133-41); Bcl-2 like proteins (such as N1, N2, B14, F1, C6, A46 and K7), or a combination thereof.

5.2 Modification of Viral Glycosylation

In certain non-limiting embodiments of the invention, a VV is treated with an agent that modifies glycosylation. For example, a cell producing the VV may be administered a glycosylation inhibitor and/or cultured in the presence of a glycosylation inhibitor or a VV may be treated with an agent that reduces or removes or modifies glycosylation. In certain embodiments, a VV can be subjected to acid treatment to reduce glycosylation of the virus. In certain embodiments, the VV of the present invention can be produced in a cell line that does not have glycosylation activity, e.g., due to mutations in one or more glycosylation enzymes.

In certain embodiments, the VV treated with an agent that reduces or removes or modifies glycosylation, e.g., a deglycosylated virus, can have less than about 90%, less than about 80%, less than about 70%, less than about 60%, less than about 50%, less than about 40%, less than about 30%, less than about 20% or less than about 10% of the glycosylation of a VV that was not treated with agent that modifies glycosylation.

In particular non-limiting embodiments, a VV of the present invention can be treated with a sialidase enzyme which reduces or removes sialic acid residues from the viral surface (e.g., envelope). In non-limiting embodiments, the VV is treated with a sialidase enzyme prior to administration to a subject. In a specific non-limiting embodiment, the sialidase enzyme is Sialidase A enzyme (Glyko Sialidase A, Code WS0042) for example as part of the Glycopro Enzymatic Deglycosylation kit (Product Code: GK80110, Prozyme). In certain embodiments, the VV can be treated with Sialidase A in combination with N- and O-glycanases. Other enzymes that remove sialic acid or that cleave glycosyl residues from the virus may also be used according to the invention, including but not limited to neuraminidases, PNGases (e.g., PNGase A or PNGase F), β1-4 galactosidase, β-N-acetylglucosaminidase, or the use of chemical treatments such as b-elimination or alkali or hydrazinoyls.

Without being bound to any particular theory, it is believed that reduction of glycosylation, for example by sialidase treatment of the vaccinia virus, reduces TLR2 activation and thereby delays systemic immune activation during the period of viral delivery and/or reduces the production of anti-viral neutralizing antibodies.

5.3 Modifications that Promote T Cell Response

In certain non-limiting embodiments of the invention, a VV is modified to include one or more nucleic acids encoding a peptide or protein which promotes a T cell response. In certain embodiments, the peptide or protein which promotes a T-cell response can promote the expression of one or more proinflammatory cytokines. For example, and not by way of limitation, proinflammatory cytokines can include IL-4, IL-5, IL-6, IL-12, IL-15, IL-18, IL-21, IFN-α, IFN-β, IFN-γ, CCL5 and IP-10.

Non-limiting examples of a peptide or protein which promotes a T cell response include Toll/IL-1R domain-containing adapter inducing IFN-β ("TRIF") or a functional domain thereof. In certain non-limiting embodiments, the nucleic acid may encode a human TRIF having an amino acid sequence as set forth in UniProtKB No. Q8IUC6, or an amino acid sequence at least about 90 percent, at least about 95 percent or at least about 98 percent homologous thereto, or a murine TRIF having an amino acid sequence as set forth in UniProtKB No. Q80UF7, or an amino acid sequence at least about 90 percent, at least about 95 percent or at least about 98 percent homologous thereto.

In certain non-limiting embodiments, the nucleic acid may encode one or more TRIF domains as depicted in FIG. 30. In certain embodiments, the nucleic acid encoding a peptide or protein that promotes a T cell response, e.g., TRIF, can be cloned into the locus of the thymidine kinase (TK) gene of the virus as depicted in FIG. 4A. The nucleic acid encoding a peptide or protein that promotes a T cell response can be operably linked to any promoter that can result in expression of the nucleic acid. As used herein, "operably linked" means that a promoter is in a correct functional location and/or orientation in relation to a nucleic acid sequence to control transcriptional initiation and/or expression of that sequence. In certain embodiments, the promoter is a vaccinia promoter and/or a synthetic vaccinia promoter. In certain embodiments, the promoter is the synthetic vaccinia promoter pSE/L. In certain embodiments, the nucleic acid encoding a peptide or protein that promotes a T cell response is operably linked to the viral p7.5 promoter.

In other non-limiting embodiments, the nucleic acid may encode granulocyte-macrophage colony stimulating factor ("GM-CSF"), IL-12, IFN-γ or IL-18. In certain embodiments more than one such nucleic acid may be incorporated into VV.

5.4 Modifications that Inhibit Immunosuppression

In certain non-limiting embodiments of the invention, a VV is modified to include one or more nucleic acid encoding a peptide or protein or ribonucleic acid or micro-RNA which inhibits or reduces immunosuppression. Non-limiting examples of measures of immunosuppression include: the level of myeloid derived suppressor cells ("MDSC"); the level of M2 macrophages; and the level of helper T cells versus suppressor regulatory T cells. In particular non-limiting embodiments, the nucleic acid encodes a peptide or protein or ribonucleic acid or micro-RNA that reduces prostaglandin E2 activity ("a PGE2 antagonist"). In specific non-limiting embodiments, the nucleic acid encodes a peptide and/or protein that is a PGE2 antagonist (as that term is used herein) that degrades PGE2. In a specific non-limiting example, the protein that degrades PGE2 is 15-PGDH (human) or HPGD (mouse). For example, and not by way of limitation, 15-PGDH may have an amino acid sequence as set forth in UniProtKB No. P15428, or an amino acid sequence at least about 90 percent, at least about 95 percent or at least about 98 percent homologous thereto, and a nucleic acid encoding 15-PGDH may have a nucleic acid sequence as set forth in GenBank Accession No. U63296.1, or a nucleic acid sequence at least about 90 percent, at least about 95 percent or at least about 98 percent homologous thereto. In further non-limiting embodiments, a nucleic acid encoding a secreted and solubilized version of the extracellular receptor for PGE2 may be included in the VV, for example nucleic acid encoding EP1, EP2, EP3 and/or EP4, where EP3 and 4 are higher affinity. In certain embodiments, the one or more peptides or proteins which inhibits or reduces immunosuppression can result in the reduced expression of one or more suppressive chemokines such as, but not limited to, CXCL12. In certain embodiments, the one or more peptides or proteins which inhibits or reduces immunosuppression can result in the increased expression of one or more immune activating chemokines such as, but not limited to, CXCL9, CXCL10 and CCL5.

In certain embodiments, the nucleic acid encoding a PGE2 antagonist can be cloned into the locus of the thymidine kinase (TK) gene of the virus. The nucleic acid encoding a PGE2 antagonist peptide or protein can be operably linked to any promoter that can result in expression of the nucleic acid. In certain embodiments, the nucleic acid encoding a PGE2 antagonist peptide or protein is operably linked to the viral p7.5 promoter. In certain embodiments, the promoter is a vaccinia promoter and/or a synthetic vaccinia promoter. In certain embodiments, the promoter is the synthetic vaccinia promoter pSE/L. In certain embodiments, the virus can include a nucleic acid encoding a PGE2 antagonist and a nucleic acid encoding a peptide or protein that promotes a T cell response that are both operably linked to a promoter, e.g., the viral p7.5 promoter, and cloned into the locus of the thymidine kinase (TK) gene of the virus.

In further non-limiting embodiments, an immunooncolytic virus of the invention may be administered together with an agent that inhibits or reduces MDSC, including, for example but not by way of limitation, an antibody that targets a surface marker of MDSC such as an anti-CD33 antibody or variable region thereof; an anti-CD11b antibody or variable region thereof; a COX2 inhibitor, e.g., celecoxib; sunitinib and/or all trans retinoic acid (e.g., see Najjar and Finke, 2013, Frontiers in Oncology, 3(49) 1-9).

5.5 Modifications that Enhance Virus Spreading and Activity

In certain non-limiting embodiments of the invention, a VV is modified to enhance the spread and/or activity of virus. In particular non-limiting embodiments, a VV is modified to increase the amount of the extracellular enveloped form of the virus that is produced, for example by introducing one or more of the following mutations: A34R Lys151 to Glu; complete or partial deletion of B5R; mutation/deletion of A36R and/or mutation/deletion of A56R. In certain embodiments, a VV is modified to include a complete or partial deletion of B5R.

5.6 Modified Viruses

In non-limiting embodiments, the present invention provides for an immuno-oncolytic VV comprising one or more, or two or more, or three or more, or four or more, of the following modifications, as described in the sections above:
(i) a viral backbone mutation;
(ii) a modification of viral glycosylation;
(iii) a modification that promotes T cell response;
(iv) a modification that inhibits immunosuppression; and/or
(v) a modification that enhances virus spreading and activity.

In non-limiting embodiments, the present invention provides for a VV comprising a modification of viral glycosylation and one or more of the following modifications, as described in the sections above:
(i) a viral backbone mutation;
(ii) a modification that promotes T cell response;
(iii) a modification that inhibits immunosuppression; and/or
(iv) a modification that enhances virus spreading and activity.

In non-limiting embodiments, the present invention provides for a VV which is treated with an agent that reduces the amount of glycosylation (e.g., sialylation) prior to administration to a host and comprises or carries or contains one or more of the following modifications, as described in the sections above:
(i) a viral backbone mutation;
(ii) a modification that promotes T cell response;
(iii) a modification that inhibits immunosuppression; and/or
(iv) a modification that enhances virus spreading and activity.

In non-limiting embodiments, the present invention provides for a VV that has reduced glycosylation (e.g., sialylation) relative to unmodified virus and comprises or carries or contains one or more of the following modifications, as described in the sections above:
(i) a viral backbone mutation;
(ii) a modification that promotes T cell response;
(iii) a modification that inhibits immunosuppression; and/or
(iv) a modification that enhances virus spreading and activity.

In non-limiting embodiments, the present invention provides for a VV that is treated with an agent that reduces the amount of glycosylation prior to administration to a host or that otherwise has reduced glycosylation relative to unmodified virus, i.e., a deglycosylated virus.

In non-limiting embodiments, the present invention provides for a VV that is treated with sialidase prior to administration to a host or that otherwise has reduced sialic acid residues relative to unmodified virus.

In non-limiting embodiments, the present invention provides for a VV that comprises or carries or contains a nucleic acid encoding TRIF.

In non-limiting embodiments, the present invention provides for a VV that comprises or carries or contains a nucleic acid encoding a PGE2 antagonist (e.g., 15-PGDH or HPGD).

In non-limiting embodiments, the present invention provides for a VV that comprises one or more modifications that enhance virus spreading and activity selected from the group of a A34R Lys151 to Glu mutation; complete or partial deletion of B5R; mutation/deletion of A36R and/or mutation/deletion of A56R.

In non-limiting embodiments, the present invention provides for a VV which comprises one or more virus backbone modification selected from the group of a mutation that reduces expression of functional IL-18BP (e.g., C12L deletion), B8R deletion, B18R deletion, A35R deletion, or a combination thereof.

In non-limiting embodiments, the present invention provides for a VV which is treated with an agent that reduces the amount of glycosylation prior to administration to a host or that otherwise has reduced glycosylation relative to unmodified virus and further comprises or carries or contains a nucleic acid encoding TRIF or a functional domain thereof.

In non-limiting embodiments, the present invention provides for a VV which is treated with an agent that reduces the amount of glycosylation (e.g., sialylation) prior to administration to a host or that otherwise has reduced glycosylation (e.g., reduced sialylation) relative to unmodified virus and further comprises or carries or contains a nucleic acid encoding a PGE2 antagonist (e.g., 15-PGDH or HPGD).

In non-limiting embodiments, the present invention provides for a VV which is treated with an agent that reduces the amount of glycosylation (e.g., sialylation) prior to administration to a host or that otherwise has reduced glycosylation (e.g., reduced sialylation) relative to unmodified virus and further comprises or carries or contains a nucleic acid encoding TRIF or a functional domain thereof and/or a nucleic acid encoding a PGE2 antagonist (e.g., 15-PGDH or HPGD).

In non-limiting embodiments, the present invention provides for a VV which is treated with an agent that reduces the amount of glycosylation (e.g., sialylation) prior to administration to a host or that otherwise has reduced glycosylation (e.g., reduced sialylation) relative to unmodified virus and further comprises one or more modifications that enhance virus spreading and activity selected from the group of a A34R Lys151 to Glu mutation; complete or partial deletion of B5R; mutation/deletion of A36R and/or mutation/deletion of A56R. In certain embodiments, the present invention provides for a deglycosylated VV which comprises a complete or partial deletion of B5R.

In non-limiting embodiments, the present invention provides for a VV which is treated with an agent that reduces the amount of glycosylation (e.g., sialylation) prior to administration to a host or that otherwise has reduced glycosylation (e.g., reduced sialylation) relative to unmodified virus and further comprises one or more virus backbone modification selected from the group of a mutation that reduces expression of functional IL-18BP (e.g., C12L deletion), B8R deletion, B18R deletion, A35R deletion, or a combination thereof. In certain embodiments, the present invention provides for a deglycosylated VV which comprises a C12L deletion.

In non-limiting embodiments, the present invention provides for a VV which is treated with an agent that reduces the amount of glycosylation (e.g., sialylation) prior to administration to a host or that otherwise has reduced glycosylation (e.g., reduced sialylation) relative to unmodified virus and further comprises one or more virus backbone modification selected from the group of a mutation that reduces expression of functional IL-18BP (e.g., C12L deletion), B8R deletion, B18R deletion, A35R deletion, or a combination thereof, and further comprises one or more modifications that enhance virus spreading and activity selected from the group of a A34R Lys151 to Glu mutation; complete or partial deletion of B5R; mutation/deletion of A36R and/or mutation/deletion of A56R. In certain embodiments, the present invention provides for a deglycosylated VV which comprises a C12L deletion and a B5R deletion.

In non-limiting embodiments, the present invention provides for a VV which is treated with an agent that reduces the amount of glycosylation (e.g., sialylation) prior to administration to a host or that otherwise has reduced glycosylation (e.g., reduced sialylation) relative to unmodified virus and further comprises or carries or contains a nucleic acid encoding TRIF or a functional domain thereof and further comprises one or more virus backbone modifications selected from the group of a mutation that reduces expression of functional IL-18BP (e.g., C12L deletion), B8R deletion, B18R deletion, A35R deletion, or a combination thereof. In certain embodiments, the virus comprises the C12L deletion.

In non-limiting embodiments, the present invention provides for a VV which is treated with an agent that reduces the amount of glycosylation (e.g., sialylation) prior to administration to a host or that otherwise has reduced glycosylation (e.g., reduced sialylation) relative to unmodified virus and further comprises or carries or contains a nucleic acid encoding a PGE2 antagonist (e.g., 15-PGDH or HPGD) and further comprises one or more virus backbone modifications selected from the group of a mutation that reduces expression of functional IL-18BP (e.g., C12L deletion), B8R deletion, B18R deletion, A35R deletion, or a combination thereof.

In non-limiting embodiments, the present invention provides for a TK-VV which is treated with an agent that reduces the amount of glycosylation (e.g., sialylation) prior to administration to a host or that otherwise has reduced glycosylation (e.g., reduced sialylation) relative to unmodified virus and further comprises or carries or contains a nucleic acid encoding TRIF or a functional domain thereof and a nucleic acid encoding a PGE2 antagonist (e.g., 15-PGDH or HPGD), and further comprises one or more virus backbone modifications selected from the group of a mutation that reduces expression of functional IL-18BP (e.g., C12L deletion), B8R deletion, B18R deletion, A35R deletion, or a combination thereof.

In non-limiting embodiments, the present invention provides for a VV which is treated with an agent that reduces the amount of glycosylation (e.g., sialylation) prior to administration to a host or that otherwise has reduced glycosylation (e.g., reduced sialylation) relative to unmodified virus and further comprises or carries or contains a nucleic acid encoding TRIF or a functional domain thereof and further comprises one or more modifications that enhance virus spreading and activity selected from the group of a A34R Lys151 to Glu mutation; complete or partial deletion of B5R; mutation/deletion of A36R and/or mutation/deletion of A56R.

In non-limiting embodiments, the present invention provides for a VV which is treated with an agent that reduces the amount of glycosylation (e.g., sialylation) prior to administration to a host or that otherwise has reduced glycosylation (e.g., reduced sialylation) relative to unmodified virus and further comprises or carries or contains a nucleic acid encoding a PGE2 antagonist (e.g., 15-PGDH or HPGD) and further comprises one or more modifications that enhance virus spreading and activity selected from the group of a A34R Lys151 to Glu mutation; complete or partial deletion of B5R; mutation/deletion of A36R and/or mutation/deletion of A56R.

In non-limiting embodiments, the present invention provides for a VV which is treated with an agent that reduces the amount of glycosylation (e.g., sialylation) prior to administration to a host or that otherwise has reduced glycosylation (e.g., reduced sialylation) relative to unmodified virus and further comprises or carries or contains a nucleic acid encoding TRIF or a functional domain thereof and a nucleic acid encoding a PGE2 antagonist (e.g., 15-PGDH or HPGD), and further comprises one or more modifications that enhance virus spreading and activity selected from the group of a A34R Lys151 to Glu mutation; complete or partial deletion of B5R; mutation/deletion of A36R and/or mutation/deletion of A56R.

In non-limiting embodiments, the present invention provides for a VV which is treated with an agent that reduces the amount of glycosylation (e.g., sialylation) prior to administration to a host or that otherwise has reduced glycosylation (e.g., reduced sialylation) relative to unmodified virus and further comprises or carries or contains a nucleic acid encoding TRIF or a functional domain thereof and a nucleic acid encoding a PGE2 antagonist (e.g., 15-PGDH or HPGD), and further comprises one or more modifications that enhance virus spreading and activity selected from the group of a A34R Lys151 to Glu mutation; complete or partial deletion of B5R; mutation/deletion of A36R and/or mutation/deletion of A56R and comprises one or more virus backbone modifications selected from the group of a mutation that reduces expression of functional IL-18BP (e.g., C12L deletion), B8R deletion, B18R deletion, A35R deletion, or a combination thereof. In certain embodiments, the virus comprises the C12L deletion. In certain embodiments, the VV can comprise the C12L deletion and the B5R deletion.

The above-described modifications may be produced in a VV (vaccinia virus) that is known in the art. Non-limiting examples include the Western Reserve strain, Copenhagen strain; Wyeth (NYCBOH) strain; Tian Tian strain; or USSR strain (and see references 1 and 2, below). The base VV strain modified as set forth herein may itself comprise one or more mutation relative to its parent strain, for example, but not limited to, one or more of the following: deletion in TK (i.e., denoted herein as "TK-"); deletion in VGF; SPI-1 deletion; and/or SPI-2 deletion.

In certain non-limiting embodiments, the present invention provides for a VV with the following modifications:
(i) an envelope with reduced glycosylation (e.g., reduced sialylation) relative to an unmodified virus;
(ii) a nucleic acid encoding TRIF, or a functional domain thereof; and/or
(iii) a nucleic acid encoding 15-PGDH, or a functional domain thereof.

In non-limiting embodiments, the present invention provides for a VV with the following modifications:
(i) an envelope with reduced glycosylation (e.g., reduced sialylation) relative to an unmodified virus;
(ii) a nucleic acid encoding TRIF, or a functional domain thereof;
(iii) a nucleic acid encoding 15-PGDH, or a functional domain thereof; and/or
(iv) a C12L deletion.

In non-limiting embodiments, the present invention provides for a VV with the following modifications:
(i) an envelope with reduced glycosylation (e.g., reduced sialylation) relative to an unmodified virus;
(ii) a nucleic acid encoding TRIF, or a functional domain thereof;
(iii) a nucleic acid encoding 15-PGDH, or a functional domain thereof;
(iv) a C12L deletion; and/or
(v) a B5R deletion.

In certain non-limiting embodiments, the present invention provides for a VV with the following modifications:
(i) a TK deletion;
(ii) an envelope with reduced glycosylation (e.g., reduced sialylation) relative to an unmodified virus;
(iii) a nucleic acid encoding TRIF, or a functional domain thereof; and/or
(iv) a nucleic acid encoding 15-PGDH, or a functional domain thereof.

In non-limiting embodiments, the present invention provides for a VV with the following modifications:
(i) a TK deletion;
(ii) an envelope with reduced glycosylation (e.g., reduced sialylation) relative to an unmodified virus;
(iii) a nucleic acid encoding TRIF, or a functional domain thereof;
(iv) a nucleic acid encoding 15-PGDH, or a functional domain thereof; and/or
(v) a C12L deletion.

In non-limiting embodiments, the present invention provides for a VV with the following modifications:
(i) a TK deletion;
(ii) an envelope with reduced glycosylation (e.g., reduced sialylation) relative to an unmodified virus;
(iii) a nucleic acid encoding TRIF, or a functional domain thereof;
(iv) a nucleic acid encoding 15-PGDH, or a functional domain thereof;
(v) a C12L deletion; and/or
(vi) a B5R deletion.

5.7 Methods of Treatment

The present invention provides a method of reducing the growth of a cancer cell comprising administering, to the cancer cell of a subject, an effective amount of an immunooncolytic VV, as described above. Reducing the growth of a cancer cell may be manifested, for example, by cell death or a slower replication rate or reduced growth rate of a tumor comprising the cell or a prolonged survival of a subject containing the cancer cell.

A "subject" or "patient," as used interchangeably herein, refers to a human or a non-human subject. Non-limiting examples of non-human subjects include non-human primates, dogs, cats, mice, rats, guinea pigs, rabbits, pigs, fowl, horses, cows, goats, sheep, etc.

The present invention provides a method of reducing the growth of a tumor comprising administering, to the tumor, an effective amount of an immunooncolytic VV, as described above. Reducing the growth of a tumor may be manifested, for example, by reduced growth rate or a prolonged survival of a subject containing the tumor.

The present invention provides a method of treating a subject having a cancer comprising administering, to the subject, an effective amount of an immunooncolytic VV as described above.

An "effective amount" in such a method includes an amount that reduces growth rate or spread of the cancer or that prolongs survival in the subject. In certain embodiments, an effective amount can include an amount that is sufficient to produce an anti-cancer effect in a subject.

An "anti-cancer effect," as used herein, refers to one or more of a reduction in aggregate cancer cell mass, a reduction in cancer cell growth rate, a reduction in cancer cell proliferation, a reduction in tumor mass, a reduction in tumor volume, a reduction in tumor cell proliferation, a reduction in tumor growth rate and/or a reduction in tumor metastasis.

In certain embodiments, the present invention provides a method of producing an anti-cancer effect in a subject having a cancer comprising administering, to the subject, an effective amount of an immunooncolytic VV, as described above.

In specific non-limiting embodiments, the amount of VV administered (e.g., dose) may be between about $10^3$ and $10^{11}$ plaque forming units (PFU), or between about $10^5$ and $10^{10}$ PFU, or between about $10^5$ and $10^8$ PFU, or between about $10^5$ and $10^{11}$ PFU or between about $10^8$ and $10^{11}$ PFU. See also Thorne and Kim, 2009, Nat Rev Cancer 9: 64-71. Note that herein $10^x$ is alternatively expressed as 1 eX. In certain embodiments, the oncolytic virus can be administered in a single dose or can be administered in multiple doses. In certain embodiments where the virus is administered in multiple does, the doses can be administered sequentially, e.g., at daily, weekly or monthly intervals, or in response to a specific need of the subject.

In certain embodiments, the immunooncolytic virus can be administered in a pharmaceutical composition, wherein the virus is present in an effective amount and combined with a pharmaceutically acceptable carrier. "Pharmaceutically acceptable," as used herein, includes any carrier which does not interfere with the effectiveness of the biological activity of the active ingredients and/or that is not toxic to the patient to whom it is administered. Non-limiting examples of suitable pharmaceutical carriers include phosphate buffered saline solutions, water, emulsions, such as oil/water emulsions, various types of wetting agents and sterile solutions. Additional non-limiting examples of pharmaceutically compatible carriers can include gels, bioadsorbable matrix materials, implantation elements containing the oncolytic VV or any other suitable vehicle, delivery or dispensing means or material. Such carriers can be formulated by conventional methods and can be administered to the subject at an effective amount.

The VVs of the present invention can be produced by methods known to one of skill in the art. In certain embodiments, the VV can be propagated in suitable host cells, isolated from host cells and stored in conditions that promote stability and integrity of the virus, such that loss of infectivity over time is minimized. For example, the VV can be stored by freezing or drying, such as by lyophilization. In certain embodiments, prior to administration, the stored VV can be reconstituted (if dried for storage) and diluted in a pharmaceutically acceptable carrier for administration.

The oncolytic virus may be administered to the subject using standard methods of administration. In certain non-limiting embodiments, the oncolytic virus can be administered systemically. Alternatively or additionally, the oncolytic virus can be administered by injection at the site of the cancer, e.g., tumor site. For example, and not by way of limitation, the route of administration may be inhalation, intranasal, intravenous, intraarterial, intrathecal, intratumoral, intraperitoneal, intramuscular, subcutaneous, topical, intradermal, local regional, oral administration, or combinations thereof. In certain embodiments, the oncolytic virus can be administered to the patient from a source implanted in the patient. In certain embodiments, administration of the oncolytic virus can occur by continuous infusion over a selected period of time. In certain embodiments, pharmaceutical compositions can be directly administered to a tumor site, e.g., via direct intratumoral injection.

Cancers that may be treated by immunooncolytic VV therapy include but are not limited to adenocarcinoma, osteosarcoma, cervical carcinoma, melanoma, hepatocellular carcinoma, breast cancer, lung cancer, prostate cancer, ovarian cancer, leukemia, lymphoma, renal carcinoma, pancreatic cancer, gastric cancer, colon carcinoma, duodenal cancer, glioblastoma multiforme, astrocytoma and sarcoma.

In certain embodiments, treatment using an immunooncolytic VV, as described above, can be used alone or in combination with one or more anti-cancer agents. An "anti-cancer agent," as used herein, can be any molecule, compound, chemical or composition that has an anti-cancer effect. Anti-cancer agents include, but are not limited to, chemotherapeutic agents, radiotherapeutic agents, cytokines, immune checkpoint inhibitors, anti-angiogenic agents, apoptosis-inducing agents, anti-cancer antibodies and/or anti-cyclin-dependent kinase agents.

In certain embodiments, treatment using an immunooncolytic VV can be used alone or in combination with one or immunomodulatory agents. An immunomodulatory agent can include any compound, molecule or substance capable of suppressing antiviral immunity associated with a tumor or cancer. In certain embodiments, the immunomodulatory agent is capable of suppressing innate immunity and/or adaptive immunity to the oncolytic virus. Non-limiting examples of immunomodulatory agents include anti-CD33 antibody or variable region thereof, an anti-CD11b antibody or variable region thereof, a COX2 inhibitor, e.g., celecoxib, cytokines, such as IL-12, GM-CSF, IL-2, IFNβ and IFNγ, and chemokines, such as MIP-1, MCP-1 and IL-8. In certain embodiments, the immunomodulatory agent includes immune checkpoint inhibitors such as, but not limited to, anti-CTLA4, anti-PD-1, anti-PDL1 and TLR agonists (e.g., Poly I:C).

"In combination with," as used herein, means that the immunooncolytic VV and the one or more agents are administered to a subject as part of a treatment regimen or plan. In certain embodiments, being used in combination does not require that the immunooncolytic VV and the one or more agents are physically combined prior to administration or that they be administered over the same time frame. For example, and not by way of limitation, the immunooncolytic VV and the one or more agents can be administered concurrently to the subject being treated, or can be administered at the same time or sequentially in any order or at different points in time.

In certain embodiments, a method of treating a subject having a cancer includes administering, to the subject, an effective amount of an immunooncolytic VV comprising: (i) an envelope with reduced glycosylation (e.g., reduced sialylation) relative to an unmodified virus; (ii) a nucleic acid encoding TRIF, or a functional domain thereof; and (iii) a nucleic acid encoding 15-PGDH, or a functional domain thereof.

In certain embodiments, a method of treating a subject having a cancer includes administering, to the subject, an effective amount of an immunooncolytic VV comprising: (i) an envelope with reduced glycosylation (e.g., reduced sialylation) relative to an unmodified virus; (ii) a nucleic acid encoding TRIF, or a functional domain thereof; (iii) a nucleic acid encoding 15-PGDH, or a functional domain thereof; and (iv) a C12L deletion.

In certain embodiments, a method of treating a subject having a cancer includes administering, to the subject, an effective amount of an immunooncolytic VV comprising: (i) an envelope with reduced glycosylation (e.g., reduced sialylation) relative to the unmodified virus; (ii) a nucleic acid encoding TRIF, or a functional domain thereof; (iii) a nucleic acid encoding 15-PGDH, or a functional domain thereof; (iv) a C12L deletion; and (v) a B5R deletion.

In certain embodiments, a method of treating a subject having a cancer includes administering, to the subject, an effective amount of an immunooncolytic VV comprising: (i) a TK deletion; (ii) an envelope with reduced glycosylation (e.g., reduced sialylation) relative to an unmodified virus; (iii) a nucleic acid encoding TRIF, or a functional domain thereof; and (iv) a nucleic acid encoding 15-PGDH, or a functional domain thereof.

In certain embodiments, a method of treating a subject having a cancer includes administering, to the subject, an effective amount of an immunooncolytic VV comprising: (i) a TK deletion; (ii) an envelope with reduced glycosylation (e.g., reduced sialylation) relative to an unmodified virus; (iii) a nucleic acid encoding TRIF, or a functional domain thereof; (iv) a nucleic acid encoding 15-PGDH, or a functional domain thereof; and (v) a C12L deletion.

In certain embodiments, a method of treating a subject having a cancer includes administering, to the subject, an effective amount of an immunooncolytic VV comprising: (i) a TK deletion; (ii) an envelope with reduced glycosylation (e.g., reduced sialylation) relative to the unmodified virus; (iii) a nucleic acid encoding TRIF, or a functional domain thereof; (iv) a nucleic acid encoding 15-PGDH, or a functional domain thereof; (v) a C12L deletion; and (vi) a B5R deletion.

In certain embodiments, the methods of the present invention can further include administering to the subject an effective amount of one or more agents. For example, and not by way of limitation, the agent can be an anti-cancer agent and/or an immunomodulatory agent, as described above.

5.8 Kits

The present invention further provides for kits that provide an immunooncolytic VV as described above. In certain embodiments, a kit of the present invention can include an immunooncolytic VV or a pharmaceutical composition comprising an immunooncolytic VV as described above. In certain embodiments, a kit of the present invention can further include one or more components such as instructions for use, devices and additional reagents, and components, such as tubes, containers and syringes for performing the methods disclosed above. In certain embodiments, a kit of the present invention can further include one or more agents, e.g., anti-cancer agents and/or immunomodulatory agents, that can be administered in combination with an immunooncolytic VV.

In certain embodiments, a kit of the present invention can include instructions for use, a device for administering the immunooncolytic VV to a subject, or a device for administering an additional agent or compound to a subject. For example, and not by way of limitation, the instructions can include a description of the immunooncolytic VV and, optionally, other components included in the kit, and methods for administration, including methods for determining the proper state of the subject, the proper dosage amount and the proper administration method for administering the immunooncolytic VV. Instructions can also include guidance for monitoring the subject over the duration of the treatment time.

In certain embodiments, a kit of the present invention can include a device for administering the immunooncolytic VV to a subject. Any of a variety of devices known in the art for administering medications and pharmaceutical compositions can be included in the kits provided herein. For example, and not by way of limitation, such devices include, a hypodermic needle, an intravenous needle, a catheter, a needle-less injection device, an inhaler and a liquid dispenser, such as an eyedropper. In certain embodiments, an immunooncolytic VV to be delivered systemically, for example, by intravenous injection, can be included in a kit with a hypodermic needle and syringe.

In certain embodiments, a kit of the present invention includes an effective amount of an immunooncolytic VV comprising: (i) an envelope with reduced glycosylation (e.g., reduced sialylation) relative to an unmodified virus; (ii) a nucleic acid encoding TRIF, or a functional domain thereof; and (iii) a nucleic acid encoding 15-PGDH, or a functional domain thereof.

In certain embodiments, a kit of the present invention includes an effective amount of an immunooncolytic VV comprising: (i) an envelope with reduced glycosylation (e.g., reduced sialylation) relative to an unmodified virus; (ii) a nucleic acid encoding TRIF, or a functional domain thereof; (iii) a nucleic acid encoding 15-PGDH, or a functional domain thereof; and (iv) a C12L deletion.

In certain embodiments, a kit of the present invention includes an effective amount of an immunooncolytic VV comprising: (i) an envelope with reduced glycosylation (e.g., reduced sialylation) relative to the unmodified virus; (ii) a nucleic acid encoding TRIF, or a functional domain thereof; (iii) a nucleic acid encoding 15-PGDH, or a functional domain thereof; (iv) a C12L deletion; and (v) a B5R deletion.

In certain embodiments, a kit of the present invention includes an effective amount of an immunooncolytic VV comprising: (i) a TK deletion; (ii) an envelope with reduced glycosylation (e.g., reduced sialylation) relative to an unmodified virus; (iii) a nucleic acid encoding TRIF, or a functional domain thereof; and (iv) a nucleic acid encoding 15-PGDH, or a functional domain thereof.

In certain embodiments, a kit of the present invention includes an effective amount of an immunooncolytic VV comprising: (i) a TK deletion; (ii) an envelope with reduced glycosylation (e.g., reduced sialylation) relative to an unmodified virus; (iii) a nucleic acid encoding TRIF, or a functional domain thereof; (iv) a nucleic acid encoding 15-PGDH, or a functional domain thereof; and (v) a C12L deletion.

In certain embodiments, a kit of the present invention includes an effective amount of an immunooncolytic VV comprising: (i) a TK deletion; (ii) an envelope with reduced glycosylation (e.g., reduced sialylation) relative to an unmodified virus; (iii) a nucleic acid encoding TRIF, or a functional domain thereof; (iv) a nucleic acid encoding 15-PGDH, or a functional domain thereof; (v) a C12L deletion; and (vi) a B5R deletion.

The following Examples are offered to more fully illustrate the disclosure, but are not to be construed as limiting the scope thereof.

6. EXAMPLE 1

Effect of the Backbone Mutation C12L

Western Reserve thymidine kinase negative ("TK-") vaccinia virus (VV) was modified to delete C12L. The Western Reserve vaccinia strain was obtained from BEI Resources (Manassas, Va.), and all recombinant vaccinia viruses used or constructed were based on this strain.

A virus deletion mutant lacking 40% of the C12L ORF was constructed using transient dominant selection (Falkner & Moss, 1990, J Virol. 64(6): 3108-3111). Cells were infected with wild type vaccinia WR and simultaneously transfected with a plasmid containing regions 3' and 5' of the C12L gene. Recombination was allowed to occur and a selectable marker used to determine recombination events. Viruses were titered by plaque assay on BSC-1 cells, manufactured and purified as previously described for in vivo use (Sampath, P et al. (2013) *Mol. Ther.*, 21: 620-628).

C57BL/6 mice bearing a CMT-93 tumor were administered $5 \times 10^8$ plaque forming units ("PFU") of either unmodified WR virus or virus carrying the C12L deletion (WRΔC12L). To test the tumor-specificity of the virus, the amount of virus in brain, liver, lung and tumor was evaluated at 1, 3 and 10 days after infection. The results, in FIG. 1A, show that although approximately equivalent amounts of WR and WRΔC12L virus were found in liver, lung and tumor 1 day after infection, by ten days very little WRΔC12L virus was found in non-tumor tissue relative to the amount found in tumor, with the differential in tumor/non-tumor expression being much less for unmodified WR virus.

To evaluate the effect of the C12L mutation on survival, C57BL/6 mice (purchased from The Jackson Laboratory (Bar Harbor, Me.) bearing subcutaneous CMT-93 tumors were treated intravenously with a single, $1 \times 10^8$ PFU dose of WR or WRΔC12L virus, and then monitored. While all mice receiving WR virus had died before 60 days post-infection, after 70 days 50 percent of WRΔC12L animals were still alive (FIG. 1B).

Animals were first immunized with WR or WRΔC12L and the T-cells from these mice (or control mice) were mixed with WR and the resulting IFN-γ production levels were determined by ELISA. The results are shown in FIG. 1C and indicate that C12L deletion resulted in greater production of CTL or IFN-γ producing splenocytes.

7. EXAMPLE 2

Effect of Deglycosylation Treatment

Figure 2A:
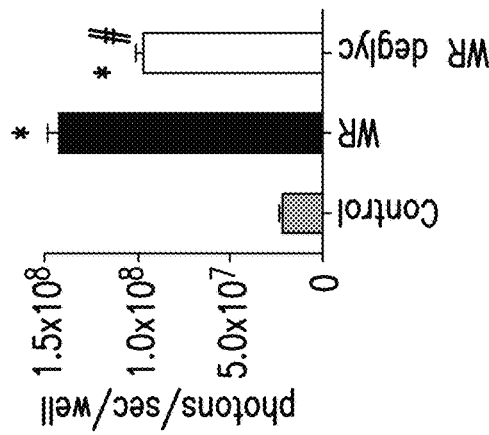
Figure 2B:
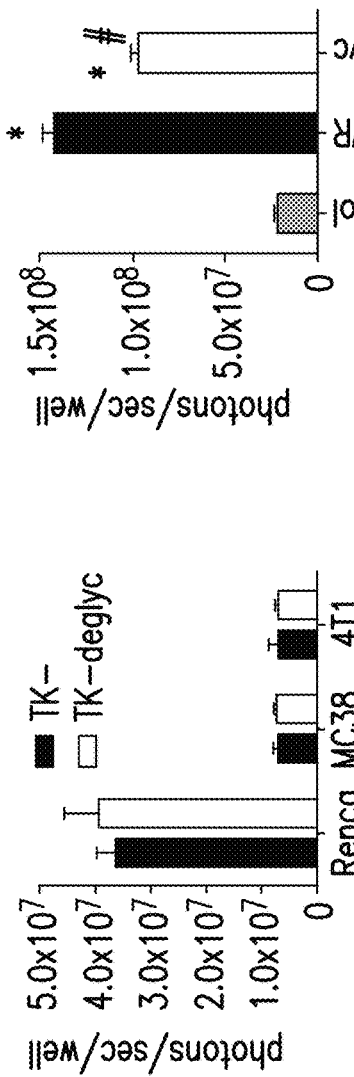

To test the effect of the modification of glycosylation of viral surface proteins, WR TK-VV, N-linked and simple O-linked glycans, e.g., sialic acid, were removed from the viral envelope using Sialidase A (Glyko Sialidase A, Code WS0042) or a cocktail of N- and O-glycanases and Sialidase A (Glycopro Enzymatic Deglycosylation kit, Product Code: GK80110, Prozyme). The non-denaturing protocol for deglycosylation of a virus was to take (i) 20 µl of virus stock; (ii) add 17 µl of deionized water; (iii) add 10 ul of 5× reaction buffer; (iv) add 1 ul each of N-Glycanase, Sialidase A and O-Glycanase (or any enzyme alone used with 19 ul of deionized water); and (v) incubate at 37° C. for 16 hours prior to use. Deglycosylation of the virus was confirmed by western blot analysis (FIG. 2A).

The effect of deglycosylation on virus infectivity was evaluated in different mouse tumor cell lines infected with TK-("WR" or "WR.TK-") or its deglycosylated version ("TK-deglyc," "WR deglyc" and "DS WR.TK-") at an MOI of 1. HeLa (human cervix adenocarcinoma), Bsc-1 (green monkey normal kidney cells), 143B (human osteosarcoma), CV-1 (green monkey kidney fibroblasts), Renca (murine renal adenocarcinoma) and 4T1 (murine breast cancer) cell lines were obtained from the American Type Culture Collection (Manassas, Va.). HEK293-mTLR2 cells were purchased from InvivoGen (San Diego, Calif.). MC38 (murine colon adenocarcinoma) and MEFs (murine embryonic fibroblasts) cell lines were, respectively, a kind gift from Dr. David Bartlett and Dr. Robert Sobol (University of Pittsburgh Cancer Center). All cell lines were maintained in recommended culture media containing 5-10% fetal bovine serum and antibiotics at 37° C., 5% $CO_2$. Viral infectivity was determined by analyzing viral gene expression. Viral gene expression was measured 3 hours after infection by bioluminescence imaging of luciferase expression in vitro. For cultured cells, 10 µl of 30 mg/ml D-luciferin (GoldBio, St Louis, Mo.) were added to 1 ml of culture media. As observed in FIG. 2B, deglycosylation of the virus envelope did not have an effect on the infectivity of the virus.

Figure 2C:
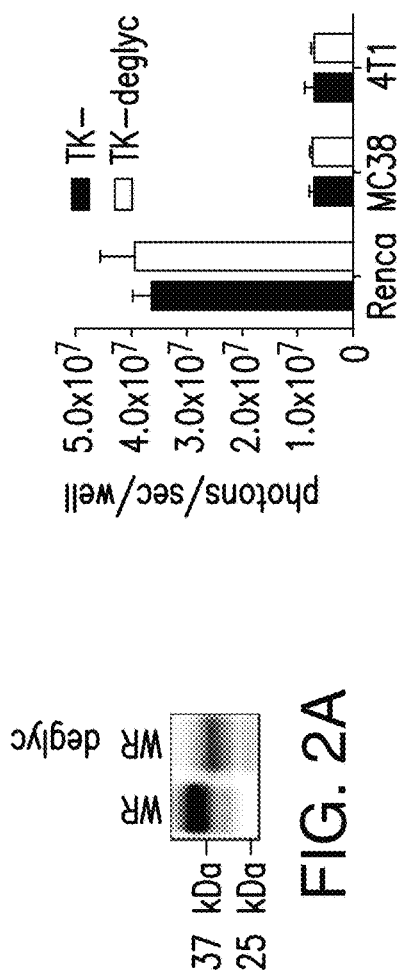
Figure 3A:
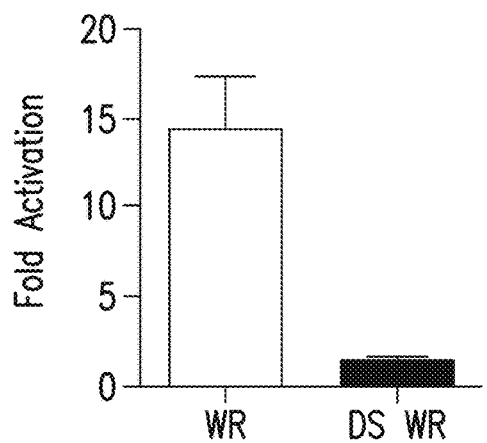

The effect of deglycosylation on TLR2 activation was evaluated in a model system which measures NF-κB activation in HEK293 cells engineered to express TLR2 (HEK293/mTLR2) and transfected with pNiFty, a TLR-signaling reporter plasmid. pNiFty (TLR-signaling reporter plasmid-Luciferase) was obtained from InvivoGen and transfected into HEK293/mTLR2 cells using FuGENE HD transfection reagent (Promega, Madison, Wis.). HEK293/mTLR2 cells were infected at an MOI of 1 with WR or WR deglycosylated virus and TLR2 activation was quantified 24 hours after infection by bioluminescence imaging. As shown in FIG. 2C, deglycosylation of the virus resulted in less activation of TLR2 in vitro compared to virus that was not deglycosylated. Furthermore, and as can be seen in FIG. 3A, deglycosylated virus was associated with substantially less TLR2 activation than WR virus.

The deglycosylated virus also exhibited greater uptake by tumors. For these experiments, the luciferase gene under the control of the synthetic vaccinia promoter pE/L (Chakrabarti et al. (1997). Biotechniques 23: 1094-1097) was incorporated into WR.TK- or DS WR.TK-vaccinia virus ("WR.TK-Luc+" and "DS WR.TK-Luc+", respectively), and introduced intravenously into BALB/c mice (purchased from The Jackson Laboratory (Bar Harbor, Me.)) bearing 4T1 subcutaneous tumor. Viral gene expression in the tumor could then be measured by bioluminescence imaging of luciferase expression in vivo. For animal models, a dose of 4.5 mg of D-luciferin was injected intraperitoneally per mouse before imaging. An IVIS 2000 model (PerkinElmer, Waltham, Mass.) was used for the imaging and images were analyzed with LivingImage software (PerkinElmer).

Figure 2D:
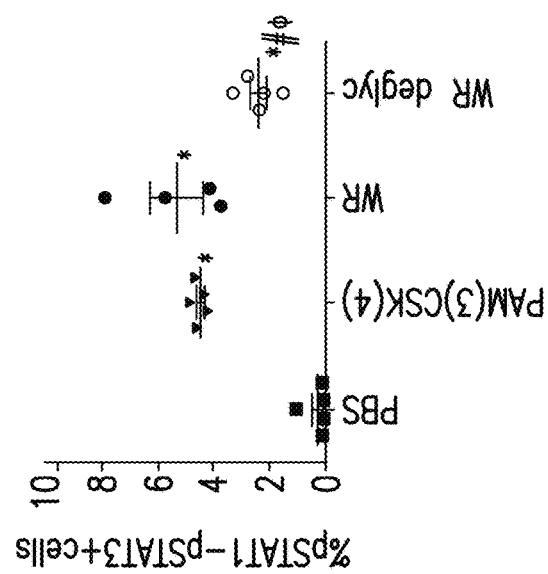
Figure 2E:
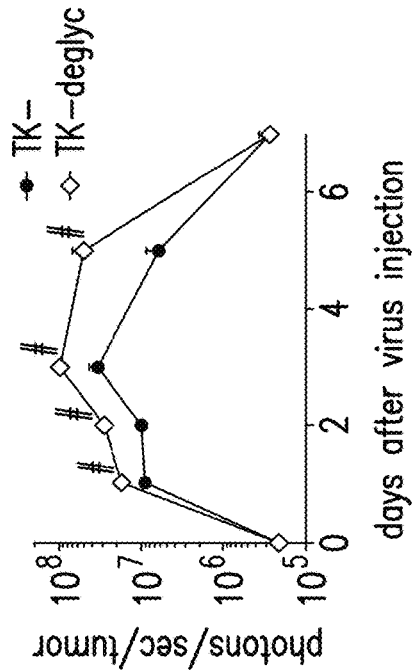
Figure 3B:
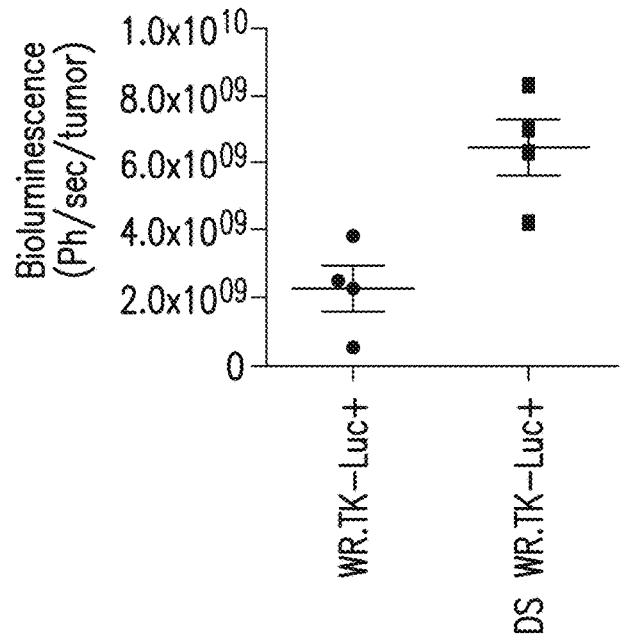
Figure 3C:
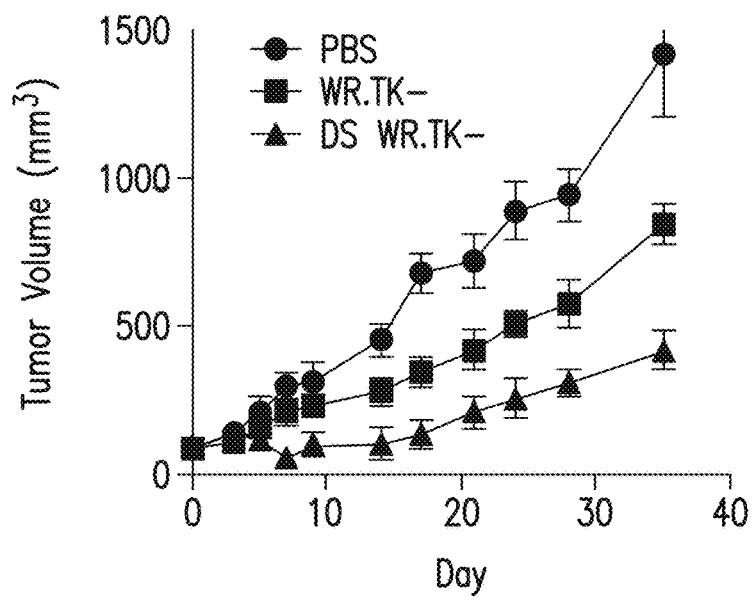

FIG. 3B shows that 24 hours after infection, there was significantly greater expression of DS WR.TK-Luc+ virus in the tumor relative to its glycosylated counterpart. This difference in uptake was not observed in non-tumor tissues. FIG. 3C shows that deglycosylated virus infection results in a smaller tumor volume. In addition, BALB/c mice harboring subcutaneous xenografts of Renca cells (mouse renal adenocarcinoma) were randomized and injected with a single intravenous dose of $1 \times 10^8$ PFU per mouse of TK- or TK-deglycosylated virus. Kinetics of viral gene expression from within the tumor was monitored by bioluminescence imaging of viral luciferase expression. As shown in FIG. 2E, deglycosylation of the viral envelope increased gene expression in tumors in vivo.

The effect of the deglycosylation of the virus on the presence of pSTAT1-pSTAT3+ lymphocytes was analyzed in C57BL/6 mice injected intravenously with $1 \times 10^7$ PFU of WR or WR deglycosylated virus. Spleens were harvested from C57BL/6 mice 1 hour after injection of the indicated viruses and splenocytes were isolated, fixated in 1.6% PFA and permeabilized with methanol. Two-color intracellular immunostaining analyses were performed using a LSR-Fortessa Flow Cytometer (BD Biosciences, San Jose, Calif.). Splenocytes were stained using PacificBlue anti-mouse pSTAT1 and AlexaFluor647 anti-mouse pSTAT3 antibodies (BD Biosciences). The percentage of pSTAT1-pSTAT3+ lymphocytes was determined by flow cytometry, and PBS and PAM(3)CSK(4) were used as controls. FIG. 2D shows that STAT3 phosphorylation was depleted in splenic lymphocytes of mice injected with deglycosylated vaccinia virus.

Figure 3D:
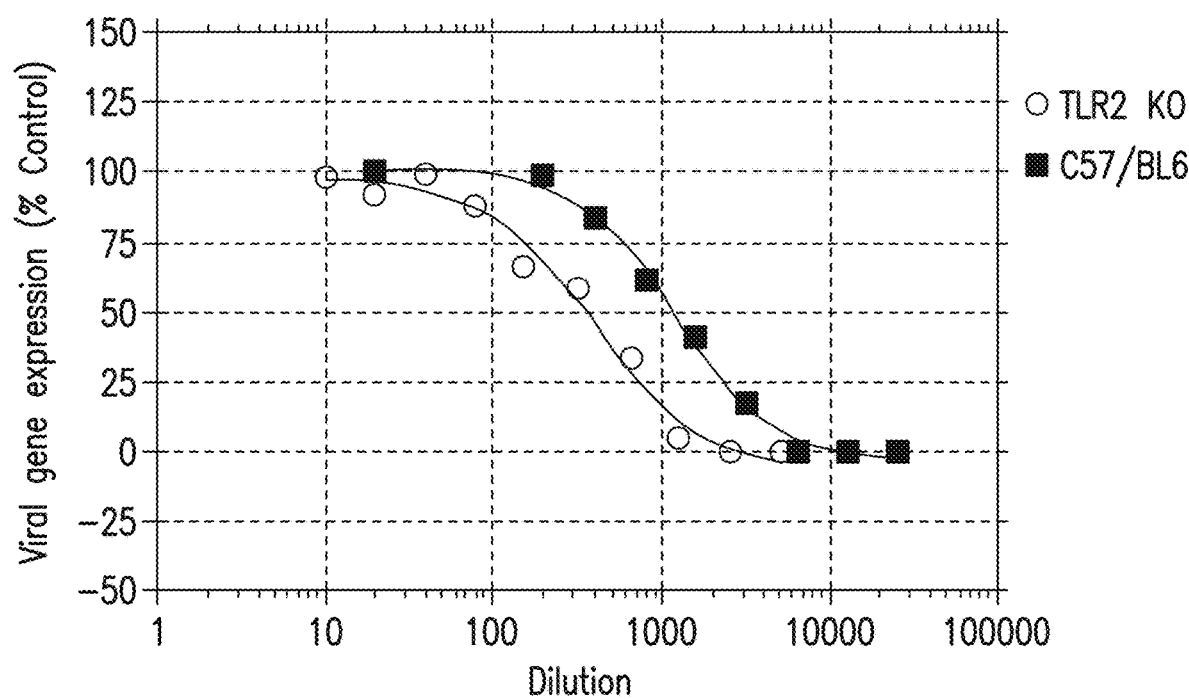

To determine the immune response against the virus in vivo, neutralizing antibody assays were performed. In brief, antibody-containing serum was obtained from mice treated as indicated at day 14 after virus injection and serial dilutions of the serum (starting at 1/20) were used to neutralize 1000 PFUs of TK-vaccinia virus. $2\times10^4$ HeLa cells were plated per well in 96-well and infected with serum-virus mix. At day 4 post-infection, plates were washed with PBS and absorbance was quantified after staining cultures using a nonradioactive cell proliferation assay kit (Promega, Madison, Wis.). $IC_{50}$ values (dilution of the serum required to neutralize Vaccinia virus capable of inducing 50% of cell inhibition) were estimated from dose-response curves by standard nonlinear regression, using an adapted Hill equation. As shown in FIG. 3D, the amount of neutralizing antibody against the virus is greater in wild-type C57BL/6 mice than in mice bearing a TLR2 knockout mutation. Accordingly, lower TLR2 activation associated with deglycosylated virus may be associated with less anti-virus antibody production and an improved anti-tumor response.

8. EXAMPLE 3

Effect of TRIF Expression

A nucleic acid encoding murine TRIF was introduced into WR.TK-virus and its effect on T cells was evaluated. TRIF was expressed from within the thymidine kinase locus, expressed from the viral early/late vaccinia p7.5 promoter ("TK-TRIF" OR "WR.TK-.TRIF"; FIG. 4A). A WR.TK- virus having a nucleic acid encoding murine DAI (DLM-1/ZBP1) expressed from the p7.5 and cloned into the locus of the viral thymidine kinase gene was generated ("TK-DAI"; FIG. 4A).

ELISA was performed to confirm expression of TRIF from the TK-TRIF virus (FIG. 4B). For ELISA, a mouse TRIF ELISA kit was used to determine the concentration of TRIF in supernatant or cell extracts of cells infected at an MOI of 1 (PFU/cell) with TK-TRIF. As shown in FIG. 4B, the TK-TRIF virus specifically expressed TRIF as compared to TK-. Western blot was used to confirm expression of DAI from the TK-DAI virus (FIG. 4C). For western blot analysis, cell cultures were seeded in 6-well plates and infected at an MOI of 5 (PFU/cell) and, 24 hours after infection, whole-cell protein extracts were incubated in cell lysis buffer (Cell Signaling Technology Inc, Danvers, Mass.) for 1 hour at 4° C. Clarified samples (15 µg/lane) were separated by a 10% SDS-PAGE gel and transferred to a nitrocellulose membrane. Mouse DAI protein was detected by immunoblotting membranes using a polyclonal anti-DAI primary antibody (Rabbit, Abcam, Cambridge, Mass.) and a polyclonal anti-rabbit conjugated with HRP (Goat, Thermo Scientific, Waltham, Mass.). A mouse monoclonal anti-β actin antibody (SantaCruz Biotechnologies, Santa Cruz, Calif.) and a peroxidase-conjugated anti-mouse antibody (Goat, Thermo Scientific) were used for immunoblotting of β-actin as a loading control. As shown in FIG. 4C, TK-DAI virus specifically expressed DAI compared to TK-.

As shown in FIG. 5A, expression of TRIF resulted in an increase in Type I interferon production by lymphocytes in vitro. Expression of TRIF also increased CTL production in vivo, as shown by ELISpot assay (FIG. 5B). For ELISpot assays, splenocytes were prepared from mice. Splenocytes were mixed with tumor cells or splenocytes previously infected with UV-inactivated vaccinia virus at a ratio of 5:1. Naïve splenocytes from each mouse were used as a control. 96-well membrane filter plates (EMD Millipore, Billerica, Mass.) coated with 15 µg/ml of monoclonal anti-mouse IFN-γ antibody AN18 (Mabtech, Inc., Cincinnati, Ohio) were used for the assays. Cells were maintained for 48 hours at 37° C. and spots were detected using 1 µg/ml of biotinylated anti-mouse IFN-γ antibody R4-6A2-biotin (Mabtech). Plates were developed using an ABC kit and an AEC substrate kit for peroxidase (Vector Laboratories, Inc., Burlingame, Calif.). Specific spots were counted and analyzed using an ImmunoSpot Analyzer and software (CTL, Shaker Heights, Ohio).

Figure 6A:
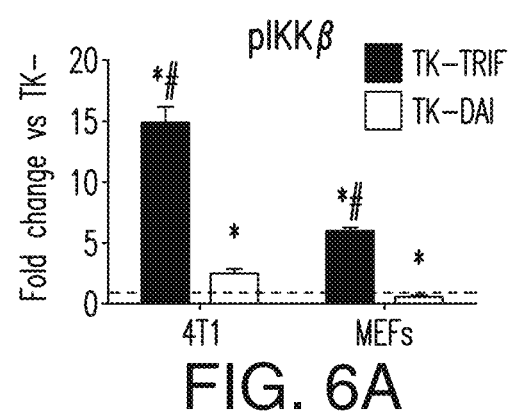
Figure 6B:
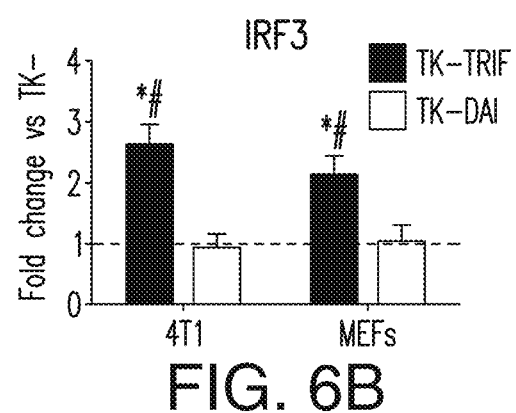
Figure 6C:
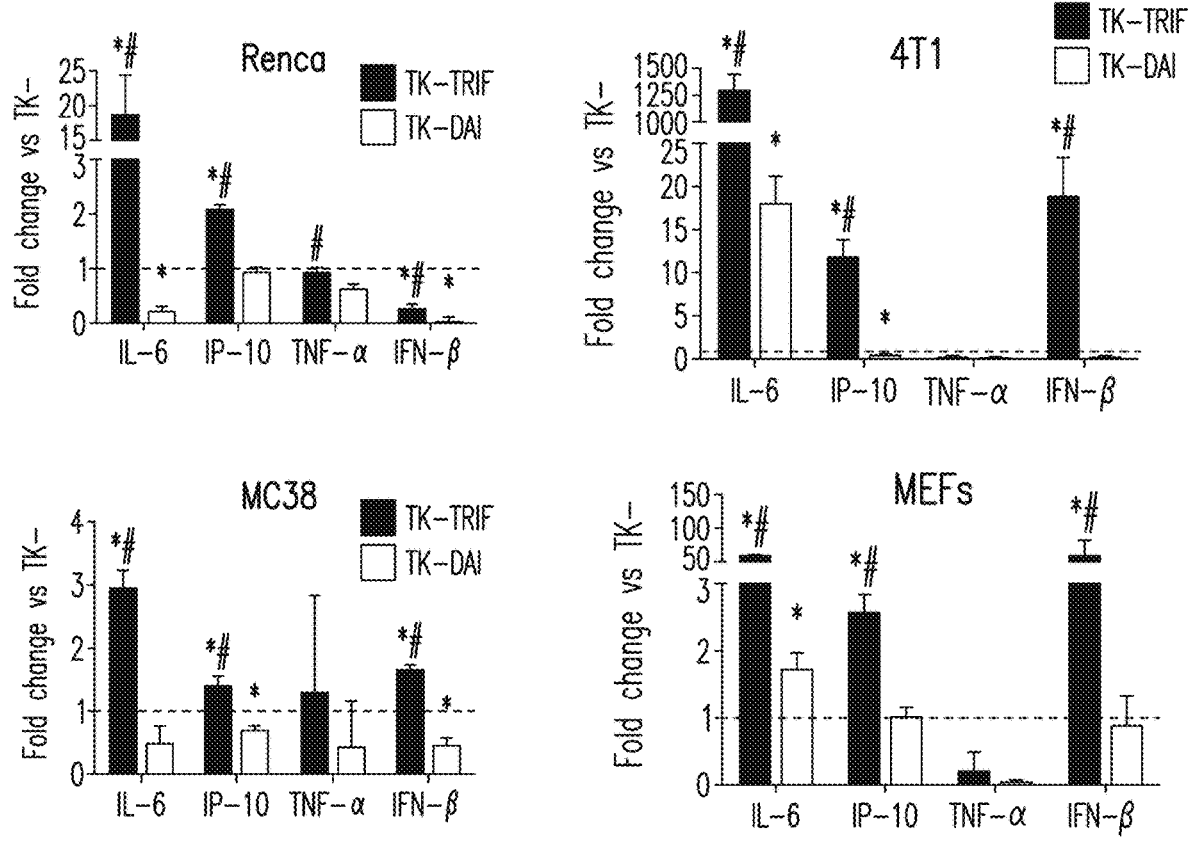
Figure 6D:
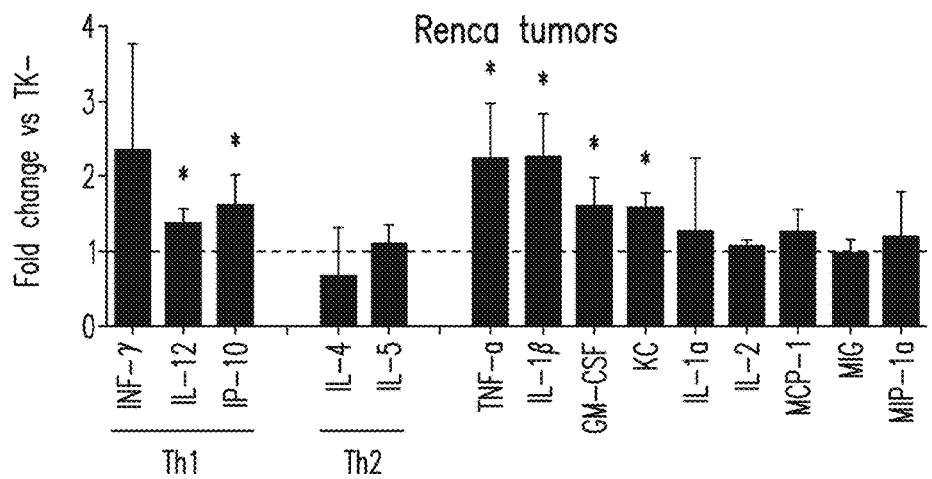

Analysis of the release of cytokines and chemokines in vitro and in vivo following 24 hours after infection of TK-, TK-TRIF or TK-DAI (MOI of 1) was performed by a Luminex assay. For cell culture supernatants, a Miliplex Mouse Cytokine Panel (5-plex) Kit from Milipore (Billerica, Mass.) and a Mouse 2-plex assay Kit from Panomics (Redwood City, Calif.) were used. For tumor lysates, a Cytokine Mouse 20-plex Panel Kit from Invitrogen (Carlsbad, Calif.) was used for determining concentrations in tumors harvested at day 4 after Vaccinia virus administration. Tumors were homogenized using Lysing Matrix D tubes and a FastPrep-24 instrument. As shown in FIGS. 6A and C, the concentrations of pIKKβ, IL-6, IP-10, TNF-α and IFN-β increased significantly upon infection with TK-TRIF as compared to TK- in different tumor cell lines as compared to TK-. In addition, BALB/c mice with established Renca subcutaneous xenografts injected with a single intravenous dose of $1\times10^8$ PFU per mouse of TK- or TK-TRIF were analyzed to determine the in vivo intratumoral concentration of cytokines and chemokines. 4 days after injection, tumors were harvested and concentration of a various cytokines and chemokines was determined in tumor lysates by luminex or ELISA assays. FIG. 6D shows that the intratumoral concentrations of INF-γ, IL-12, IP-10, TNF-α, IL-1β, GM-CSF and KC significantly increased in response to TK-TRIF as compared to TK-.

Figure 7A:
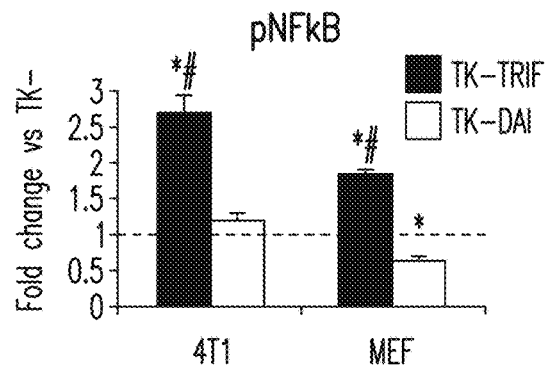
Figure 7B:
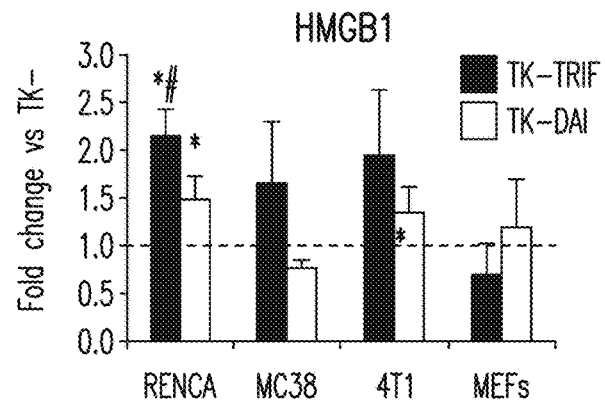
Figure 7C:
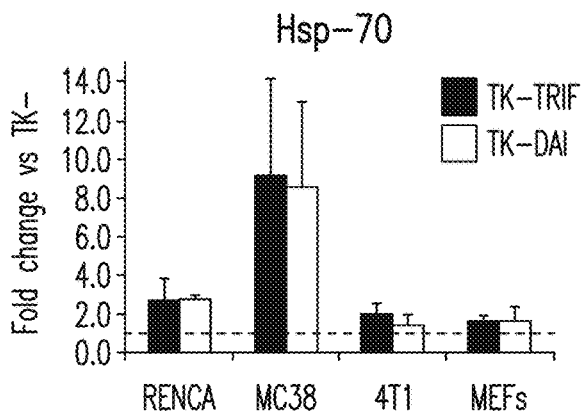
Figure 7D:
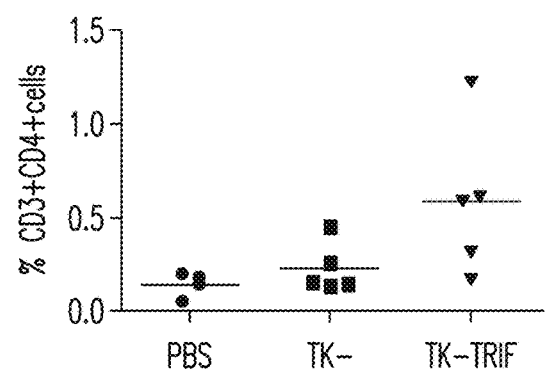
Figure 7E:
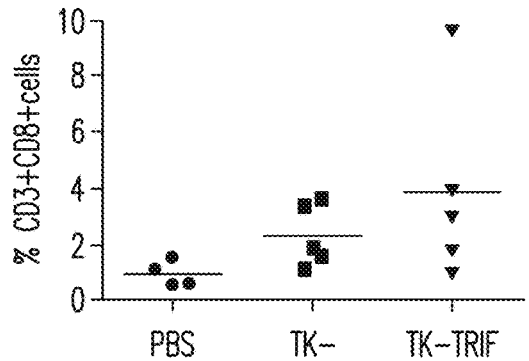

Activation of NF-κB and IRF3 pathways were analyzed after infection with TK-TRIF and TK-DAI. ELISA assays were utilized to determine concentrations of pIKKβ and IRF3 in cytoplasmic and nuclear extracts, respectively, of 4T1 or MEF cells infected with TK-, TK-TRIF or TK-DAI at an MOI of 1. As shown in FIGS. 6A and B, TK-TRIF increased the activation of the NF-κB and IRF3 signaling pathways as observed by an increase in the concentration of pIKKβ and IRF3 expression following 24 hours after infection. FIG. 7A shows that the phosphorylation of NF-κB increased following infection of TK-TRIF and TK-DAI. HMGB1 and Hsp-70, which function as regulators of NF-κB, also exhibited altered expression following infection by TK-TRIF (FIGS. 7B and 7C). The presence of CD4+ helper T cells and CD8+ cytotoxic T-cells were analyzed following infection with TK-, TK-TRIF. As shown in FIGS. 7D and E, the number of cytotoxic T-cells and helper T-cells were higher in mice infected with TK-TRIF.

Figure 8A:
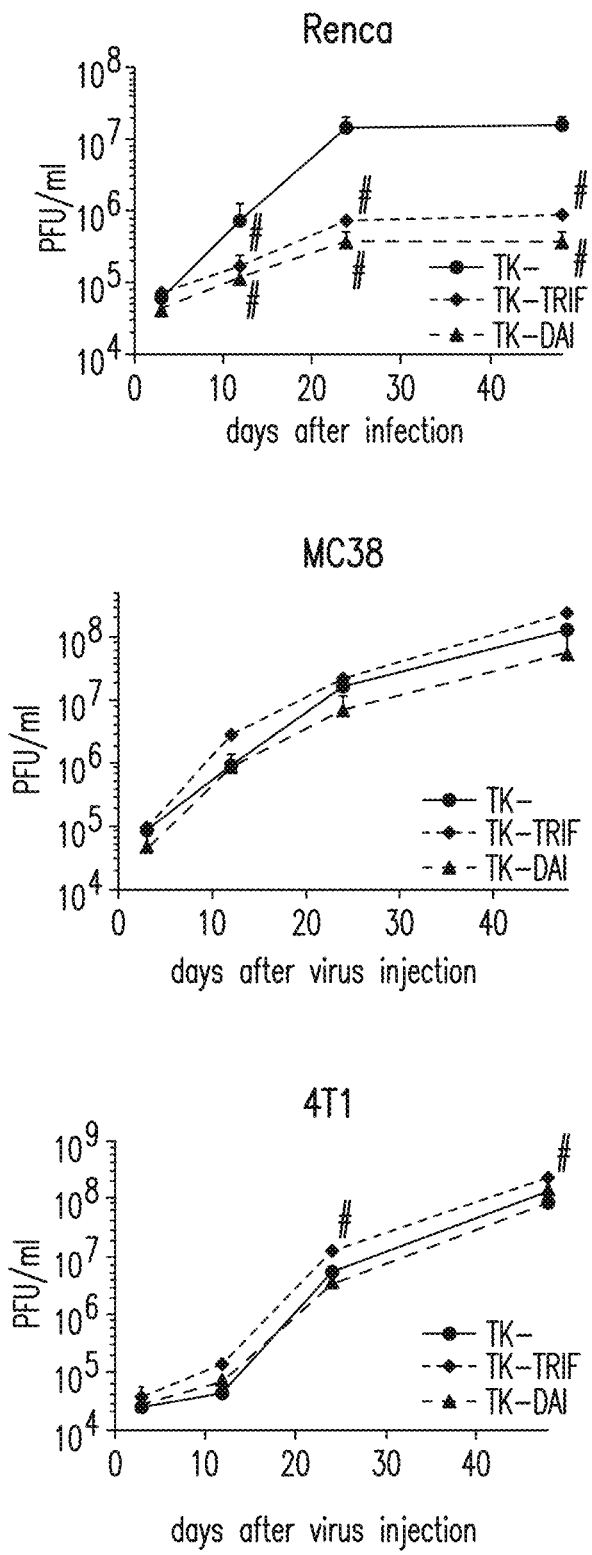

Analysis of the replication and antitumor activity of TK-TRIF was performed in different mouse tumor cells. Various tumor cell lines were infected with an MOI of 1 and virus production was measured by ELISpot plaque-assay, as described above, at different time points. As shown in FIG. 8A, viral production of both TK-TIRF and TK-DAI was significantly less in the resistant Renca cells as compared to TK-, but viral production of TK-TIRF and TK-DAI in MC38 and 4T1 cells were at similar levels to TK- (see also FIG. 9A).

Figure 8B:
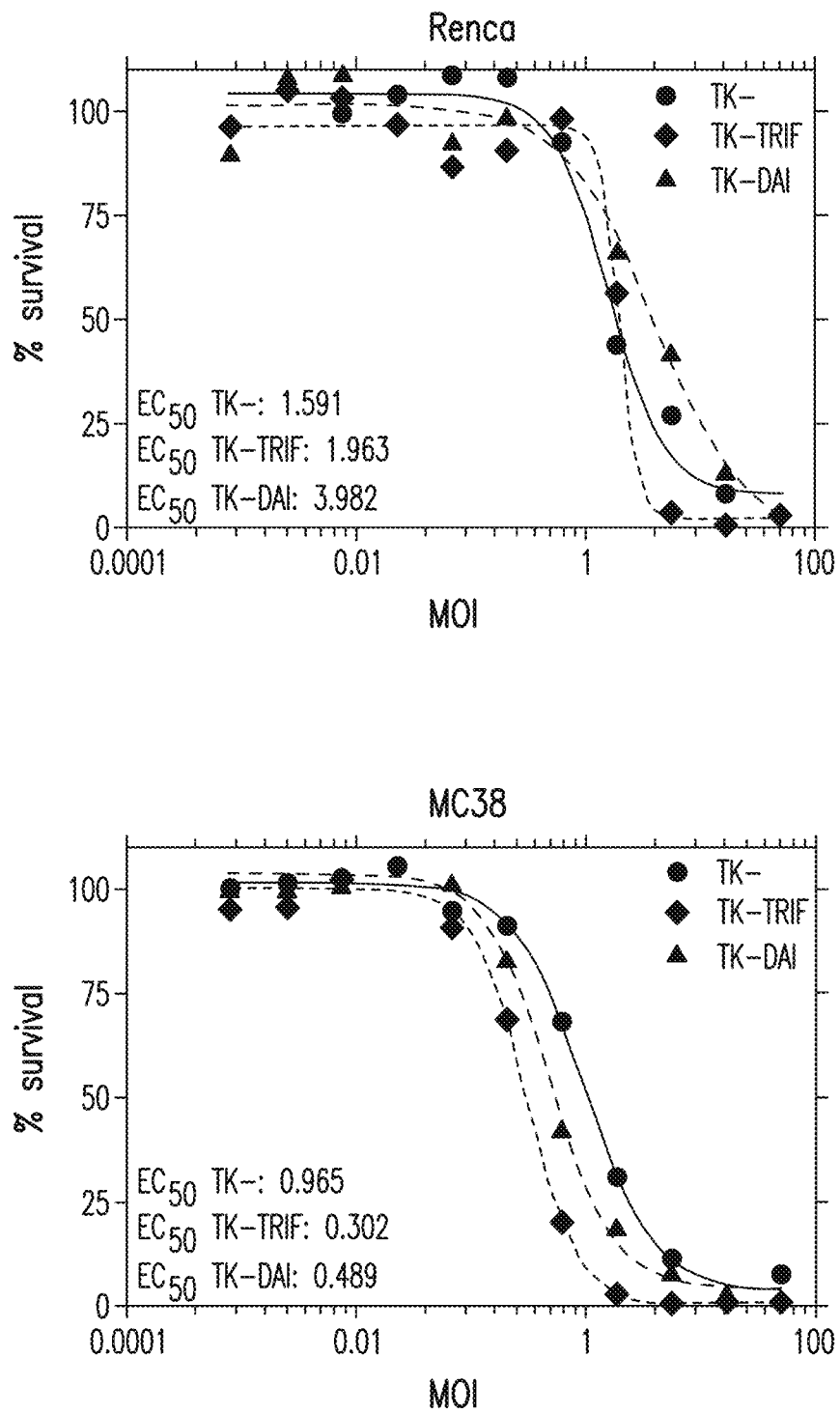
Figure 8B:
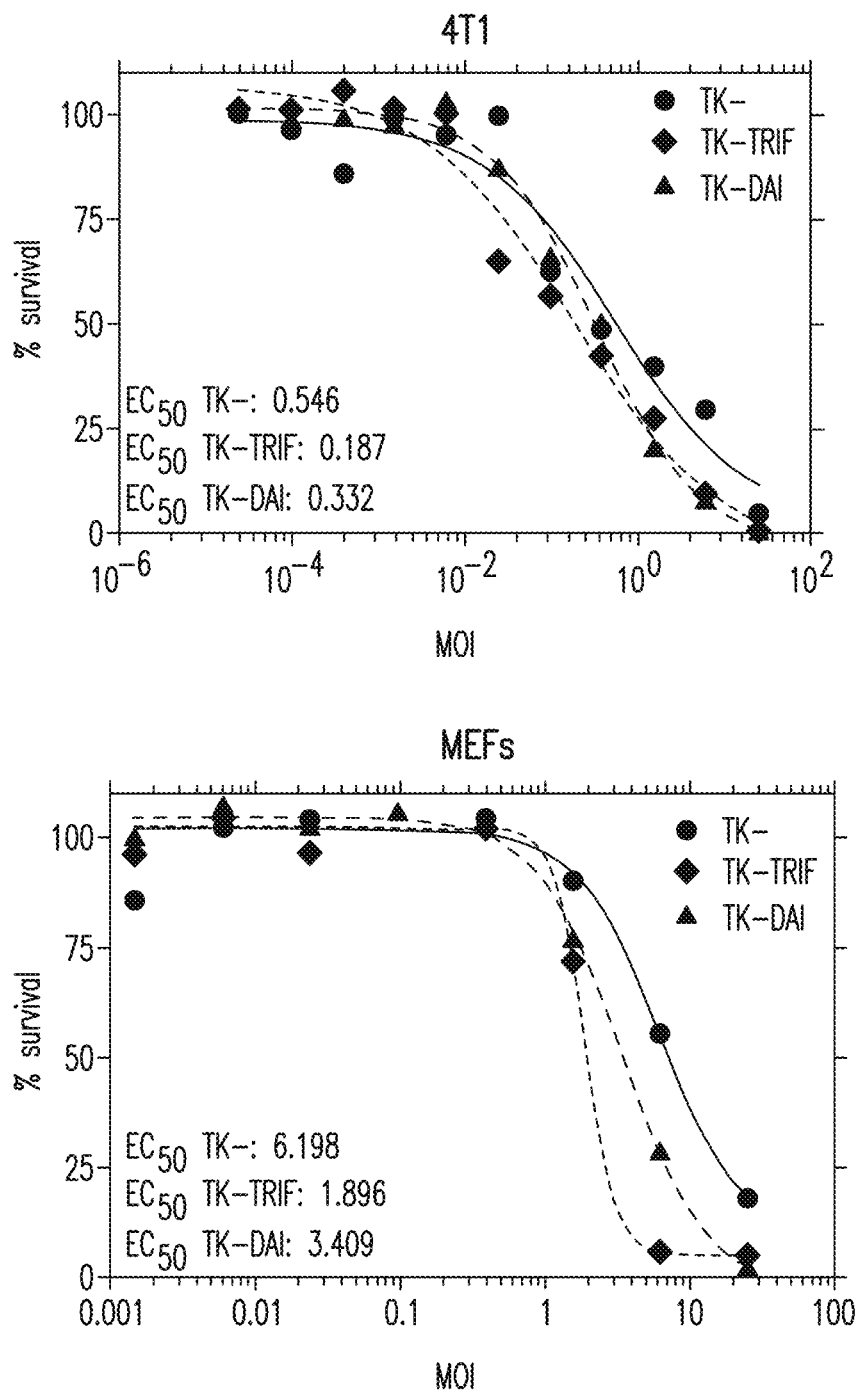
Figure 8C:
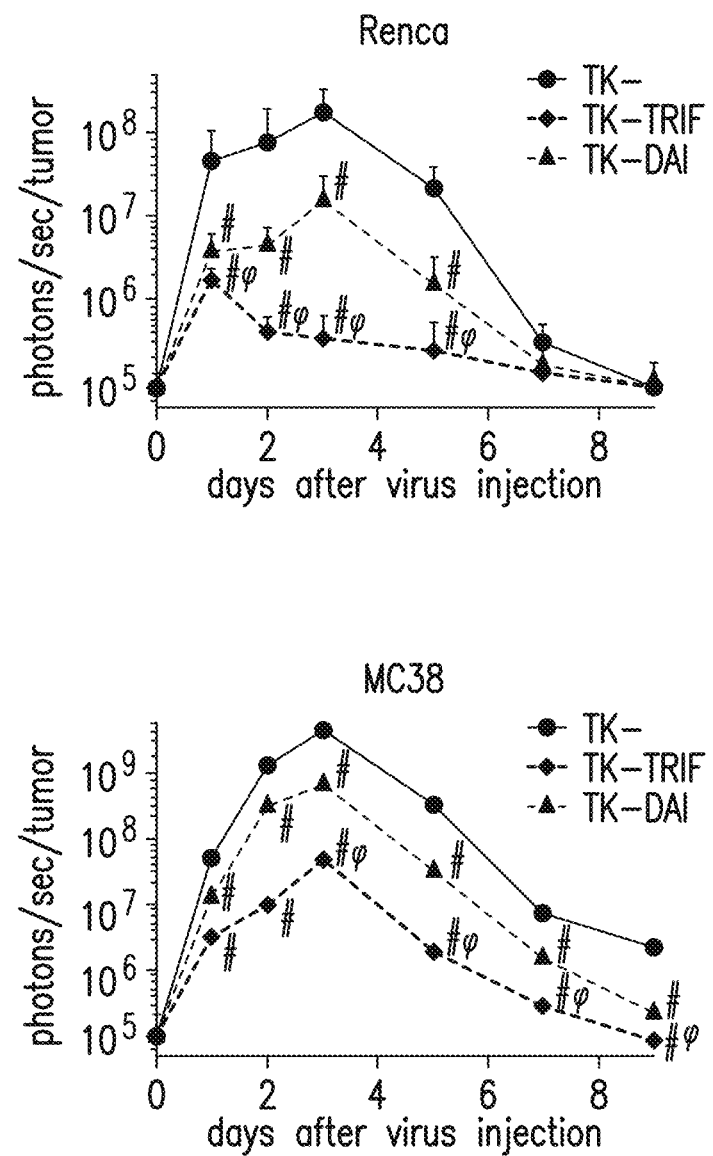
Figure 8D:
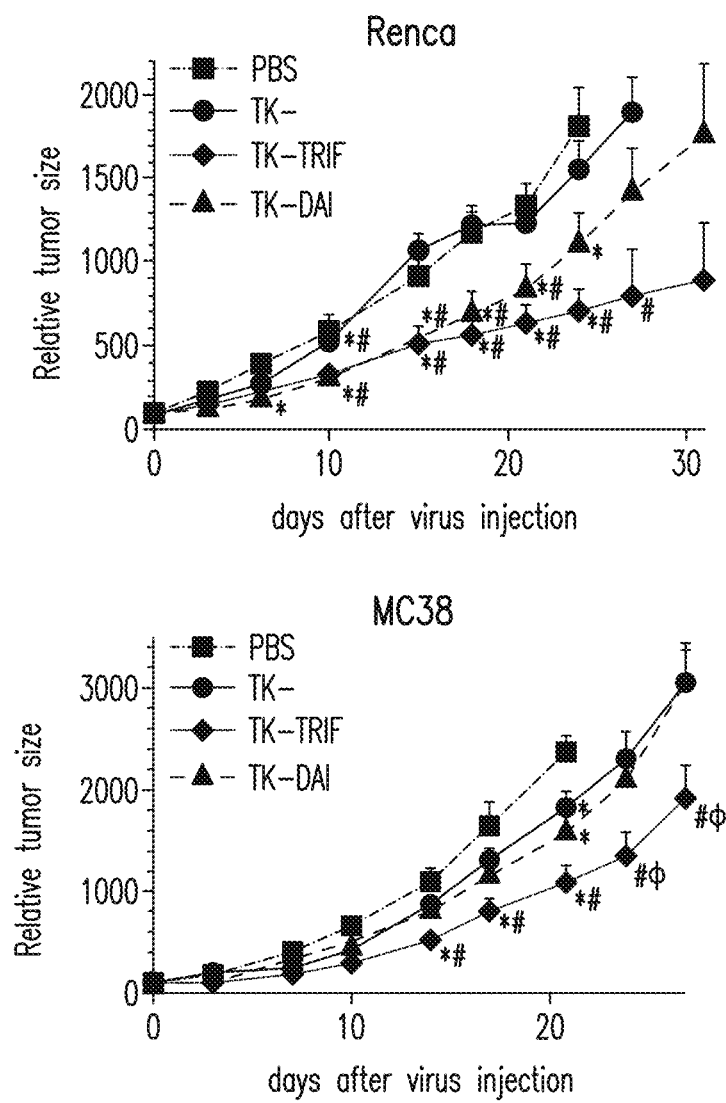
Figure 9A:
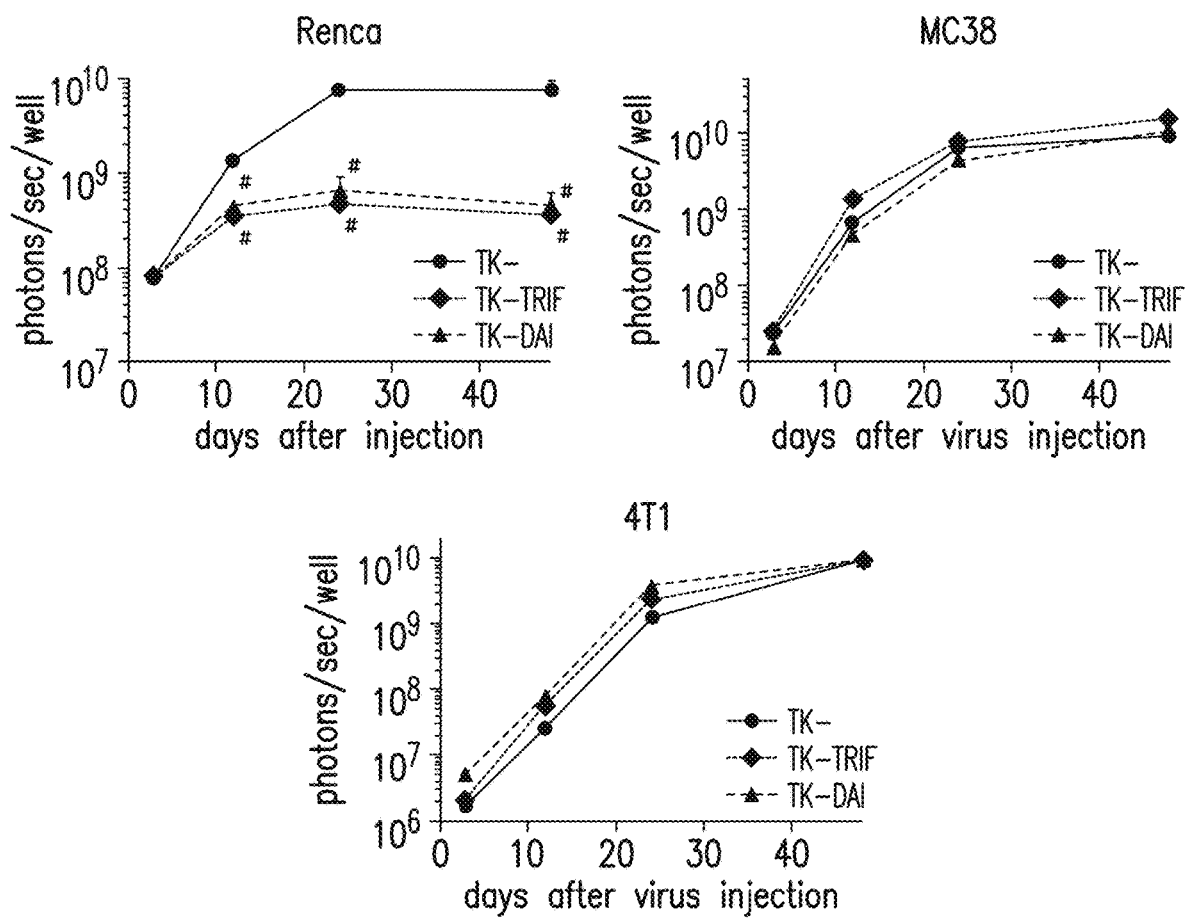
Figure 9B:
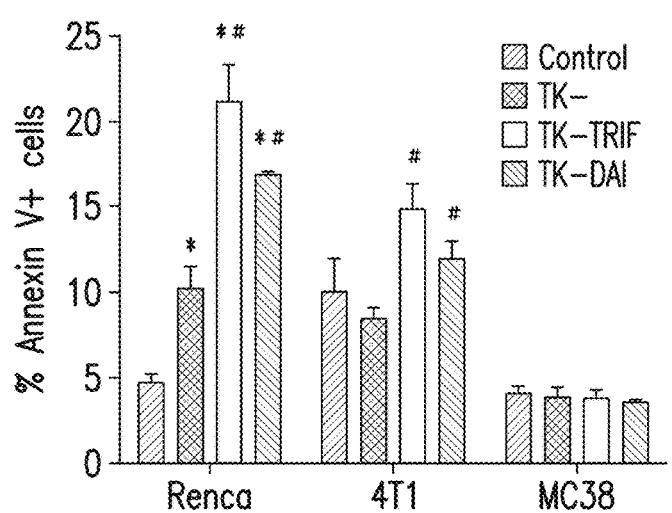
Figure 9C:
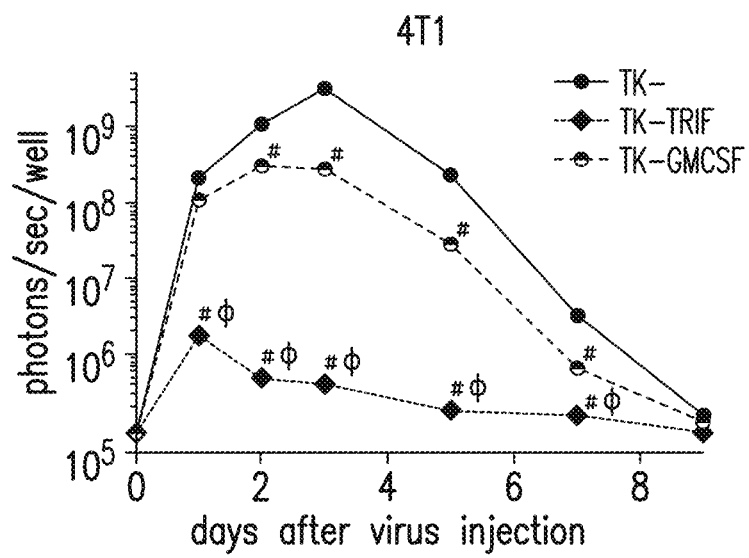
Figure 9D:
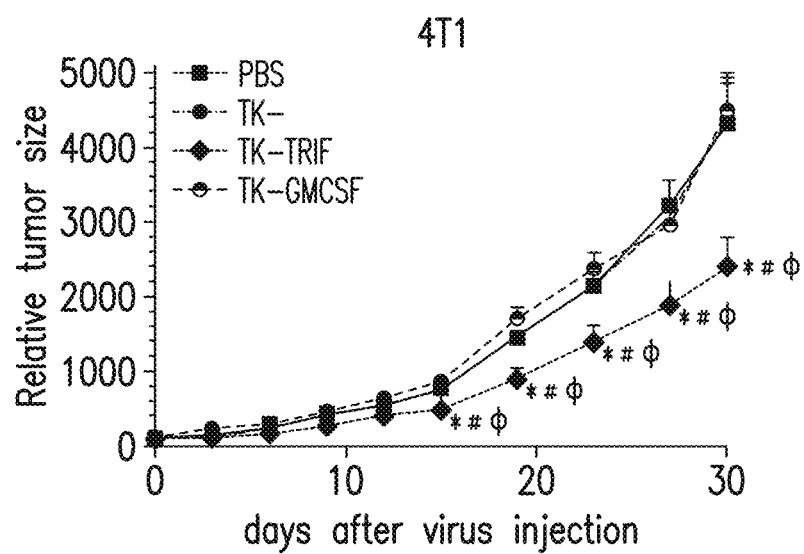

Further analysis of viral expression in tumors and tumor volumes were performed in BALB/c or C57BL/6 mice implanted with Renca or MC38 xenografts, respectively, and BALB/c mice implanted with 4T1 xenografts. BALB/c or C57BL/6 mice were injected with PBS or $1\times10^8$ PFU of TK-, TK-TRIF or TK-DAI through the tail vein. For the 4T1 semi-orthotopic model, $2\times10^5$ 4T1 cells were implanted into the fat pad of the mammary gland of BALB/C female mice. FIG. 8C shows that viral gene expression of TK-TRIF and TK-DAI was at a lower level in tumors of Renca or MC38 xenografts implanted in BALB/c or C57BL/6 mice, respectively, compared to viral gene expression of TK-. FIG. 9C shows that viral production and viral expression of TK-DAI and TK-TRIF was reduced in tumors as compared to viral expression of TK- or TK-virus expressing GM-CSF ("TK-GMCSF"). BALB/c mice with Renca tumors implanted subcutaneously were treated with an IV dose of $1\times10^8$ PFU once tumors reached 50-100 mm$^3$. Viruses used were WR.TK- and WR.TK-TRIF+(or PBS control). The subsequent tumor response was followed by caliper measurement, and a reduction in tumor growth was observed in mice infected with TK-TRIF (FIGS. 5C and FIG. 8D). A similar response was observed in mice implanted with MC38 tumors (FIG. 8D) and 4T1 tumors compared to tumors infected with TK-GMCSF (FIG. 9D).

Cytotoxicity of the modified virus as compared to TK- was determined by performing cytotoxicity assays. Cytotoxity assays were performed by seeding $2\times10^4$ cells per well in 96-well plates in DMEM with 5% FBS. Cells were infected with serial dilutions starting at a MOI of 75 and, at day 4 post-infection, plates were washed with PBS and absorbance was quantified after staining cultures using a non-radioactive cell proliferation assay kit (Promega, Madison, Wis.). $IC_{50}$ values (PFU per cell required to produce 50% inhibition) were estimated from dose-response curves by standard nonlinear regression, using an adapted Hill equation. FIG. 8B shows comparative cytotoxicity of TK-TRIF and TK-DAI in cells infected with the indicated viruses at doses ranging from 75 to 0.00025 PFU/cell. The modification of the TK- virus to express TRIF or DAI did not result in a change in cytotoxicity compared to TK-. Determination of the number of apoptotic cells by AnnexinV staining, as shown in FIG. 9B, indicates that infection of Renca and 4T1 cells resulted in an increase in apoptotic cells. Apoptosis/necrosis evaluation of cell lines, cells were infected with an MOI of 1 with indicated viruses and stained using an Annexin V-FITC Apoptosis Detection Kit (Abcam, Cambridge, Mass.) 48 hours after infection. Analyses were performed using an Accuri C6 Flow Cytometer (BD Biosciences).

Figure 9E:
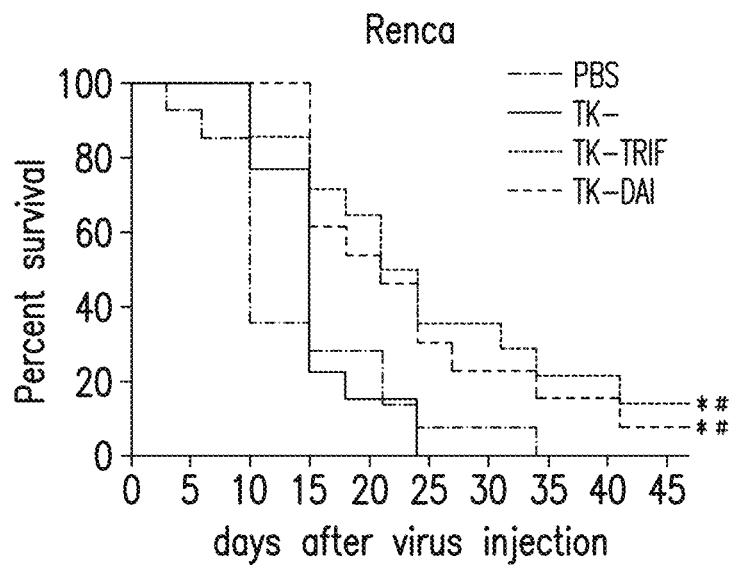
Figure 9F:
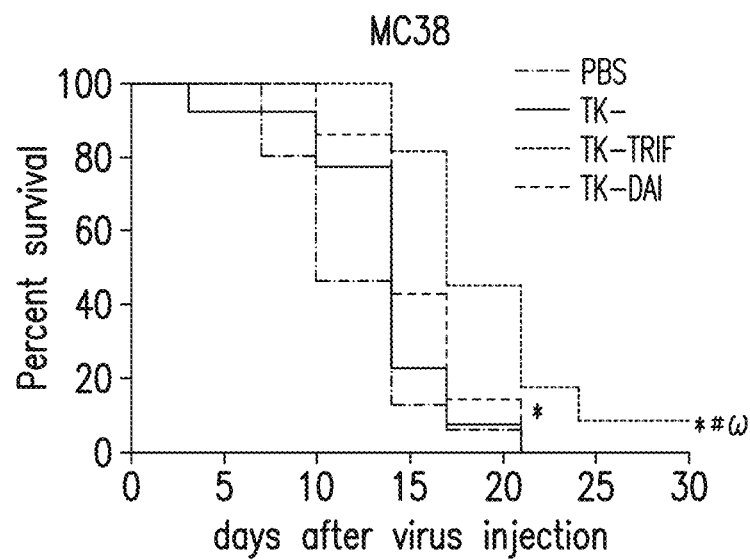

Experiments were performed to determine if TK-TRIF affects the survival of mice with Renca or MC38 xenografts compared to mice treated with TK- or PBS. Renca or MC38 xenografts were established in BALB/C or C57BL/6 mice, respectively, and treated with a single intravenous dose of $1\times10^8$ PFU of indicated viruses or PBS. As shown in FIGS. 9E and F, TK-TRIF significantly improved survival compared to treatment with TK-.

9. EXAMPLE 4

Effect of Combined TRIF Expression and Deglycosylation

TK-virus modified to express TRIF, as discussed above in 6.3, was deglycosylated ("TK-TRIF deglyc") to analyze the effect such a combination would have on the antitumor cellular responses and antitumor efficacy of the virus.

Figure 10A:
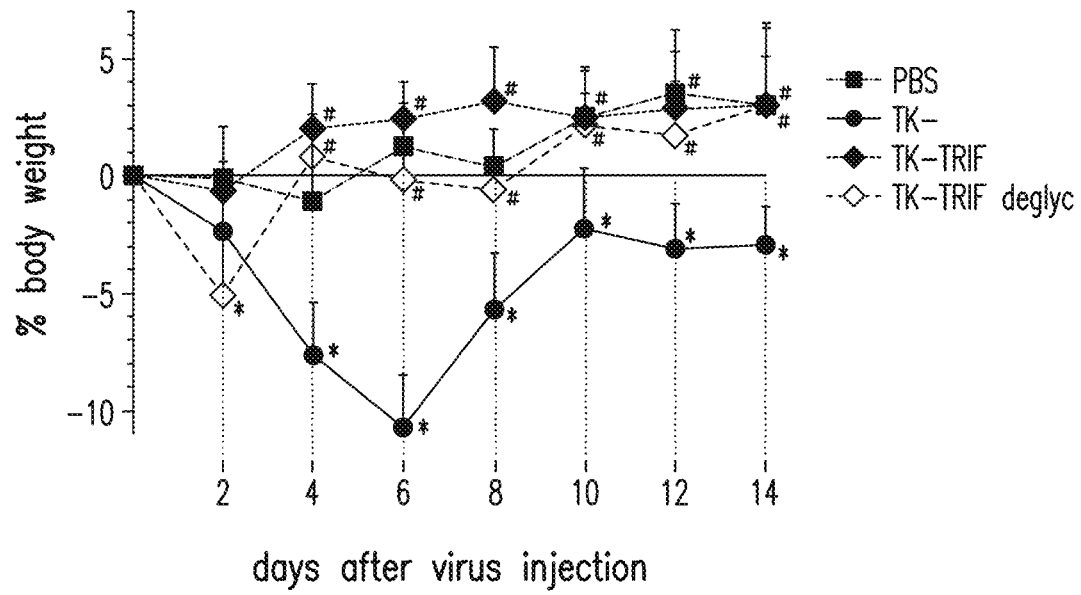

To determine the toxicity of the virus expressing TK-TRIF, the body weight of BALB/C mice injected intravenously with PBS as a control or $1\times10^8$ PFU per mouse of TK-, TK-TRIF, or TK-TRIF deglycosylated were analyzed. FIG. 10A shows that TK-injected mice presented more than 10% reduction in body-weight at day 6 after virus injection, whereas TK-TRIF and TK-TRIF deglyc-injected mice presented a similar weight profile than those injected with PBS, indicating that TK-TRIF and TK-TRIF deglyc are less toxic than TK-.

Figure 10B:
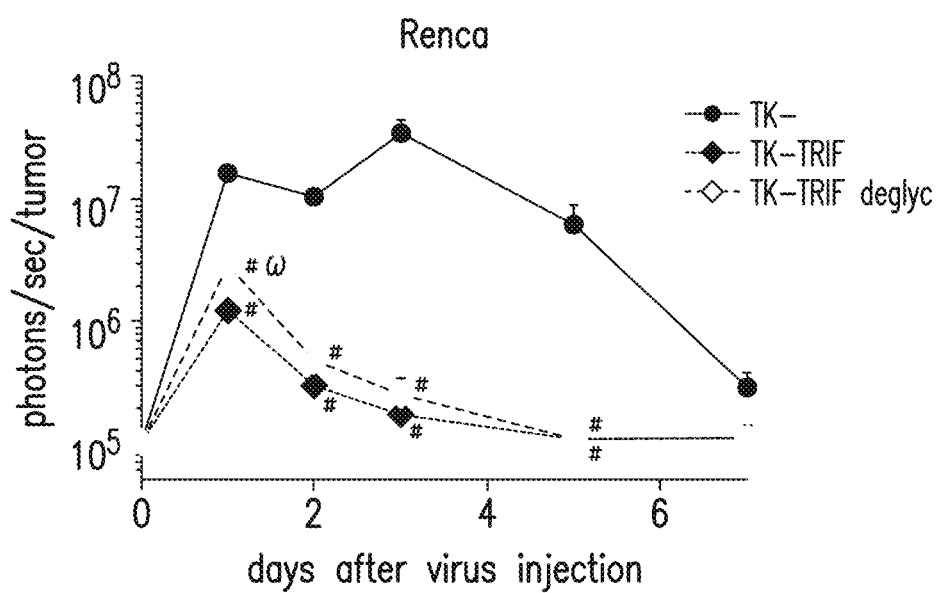

Viral gene expression of TK-TRIF-deglyc in in vivo, as compared to TK- and TK-TRIF, was analyzed. Renca tumors were implanted in BALB/c mice, and mice were injected with PBS or $1\times10^8$ pfu of TK-, TK-TRIF, or TK-TRIF deglyc through the tail vein. Viral gene expression was determined by detecting viral luciferase expression from within the tumors and measured at indicated time points. FIG. 10B shows that 24 hours after infection, there was less expression of TK-TRIF and TK-TRIF deglyc in the tumors compared to TK-.

Figure 10C:
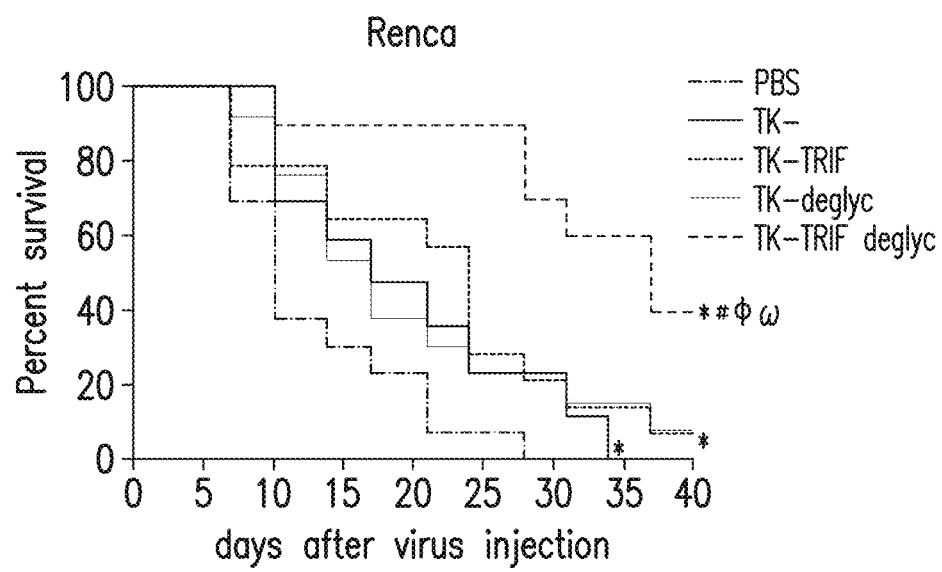
Figure 10D:
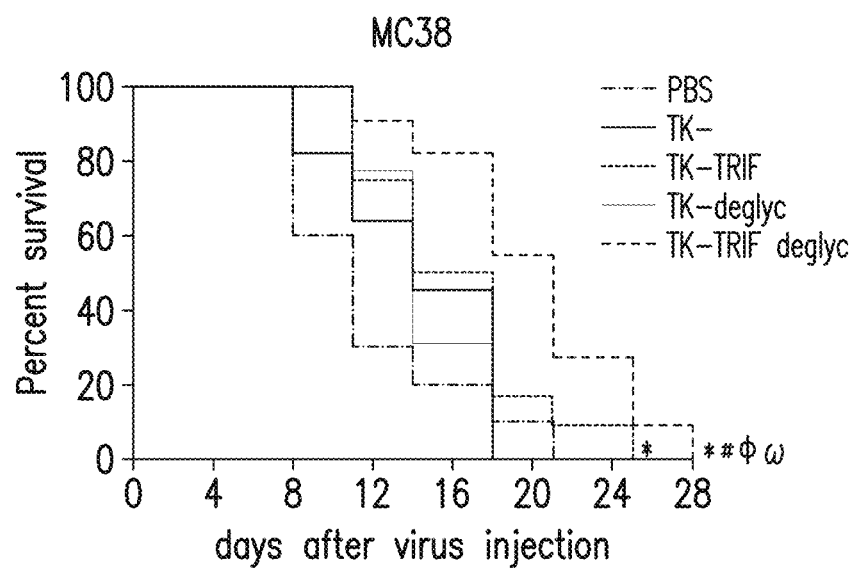
Figure 10E:
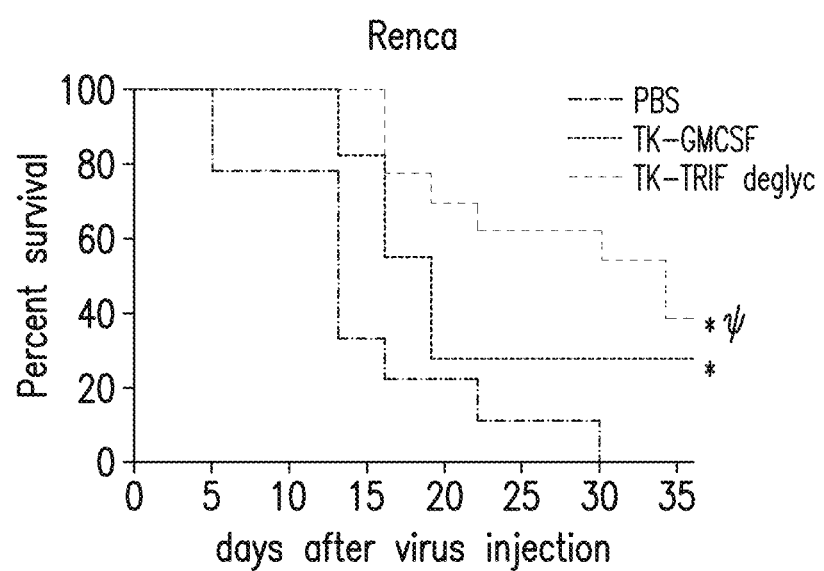

Experiments were performed to determine if TK-TRIF or TK-TRIF deglyc affected the survival of mice with Renca or MC38 xenografts compared to mice treated with TK- or PBS. Renca or MC38 xenografts were established in BALB/C or C57BL/6 mice, respectively, and treated with a single intravenous dose of $1\times10^8$ PFU of indicated viruses or PBS. As shown in FIGS. 10C and D, TK-TRIF and TK-TRIF deglyc significantly improved the survival of the mice compared to treatment with TK-. Also, TK-TRIF deglyc improved survival of mice with Renca tumors compared with TK-GMCSF treatment (FIG. 10E).

Figure 11A:
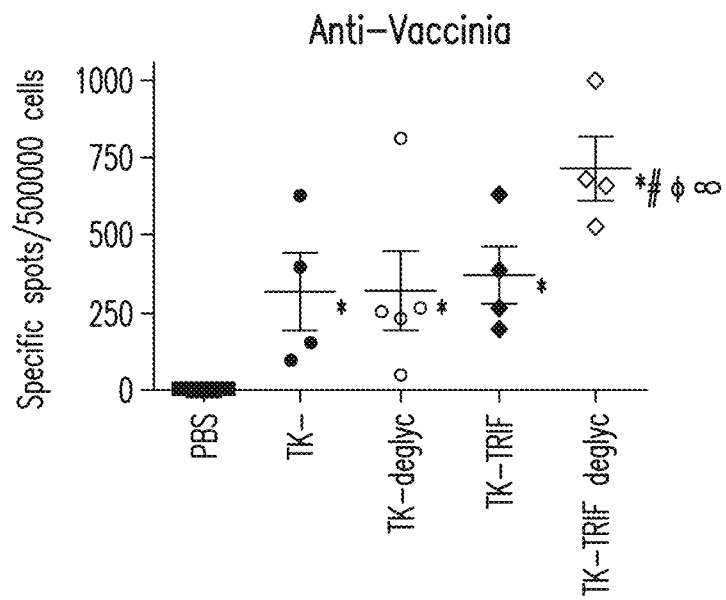
Figure 11B:
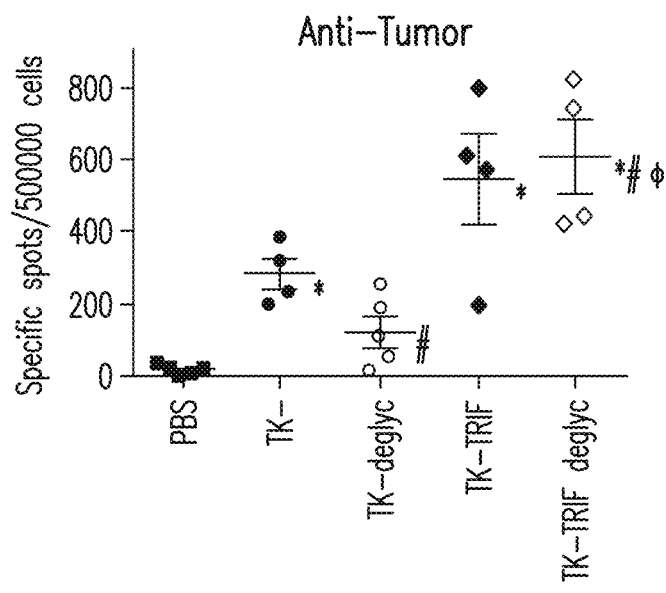

The cellular immune responses to Vaccinia virus and tumor cells were evaluated by IFN-γ ELISpot assay, as described above in section 6.3. At day 7 post-virus administration, spleens were harvested from mice injected intravenously with $1\times10^8$ PFU of indicated viruses or PBS (BALB/c mice bearing Renca xenografts) and evaluated for the amount of CTLs recognizing Vaccinia virus or Renca cells. FIG. 11A shows that deglycosylation and expression of TRIF resulted in a significant increase in CTL production recognizing the Vaccinia virus in vivo, as compared to the modifications alone, e.g., TK-TRIF or TK-deglyc. In particular, the deglycosylated virus expressing TRIF resulted in an increase in CTL production that was greater than the increases in CTL production observed by the individual modifications. Additionally, FIG. 11B shows that deglycosylation and expression of TRIF resulted in an increase in the amount of CTLs production recognizing RENCA cells in vivo, as compared to the modifications alone, e.g., TK-TRIF or TK-deglyc.

Figure 11C:
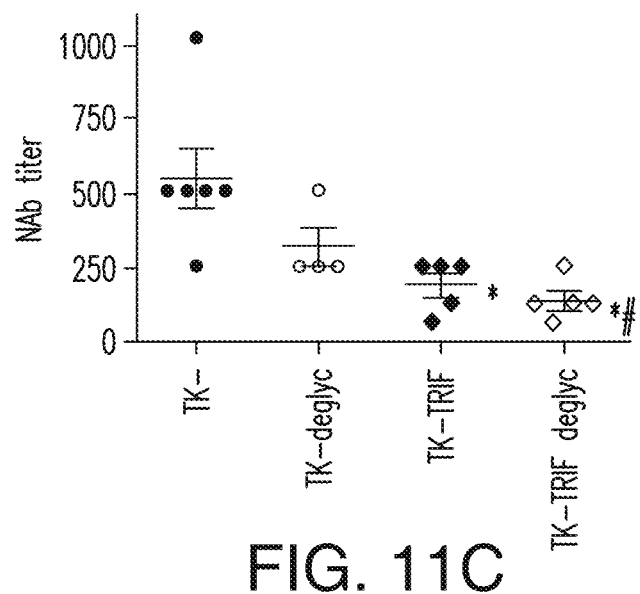

A neutralizing assay was performed to determine circulating anti-Vaccinia antibody levels for mice injected with $1\times10^8$ PFU of TK-, TK-TRIF, or TK-TRIF deglycosylated. Nabs titers were determined by the highest dilution of serum that resulted in at least 50% inhibition of infection. FIG. 11C shows that the amount of neutralizing antibody is greater in wild-type C57BL/6 mice infected with TK-compared to mice infected with TK-TRIF, TK-deglyc or TK-TRIF-deglyc. Mice infected with TK-TRIF-deglyc showed the greatest reduction in the amount of neutralizing antibody in the serum.

Figure 11D:
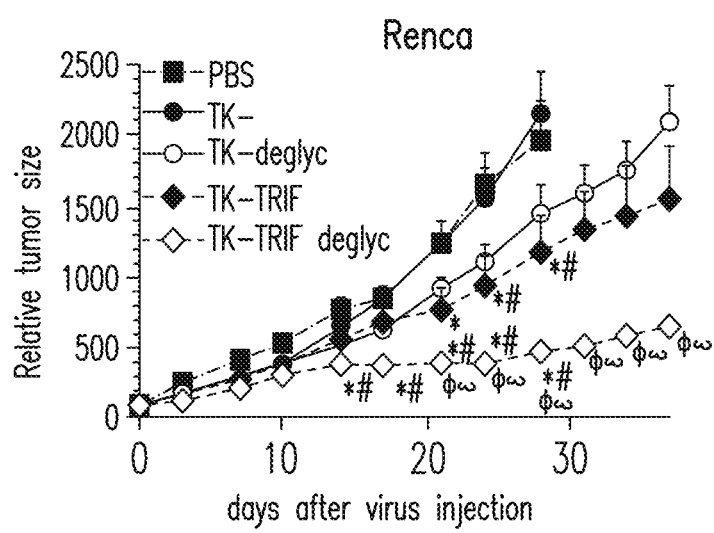
Figure 11E:
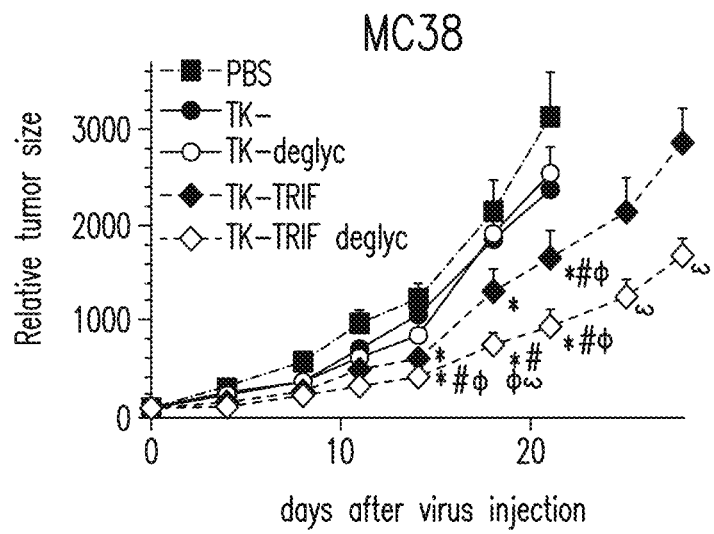
Figure 11F:
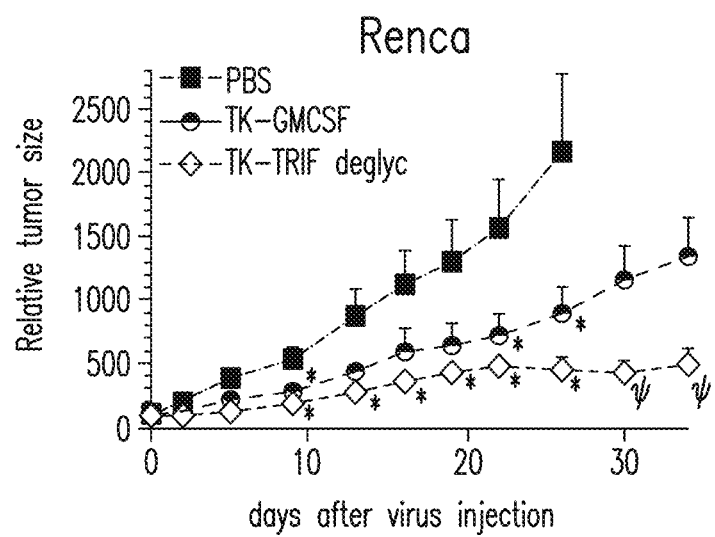

The effect of deglycosylated virus expressing TRIF on tumor growth was analyzed in BALB/c mice bearing Renca or C57BL/6 mice bearing MC38 tumor xenografts. For Renca or MC38 tumor xenografts, tumor cell lines were implanted subcutaneously at 5×10⁵ cells per mouse into BALB/c or C57BL/6 mice, respectively. When tumor reached ~50-100 mm³, mice were treated with a single intratumoral dose of indicated viruses (1×10⁸ PFU/mouse) into the tail vein. Tumor growth was monitored by caliper measurement and was defined by the equation $V(mm^3)=\pi/6 \times W^2 \times L$, where W and L are the width and the length of the tumor, respectively. Data was expressed as relative tumor size to the beginning of the therapy, which was set as 100%. Surprisingly, TK-TRIF deglycosylated virus resulted in a greater reduction in the tumor size of RENCA and MC38 xenograft-bearing mice as compared to the additive effect of the individual modifications combined or the TK-virus (FIGS. 11D and E). Further, TK-TRIF deglycosylated exhibited improved anti-tumor activity compared to TK-GMCSF, as observed by a significant reduction in tumor size in BALB/c mice harboring Renca xenografts (FIG. 11 IF) or 4T1 subcutaneous tumors in BALB/c mice (FIG. 9D). Accordingly, deglycosylated TK-vaccinia virus expressing TRIF exhibits a significantly improved anti-tumor response and results in a reduction in anti-virus antibody production.

10. EXAMPLE 5

Effect of Combined TRIF Expression, De-Sialylation and C12L Deletion in UPCI-1812

The above modifications, namely C12L deletion, de-sialylation, and introduction of TRIF were incorporated together to create new VV strain UPCI-1812, and the effect of this triply modified virus was evaluated for its therapeutic and immunologic effects. As shown in FIG. 12A, UPCI-1812 infection resulted in significantly better survival than WR.TK-encoding GM-CSF. Relative to the de-sialylated virus with the C12L deletion ("vvDD"), UPCI-1812 produced significantly higher levels of interferon gamma (IFN-γ) (FIG. 12B) and interleukin-12 (IL-12) (FIG. 12C).

11. EXAMPLE 6

Effect of PGE2 Targeting

Oncolytic viral therapies have finally begun to demonstrate clinical efficacy in randomized studies highlighting the real potential of the platform. However, among the current generation of clinical vectors, those found to be most successful have expressed an immune activating cytokine (GM-CSF), reinforcing a plethora of pre-clinical data indicating that the immune response is a key mediator of viral effectiveness. However, despite this observation, it is still unclear how or why some patients respond well and others appear resistant to oncolytic virotherapy.

Initial experiments were performed to correlate the in vitro sensitivity of a tumor cell line to viral infection and replication with in vivo responses of the same cell line when used to form syngeneic tumors in immunocompetent mice. 14 different tumor mouse cell lines of different tumor types and mouse strains were analyzed in vitro by infecting the cell lines with TK- (FIG. 26A). Viral production and viral gene expression was observed in the 14 different tumor mouse cell lines. Viral production was analyzed by seeding 2×10⁵ cells in 24-well plates, followed by infection at an MOI of 1 (PFU/cell) with indicated Vaccinia viruses. Four hours after infection, cultures were washed twice with PBS and incubated in fresh virus-free medium. At indicated time points after infection, cultures were harvested and frozen-thawed three times to obtain the cell extract (CE). Viral titers were determined by plaque assay on BSC-1 cells.

Seven of the 14 lines were further tested in vivo using direct intratumoral injection of TK- (FIGS. 13A and B and FIGS. 26A and B). Direct intratumoral injection was used to reduce variability that may occur due to differences in viral delivery. As shown in FIGS. 13A and B, no direct correlation was observed between either viral replication or viral-mediated cell killing and in vivo anti-tumor effect, indicating factors other than direct oncolytic activity mediate anti-tumor effects.

Oncolytic vaccinia expressing luciferase was used during these experiments to allow analysis of viral gene expression over time in individual mice (as a surrogate for viral replication and persistence), and allow comparisons to subsequent response. Two distinct patterns appeared to emerge from the data. For the more resistant tumor models, defined as viral therapy increasing overall survival by less than 2 weeks, as seen with Renca, B16, PAN02 and 4T1, a direct correlation could be drawn within each individual tumor model, such that the level of viral gene expression at 24 h corresponded to the subsequent response (FIG. 13B). Therefore even though in vitro replication does not correlate with in vivo activity when comparing tumor models (presumably due to the influence of factors such as ECM and non-tumor cells in the tumor), within any one individual tumor model there is a correlation between early viral gene expression and subsequent response. Without being bound to a particular theory, it appears that viral replication and direct oncolytic activity is the key mediator of the limited response in the more resistant tumor models. However, a different pattern was observed in tumors that responded well to viral therapy, which includes tumor models AB12, LLC, MC38. In these models, the best responders within each model demonstrated a rapid and robust clearance of the virus after initial infection and early replication (FIG. 13B and FIG. 27). This robust clearance suggests the induction of a strong immune response to enhance the viral direct oncolytic effects in the better responding tumor models.

In order to examine this observation in more detail, two tumor models in the same genetic background were initially chosen that displayed comparable responses after viral treatment in vivo, but one of which (LLC) displayed indications of a robust immune induction (early viral clearance) and limited viral-mediated cell killing in vitro (FIG. 13B and FIGS. 26A and B). The other (B16) was more sensitive to viral killing in vitro, and any response in vivo appeared to correlate with early viral gene expression (FIG. 13B and FIGS. 26A and B). A comprehensive examination of activation of systemic immune markers after viral infection were compared between mice with no tumors, mice with B16 tumors and mice with LLC tumors. These included early innate signaling activation markers such as pS6, pSTAT1, pSTAT3, pSTAT5 in different cell populations (FIG. 13C and FIG. 14A), T-cell proliferation markers such as pS6 and Ki67 (FIG. 14A) and activation markers such as CD44 and CD62L (FIG. 14A), and neutralizing antibody responses (FIG. 14D). Minor differences were seen in the systemic immune response to viral therapy between tumor bearing and non-tumor bearing animals, with the one exception being the phosphorylation of S6 in some myeloid cells early after infection (FIG. 13C). pS6 levels were observed to be reduced in tumor bearing animals, but the reduction in immune activation was most pronounced in the B16 tumor-bearing mice (FIG. 13C and FIG. 14A). This was verified in other tumor models, again confirming that pS6 levels were reduced in the more resistant tumor models (including 4T1 and RENCA), indicating a defect in the dendritic cell (DC) response which may mediate resistance in these mice (FIG. 13C).

As there were little differences observed in the systemic immune response, the effects of more localized immune suppression within the tumor were examined. Different immune cells are associated with a suppressive phenotype, including myeloid-derived suppressor cells (MDSC) and regulatory T-cells (T-regs) (and M2 macs). The level of these different cell types in both the spleen and the tumor of all the tumor models as compared to untreated animals were analyzed. For evaluation of immune populations in tumors, tumors were harvested from mice treated as indicated, and mechanically disaggregated and digested with triple enzyme mixture (Collagenase type IV, DNase type IV, and Hyaluronidase type V (Sigma-Aldrich, St Louis, Mo.)). Four-color cell surface immunostaining analyses were performed using a Gallios Flow Cytometer (Beckman Coulter, Inc., Brea, Calif.). Tumor-disaggregated cells were stained using PE-Cy7 anti-mouse CD3 (BD Biosciences, San Jose, Calif.), FITC anti-mouse CD4, PerCP-Cy5.5 anti-mouse CD8, and PE anti-mouse CD25 (eBioscience, San Diego, Calif.).

The level of MDSCs found in the tumor for different tumor models correlated closely with the resistance or sensitivity of that model to viral therapy (FIGS. 15A and B and FIG. 16). For example, Renca, which exhibits resistance to viral therapy, resulted in tumors with high MDSC levels. FIG. 17A shows the number of MDSC in untreated tumors as a function of increased survival after intravenous treatment with 1e8 PFU of WR.TK- for a number of various tumor model systems. Vaccinia strains display a very poor ability to increase survival in mouse tumor models that display high levels of MDSC at baseline. Cells of each of the tumor model cell lines listed (FIG. 17A) were implanted in syngeneic immunocompetent mice. Mice were then either sacrificed in order to determine the average baseline level of MDSC in the resulting tumors for each model or the mice were treated with WR.TK- (or PBS control)(1e8 PFU given intratumorally) and the increase in life expectancy (for 50% survival) determined after treatment (in days). The graph plots "relative MDSC numbers in tumors at baseline" vs "median increase in survival after WR.TK- treatment (relative to untreated control)". More MDSC at baseline correlated with reduced effectiveness of therapy.

Further changes that occurred in the tumor after viral therapy were examined and it was observed that for multiple tumor models, such as 4T1, RENCA and MC38, the addition of vaccinia therapy resulted in a loss of T-reg, but that MDSC levels were unaffected and continued to increase over time, as they did in the control groups (FIGS. 15A and B and FIGS. 16A and B). Viral therapy reduced levels of T-reg in treated tumors but had no impact on MDSC levels. In the Renca tumor model (implanted subcutaneously in BALB/c mice), relative numbers of T-regs or MDSC in the tumor/mg of tumor were determined at different times before or after WR.TK- treatment (I e8 PFU given intratumorally) (FIGS. 17B and C). It therefore appears that oncolytic vaccinia's inability to target MDSC reduced its therapeutic activity in some tumors where the levels of MDSC are high. In the tumors with low background levels of MDSC (MC38), the viral therapy was also found to enhance the level of CD8+T-cells into the tumor, whereas the more resistant tumor models (4T1) did not display any increase (FIG. 15B).

Analysis of the immunogenic vaccinia strain GM-CSF, which expresses the cytokine colony-stimulating factor (CSF) was performed. GM-CSF has been previously shown to result in more dramatic clinical responses and has also been associated with MDSC proliferation. FIGS. 18 and 19 show that although the more immunogenic vaccinia strains (WR.TK-GMCSF and WR.B18R-IFNβ+) did further enhance some aspects of the immune response in the sensitive tumor models, such as further reducing T-reg and increasing CD8+ T-cell levels, no such advantage was seen in the otherwise resistant tumor models. Without being bound to a particular theory, it appears that the main difference between sensitive and resistant tumors relates to the inability of the virus to induce a robust immunotherapeutic effect in tumors with high levels of MDSC-mediated immune suppression within the tumor microenvironment.

Recent reports have identified COX2-mediated production of the prostaglandin PGE2 as a key determinant of MDSC infiltration and maintenance of MDSC phenotype. Two approaches were used to target this pathway. One approach was through the application of a COX2 inhibitor. The second approach was the expression of the prostaglandin-degrading enzyme HPGD directly from the viral vectors. A nucleic acid encoding hydroxyprostaglandin dehydrogenase 15 (HPGD), a mouse enzyme that degrades PGE2, was introduced into WR.TK- by insertion into the thymidine kinase locus by homologous recombination, and under control of the viral p7.5 promoter ("TK-HPGD" or "WR.TK-.HPGD"). As shown in FIG. 20, HPGD was specifically expressed from TK-HPGD and significantly reduced PGE2 levels in Renca cells infected with TK-HPGD. As shown in FIG. 25, it appears that infection with WR.TK- may alter COX2 expression in the tumors locally at the site of infection, without producing significant levels of COX2 expression overall in the tumor, or the virus may selectively replicate in regions with low COX2 levels. Initial in vitro and in vivo experiments determined that even at toxic levels, the COX2 inhibitors were unable to reduce PGE2 levels to anywhere near the level achieved with HPGD expression (FIG. 20).

Figure 21A:
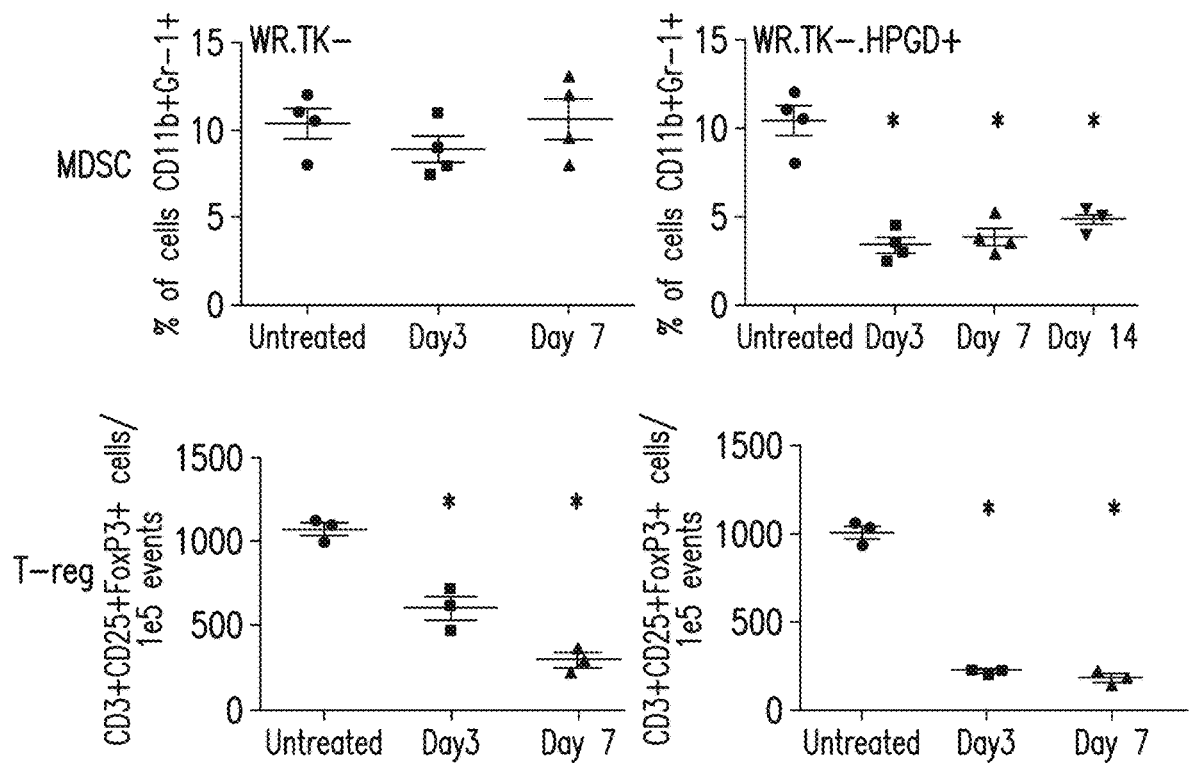
Figure 21B:
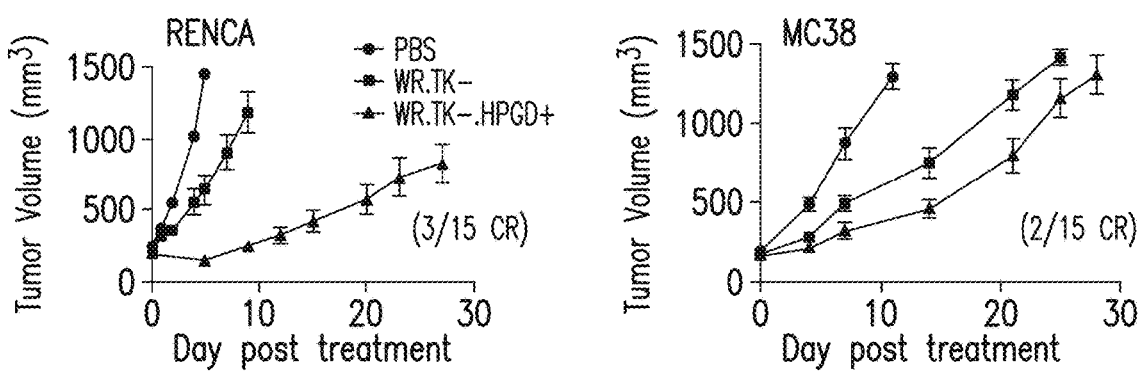
Figure 21C:
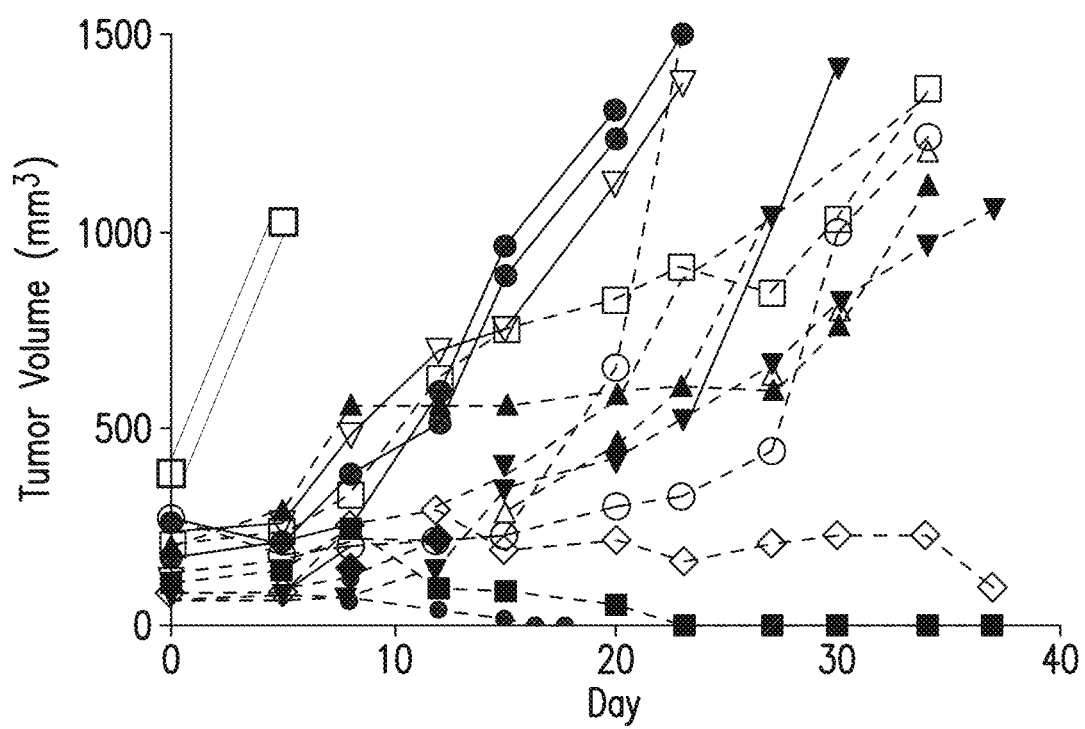

Oncolytic vaccinia expressing HPGD was then tested in several mouse tumor models. It was seen that the number of MDSC cells in the tumor were rapidly and significantly reduced in the spleen and tumors after treatment with WR-TK-HPGD only (FIG. 21 and FIG. 23A-D). Inclusion of HPGD also was found to reduce MDSC in tumor and spleen relative to unmodified WR.TK-virus. This was specific to tumors, with no systemic toxicity seen (FIG. 21A). Interestingly, TK-HPGD also induced a more rapid and robust reduction in T-reg numbers in the tumor. As shown in FIGS. 21B and C, and FIG. 22, infection with WR-TK-HPGD correlated with an enhanced therapeutic effect in several mouse tumor models in vivo and resulted in lower tumor volumes. Of note, the tumor model that was previously most resistant to viral therapy, RENCA, which displayed an "oncolytic only" phenotype and high baseline levels of MDSC, surprisingly displayed the greatest increase in therapeutic benefit after HPGD expression (FIG. 211B).

Figure 21D:
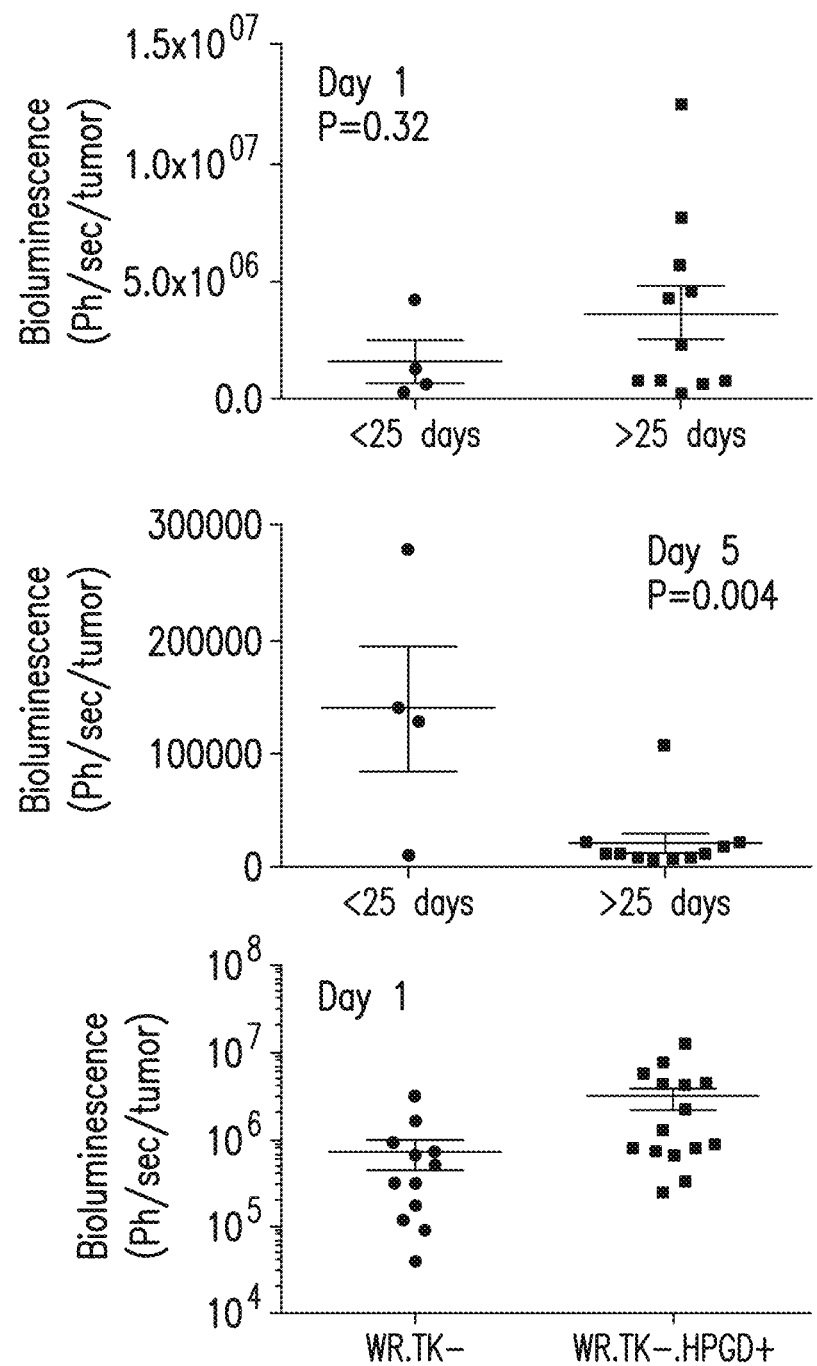

The patterns of viral gene expression were also compared for WR.TK- and WR.TK-HPGD in the RENCA tumor. It was seen that whereas for WR.TK- an "oncolytic only" phenotype was seen (higher gene expression at day 1 correlated with greatest therapeutic benefit), WR.TK-HPGD+ displayed the "oncolytic and immunotherapeutic" phenotype, with the best responders displaying a robust and rapid clearance of the virus by day 5 (FIG. 21D). Without being bound to a particular theory, it appears that HPGD expression is capable of returning the immunotherapeutic activity of the vector in these more resistant models, and so can sensitize otherwise resistant tumors to oncolytic viral therapy. This was despite no overall loss in oncolytic potential of the HPGD expression.

Figure 24D:
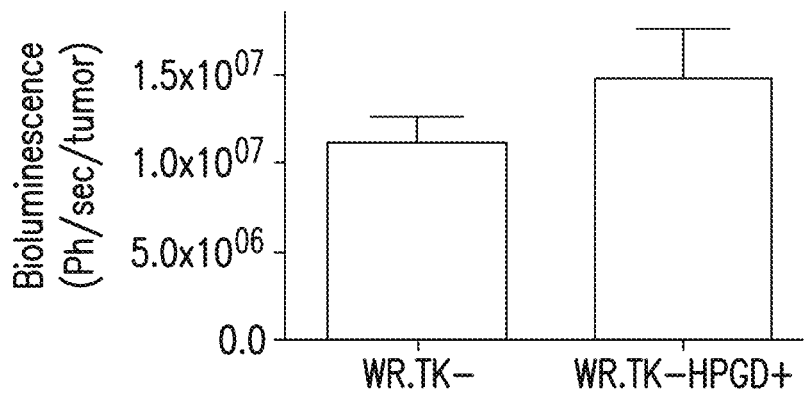
Figure 24D:
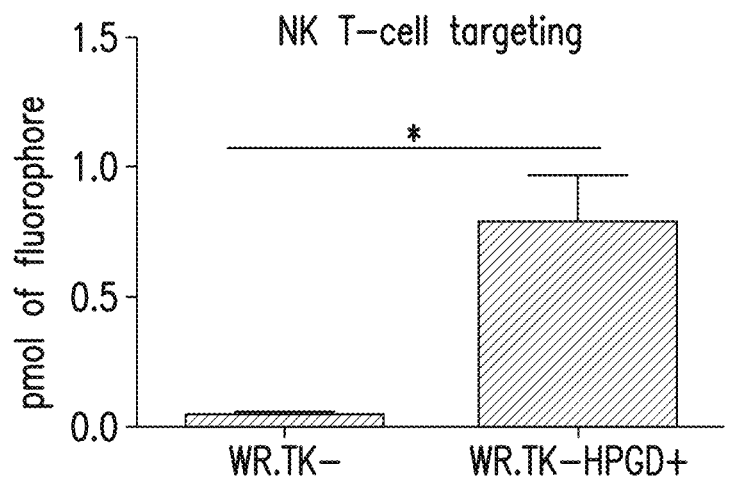
Figure 24D:
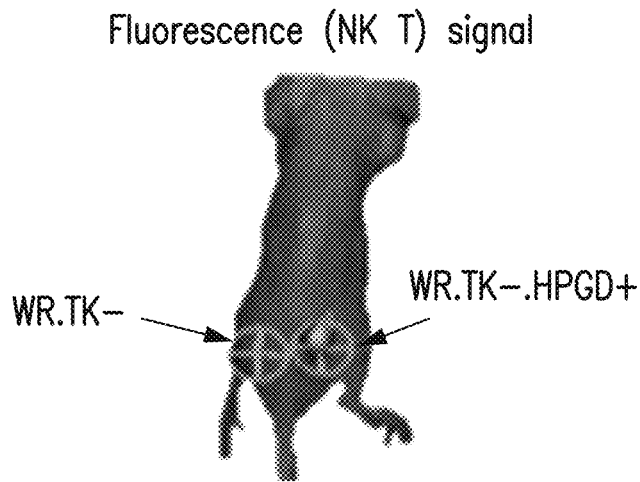

Analysis of the mechanisms mediating the therapeutic advantages seen with WR.TK-HPGD+ were performed. At 3 days after treatment, by which time the levels of MDSC and T-regs had already been dramatically reduced within the tumor environment, it was noted that only modest changes occurred in the levels of cytokines and chemokines in the tumor (FIG. 24A). However, the level of chemokines in the serum changed markedly (FIG. 24B). In particular, chemokines associated with attraction of activated T-cells, including CCL5 were upregulated, while CXCL12 (sdf-1, associated with an immunosuppressive phenotype and poor prognosis) had been dramatically reduced (FIGS. 24A and B). This change in the systemic chemokine effect may be responsible for mediating the changes in the immune cell repertoire in the tumor. This was further examined using a bilateral tumor assay, where one tumor was injected with WR.TK- and the tumor on the opposite flank was injected with WR.TK-HPGD. It was seen that activated T-cells trafficked significantly more to the HPGD expressing tumor (FIG. 24D). Furthermore, at later time points it was seen that WR.TK-HPGD expression resulted in dramatically increased levels of tumor-targeting CTL in the spleen. These data indicates that the expression of HPGD is acting to not only limit the suppressive environment within the tumor, but is also enhancing attraction of T-cells leading to a more robust anti-tumor adaptive immune response. Furthermore, incorporation of HPGD into UPCI-1812 resulted in a virus which inhibited tumor growth significantly more than UPCI-1812 ("combined"; FIG. 28). As shown in FIG. 28, the combined virus resulted in a greater reduction in the tumor growth than the additive effect of the UPCI-1812 virus and VV-HPGD virus. Viral-mediated targeting of PGE2 was capable of overcoming localized immune suppression leading to profound changes in the tumor microenviromnent and resulting in sensitization of previously resistant tumors to viral therapy.

13. EXAMPLE 7

Modification that Increases Activity and Spread

FIG. 29 shows the level of anti-vaccinia neutralizing antibody present in the serum of mice vaccinated with (1e4 PFU) of either WR or WR with an EEV-enhancing point mutation in the A34R viral gene (Lys151 to Glu). The A34R mutant strain produces less anti-vaccinia neutralizing antibody compared to WR-.

14. REFERENCES

1. Guo, Z. S., Thornme, S. H. & Bartlett, D. L. Oncolytic virotherapy: Molecular targets in tumor-selective replication and carrier cell-mediated delivery of oncolytic viruses. Biochim Biophys Acta (2008).
2. Kim, D. H. & Thorne, S. H. Targeted and armed oncolytic poxviruses: a novel multi-mechanistic therapeutic class for cancer. Nat Rev Cancer 9, 64-71 (2009).
3. Kirn, D., Martuza, R. L. & Zwiebel, J. Replication-selective virotherapy for cancer: Biological principles, risk management and future directions. Nat Med 7, 781-7 (2001).
4. Kim, J. H., Oh, J. Y., Park, B. H., Lee, D. E., Kim, J. S., Park, H. E., Roh, M. S., Je, J. E., Yoon, J. H., Thorne, S. H., Kim, D. & Hwang, T. H. Systemic Armed Oncolytic and Immunologic Therapy for Cancer with JX-594, a Targeted Poxvirus Expressing GM-CSF. Mol Ther 14, 361-70 (2006).
5. Kirn, D. H., Wang, Y., Le Boeuf, F., Bell, J. & Thorne, S. H. Targeting of interferon-beta to produce a specific, multi-mechanistic oncolytic vaccinia virus. PLoS Med 4, e353 (2007).
6. Thorne, S. H., Hwang, T. H., O'Gorman, W. E., Bartlett, D. L., Sei, S., Kanji, F., Brown, C., Werier, J., Cho, J. H., Lee, D. E., Wang, Y., Bell, J. & Kirn, D. H. Rational strain selection and engineering creates a broad-spectrum, systemically effective oncolytic poxvirus, JX-963. J Clin Invest 117, 3350-3358 (2007).
7. McCart, J. A., Ward, J. M., Lee, J., Hu, Y., Alexander, H. R., Libutti, S. K., Moss, B. & Bartlett, D. L. Systemic cancer therapy with a tumor-selective vaccinia virus mutant lacking thymidine kinase and vaccinia growth factor genes. Cancer Res 61, 8751-7 (2001).
8. Guo, Z. S., Naik, A., O'Malley, M. E., Popovic, P., Demarco, R., Hu, Y., Yin, X., Yang, S., Zeh, H. J., Moss, B., Lotze, M. T. & Bartlett, D. L. The enhanced tumor selectivity of an oncolytic vaccinia lacking the host range and antiapoptosis genes SPI-1 and SPI-2. Cancer Res 65, 9991-8 (2005).
9. Gnant, M. F., Noll, L. A., Irvine, K. R., Puhlmann, M., Terrill, R. E., Alexander, H. R., Jr. & Bartlett, D. L. Tumor-specific gene delivery using recombinant vaccinia virus in a rabbit model of liver metastases. J Natl Cancer Inst 91, 1744-50 (1999).
10. Zhang, Q., Yu, Y. A., Wang, E., Chen, N., Danner, R. L., Munson, P. J., *Marincola*, F. M. & Szalay, A. A. Eradication of solid human breast tumors in nude mice with an intravenously injected light-emitting oncolytic vaccinia virus. Cancer Res 67, 10038-46 (2007).
11. Yu, Y. A., Shabahang, S., Timiryasova, T. M., Zhang, Q., Beltz, R., Gentschev, I., Goebel, W. & Szalay, A. A. Visualization of tumors and metastases in live animals with bacteria and vaccinia virus encoding light-emitting proteins. Nat Biotechnol 22, 313-20 (2004).
12. Park, B. H., Hwang, T., Liu, T. C., Sze, D. Y., Kim, J. S., Kwon, H. C., Oh, S. Y., Han, S. Y., Yoon, J. H., Hong, S. H., Moon, A., Speth, K., Park, C., Ahn, Y. J., Daneshmand, M., Rhee, B. G., Pinedo, H. M., Bell, J. C. & Kirn, D. H. Use of a targeted oncolytic poxvirus, JX-594, in patients with refractory primary or metastatic liver cancer: a phase I trial. Lancet Oncol 9, 533-42 (2008).
13. Breitbach, C. J., Burke, J., Jonker, D., Stephenson, J., Haas, A. R., Chow, L. Q., Nieva, J., Hwang, T. H., Moon, A., Patt, R., Pelusio, A., Le Boeuf, F., Burns, J., Evgin, L., De Silva, N., Cvancic, S., Robertson, T., Je, J. E., Lee, Y. S., Parato, K., Diallo, J. S., Fenster, A., Daneshmand, M., Bell, J. C. & Kirn, D. H. Intravenous delivery of a multi-mechanistic cancer-targeted oncolytic poxvirus in humans. Nature 477, 99-102 (2011).
14. Schmidt, C. Amgen spikes interest in live virus vaccines for hard-to-treat cancers. Nature biotechnology 29, 295-6 (2011).
15. Coffin, R. Clinical Updates with oncolytic HSV. in 7th International Oncolytic Virus Meeting (Quebec City, 2013).
16. Senzer, N. N., Kaufman, H. L., Amatruda, T., Nemunaitis, M., Reid, T., Daniels, G., Gonzalez, R., Glaspy, J., Whitman, E., Harrington, K., Goldsweig, H., Marshall, T., Love, C., Coffin, R. & Nemunaitis, J. J. Phase 11 clinical trial of a granulocyte-macrophage colony-stimulating fac- 16. ...tor-encoding, second-generation oncolytic herpesvirus in patients with unresectable metastatic melanoma. J Clin Oncol 27, 5763-71 (2009).
17. Bischoff, J. R., Kirn, D. H., Williams, A., Heise, C., Horn, S., Muna, M., Ng, L., Nye, J. A., Sampson-Johannes, A., Fattaey, A. & McCormick, F. An adenovirus mutant that replicates selectively in p53-deficient human tumor cells. Science 274, 373-6 (1996).
18. Khuri, F., Nemunaitis, J., Ganly, I., Gore, M., MacDougal, M., Tannock, I., Kaye, S., Hong, W. & Kim, D. A controlled trial of Onyx-015, an E1B gene-deleted adenovirus, in combination with chemotherapy in patients with recurrent head and neck cancer. Nature Medicine 6, 879-885 (2000).
19. Garber, K. China approves world's first oncolytic virus therapy for cancer treatment. J Natl Cancer Inst 98, 298-300 (2006).
20. Liu, T. C., Hwang, T., Park, B. H., Bell, J. & Kim, D. H. The targeted oncolytic poxvirus JX-594 demonstrates antitumoral, antivascular, and anti-HBV activities in patients with hepatocellular carcinoma. Mol Ther 16, 1637-42 (2008).
21. Kim, M. K., Breitbach, C. J., Moon, A., Heo, J., Lee, Y. K., Cho, M., Lee, J. W., Kim, S. G., Kang, D. H., Bell, J. C., Park, B. H., Kirn, D. H. & Hwang, T. H. Oncolytic and immunotherapeutic vaccinia induces antibody-mediated complement-dependent cancer cell lysis in humans. Science translational medicine 5, 185ra63 (2013).
22. Contag, C. H., Sikorski, R., Negrin, R. S., Schmidt, T., Fan, A. C., Bachireddy, P., Felsher, D. W. & Thorne, S. H. Definition of an enhanced immune cell therapy in mice that can target stem-like lymphoma cells. Cancer Research 70, 9837-45 (2010).
23. Yang, Y., Huang, C. T., Huang, X. & Pardoll, D. M. Persistent Toll-like receptor signals are required for reversal of regulatory T cell-mediated CD8 tolerance. Nature immunology 5, 508-15 (2004).
24. Worschech, A., Chen, N., Yu, Y. A., Zhang, Q., Pos, Z., Weibel, S., Raab, V., Sabatino, M., Monaco, A., Liu, H., Monsurro, V., Buller, R. M., Stroncek, D. F., Wang, E., Szalay, A. A. & Marincola, F. M. Systemic treatment of xenografts with vaccinia virus GLV-1h68 reveals the immunologic facet of oncolytic therapy. BMC genomics 10, 301 (2009).
25. Thorne, S. H., Liang, W., Sampath, P., Schmidt, T., Sikorski, R., Beilhack, A. & Contag, C. H. Targeting localized immune suppression within the tumor through repeat cycles of immune cell-oncolytic virus combination therapy. Molecular therapy: the journal of the American Society of Gene Therapy 18, 1698-705 (2010).
26. Thorne, S. H. Enhancing biological therapy through conditional regulation of protein stability. Expert reviews in molecular medicine 12, e2 (2010).
27. Wang, L. C., Lynn, R. C., Cheng, G., Alexander, E., Kapoor, V., Moon, E. K., Sun, J., Fridlender, Z. G., Isaacs, S. N., Thorne, S. H. & Albelda, S. M. Treating Tumors With a Vaccinia Virus Expressing IFNbeta Illustrates the Complex Relationships Between Oncolytic Ability and Immunogenicity. Molecular therapy: the journal of the American Society of Gene Therapy (2011).
28. Prestwich, R. J., Ilett, E. J., Errington, F., Diaz, R. M., Steele, L. P., Kottke, T., Thompson, J., Galivo, F., Harrington, K. J., Pandha, H. S., Selby, P. J., Vile, R. G. & Melcher, A. A. Immune-mediated antitumor activity of reovirus is required for therapy and is independent of direct viral oncolysis and replication. Clin Cancer Res 15, 4374-81 (2009).
29. Banchereau, J. & Palucka, A. K. Dendritic cells as therapeutic vaccines against cancer. Nat Rev Immunol 5, 296-306 (2005).
30. Nestle, F. O., Tonel, G. & Farkas, A. Cancer vaccines: the next generation of tools to monitor the anticancer immune response. PLoS Med 2, e339 (2005).
31. Rosenberg, S. A., Yang, J. C. & Restifo, N. P. Cancer immunotherapy: moving beyond current vaccines. Nat Med 10, 909-15 (2004).
32. Banaszynski, L. A., Sellmyer, M. A., Contag, C. H., Wandless, T. J. & Thorne, S. H. Chemical control of protein stability and function in living mice. Nat Med (2008).
33. Rommelfanger, D. M., Wongthida, P., Diaz, R. M., Kaluza, K. M., Thompson, J. M., Kottke, T. J. & Vile, R. G. Systemic Combination Virotherapy for Melanoma with Tumor Antigen-Expressing Vesicular Stomatitis Virus and Adoptive T-Cell Transfer. Cancer Research (2012).
34. Thorne, S. H. Immunotherapeutic potential of oncolytic vaccinia virus. Immunologic research 50, 286-93 (2011).
35. Setoguchi, R., Hori, S., Takahashi, T. & Sakaguchi, S. Homeostatic maintenance of natural Foxp3(+) CD25(+) CD4(+) regulatory T cells by interleukin (IL)-2 and induction of autoimmune disease by IL-2 neutralization. The Journal of experimental medicine 201, 723-35 (2005).
36. Enzler, T., Gillessen, S., Manis, J. P., Ferguson, D., Fleming, J., Alt, F. W., Mihm, M. & Dranoff, G. Deficiencies of GM-CSF and interferon gamma link inflammation and cancer. The Journal of experimental medicine 197, 1213-9 (2003).
37. Jinushi, M., Nakazaki, Y., Dougan, M., Carrasco, D. R., Mihm, M. & Dranoff, G. MFG-E8-mediated uptake of apoptotic cells by APCs links the pro- and antiinflammatory activities of GM-CSF. The Journal of clinical investigation 117, 1902-13 (2007).
38. Lemoine, F. M., Cherai, M., Giverne, C., Dimitri, D., Rosenzwajg, M., Trebeden-Negre, H., Chaput, N., Barrou, B., Thioun, N., Gattegnio, B., Selles, F., Six, A., Azar, N., Lotz, J. P., Buzyn, A., Sibony, M., Delcourt, A., Boyer, O., Herson, S., Klatzmann, D. & Lacave, R. Massive expansion of regulatory T-cells following interleukin 2 treatment during a phase I-II dendritic cell-based immunotherapy of metastatic renal cancer. International journal of oncology 35, 569-81 (2009).
39. Wei, S., Kryczek, I., Edwards, R. P., Zou, L., Szeliga, W., Banerjee, M., Cost, M., Cheng, P., Chang, A., Redman, B., Herberman, R. B. & Zou, W. Interleukin-2 administration alters the CD4+FOXP3+T-cell pool and tumor trafficking in patients with ovarian carcinoma. Cancer Research 67, 7487-94 (2007).
40. Filipazzi, P., Valenti, R., Huber, V., Pilla, L., Canese, P., Iero, M., Castelli, C., Mariani, L., Parmiani, G. & Rivoltini, L. Identification of a new subset of myeloid suppressor cells in peripheral blood of melanoma patients with modulation by a granulocyte-macrophage colony-stimulation factor-based antitumor vaccine. Journal of clinical oncology: official journal of the American Society of Clinical Oncology 25, 2546-53 (2007).
41. Smith, G. L., Symons, J. A., Khanna, A., Vanderplasschen, A. & Alcami, A. Vaccinia virus immune evasion. Immunol Rev 159, 137-54 (1997).
42. Smith, G. L., Symons, J. A. & Alcami, A. Immune modulation by proteins secreted from cells infected by vaccinia virus. Arch Virol Suppl 15, 111-29 (1999).

43. Symons, J. A., Alcami, A. & Smith, G. L. Vaccinia virus encodes a soluble type I interferon receptor of novel structure and broad species specificity. Cell 81, 551-60 (1995).
44. Iwasaki, A., Stiernholm, B. J., Chan, A. K., Berinstein, N. L. & Barber, B. H. Enhanced CTL responses mediated by plasmid DNA immunogens encoding costimulatory molecules and cytokines. Journal of Immunology 158, 4591-601 (1997).
45. Gulley, J. L., Arlen, P. M., Tsang, K. Y., Yokokawa, J., Palena, C., Poole, D. J., Remondo, C., Cereda, V., Jones, J. L., Pazdur, M. P., Higgins, J. P., Hodge, J. W., Steinberg, S. M., Kotz, H., Dahut, W. L. & Schlom, J. Pilot study of vaccination with recombinant CEA-MUC-1-TRICOM poxviral-based vaccines in patients with metastatic carcinoma. Clin Cancer Res 14, 3060-9 (2008).
46. Takeshita, F., Tanaka, T., Matsuda, T., Tozuka, M., Kobiyama, K., Saha, S., Matsui, K., Ishii, K. J., Coban, C., Akira, S., Ishii, N., Suzuki, K., Klinman, D. M., Okuda, K. & Sasaki, S. Toll-like receptor adaptor molecules enhance DNA-raised adaptive immune responses against influenza and tumors through activation of innate immunity. Journal of virology 80, 6218-24 (2006).
47. Sasaki, S., Amara, R. R., Yeow, W. S., Pitha, P. M. & Robinson, H. L. Regulation of DNA-raised immune responses by cotransfected interferon regulatory factors. Journal of virology 76, 6652-9 (2002).
48. O'Gorman, W. E., Sampath, P., Simonds, E. F., Sikorski, R., O'Malley, M., Krutzik, P. O., Chen, H., Panchanathan, V., Chaudhri, G., Karupiah, G., Lewis, D. B., Thorne, S. H. & Nolan, G. P. Alternate mechanisms of initial pattern recognition drive differential immune responses to related poxviruses. Cell host & microbe 8, 174-85 (2010).
49. Zhu, J., Martinez, J., Huang, X. & Yang, Y. Innate immunity against vaccinia virus is mediated by TLR2 and requires TLR-independent production of IFN-beta. Blood 109, 619-25 (2007).
50. Samuelsson, C., Hausmann, J., Lauterbach, H., Schmidt, M., Akira, S., Wagner, H., Chaplin, P., Suter, M., O'Keeffe, M. & Hochrein, H. Survival of lethal poxvirus infection in mice depends on TLR9, and therapeutic vaccination provides protection. J Clin Invest 118, 1776-84 (2008).
51. Hennessy, E. J., Parker, A. E. & O'Neill, L. A. Targeting Toll-like receptors: emerging therapeutics? Nature reviews. Drug discovery 9, 293-307 (2010).
52. O'Neill, L. A., Bryant, C. E. & Doyle, S. L. Therapeutic targeting of Toll-like receptors for infectious and inflammatory diseases and cancer. Pharmacological reviews 61, 177-97 (2009).
53. Fukata, M. & Abreu, M. T. Role of Toll-like receptors in gastrointestinal malignancies. Oncogene 27, 234-43 (2008).
54. Chen, R., Alvero, A. B., Silasi, D. A., Steffensen, K. D. & Mor, G. Cancers take their Toll—the function and regulation of Toll-like receptors in cancer cells. Oncogene 27, 225-33 (2008).
55. Sautes-Fridman, C., Cherfils-Vicini, J., Damotte, D., Fisson, S., Fridman, W. H., Cremer, I. & Dieu-Nosjean, M. C. Tumor microenvironment is multifaceted. Cancer metastasis reviews 30, 13-25 (2011).
56. Rakoff-Nahoum, S. & Medzhitov, R. Toll-like receptors and cancer. Nature reviews. Cancer 9, 57-63 (2009).
57. Umemura, N., Zhu, J., Mburu, Y. K., Forero, A., Hsieh, P. N., Muthuswamy, R., Kalinski, P., Ferris, R. L. & Sarkar, S. N. Defective NF-kappaB signaling in metastatic head and neck cancer cells leads to enhanced apoptosis by double-stranded RNA. Cancer Research 72, 45-55 (2012).
58. Cheng, Y. S. & Xu, F. Anticancer function of polyinosinic-polycytidylic acid. Cancer biology & therapy 10, 1219-23 (2011).
59. Longhi, M. P., Trumpfheller, C., Idoyaga, J., Caskey, M., Matos, I., Kluger, C., Salazar, A. M., Colonna, M. & Steinman, R. M. Dendritic cells require a systemic type I interferon response to mature and induce CD4+Th1 immunity with poly IC as adjuvant. The Journal of experimental medicine 206, 1589-602 (2009).
60. Trumpfheller, C., Caskey, M., Nchinda, G., Longhi, M. P., Mizenina, O., Huang, Y., Schlesinger, S. J., Colonna, M. & Steinman, R. M. The microbial mimic poly IC induces durable and protective CD4+T cell immunity together with a dendritic cell targeted vaccine. Proceedings of the National Academy of Sciences of the United States of America 105, 2574-9 (2008).
61. Kalinski, P., Hilkens, C. M., Wierenga, E. A. & Kapsenberg, M. L. T-cell priming by type-1 and type-2 polarized dendritic cells: the concept of a third signal. Immunol Today 20, 561-7 (1999).
62. Mailliard, R. B., Wankowicz-Kalinska, A., Cai, Q., Wesa, A., Hilkens, C. M., Kapsenberg, M. L., Kirkwood, J. M., Storkus, W. J. & Kalinski, P. alpha-type-1 polarized dendritic cells: a novel immunization tool with optimized CTL-inducing activity. Cancer Res 64, 5934-7 (2004).
63. Wesa, A., Kalinski, P., Kirkwood, J. M., Tatsumi, T. & Storkus, W. J. Polarized type-1 dendritic cells (DC1) producing high levels of IL-12 family members rescue patient TH1-type antimelanoma CD4+T cell responses in vitro. J Immunother 30, 75-82 (2007).
64. Kalinski, P. & Okada, H. Polarized dendritic cells as cancer vaccines: directing effector-type T cells to tumors. Seminars in immunology 22, 173-82 (2010).
65. Okada, H., Kalinski, P., Ueda, R., Hoji, A., Kohanbash, G., Donegan, T. E., Mintz, A. H., Engh, J. A., Bartlett, D. L., Brown, C. K., Zeh, H., Holtzman, M. P., Reinhart, T. A., Whiteside, T. L., Butterfield, L. H., Hamilton, R. L., Potter, D. M., Pollack, I. F., Salazar, A. M. & Lieberman, F. S. Induction of CD8+T-cell responses against novel glioma-associated antigen peptides and clinical activity by vaccinations with {alpha}-type 1 polarized dendritic cells and polyinosinic-polycytidylic acid stabilized by lysine and carboxymethylcellulose in patients with recurrent malignant glioma. Journal of clinical oncology: official journal of the American Society of Clinical Oncology 29, 330-6 (2011).
66. Hokey, D. A., Larregina, A. T., Erdos, G., Watkins, S. C. & Falo, L. D., Jr. Tumor cell loaded type-1 polarized dendritic cells induce Th1-mediated tumor immunity. Cancer Research 65, 10059-67 (2005).
67. Buller, R. M. & Palumbo, G. J. Poxvirus pathogenesis. Microbiol Rev 55, 80-122 (1991).
68. Moss, B. Poxviridae: The viruses and their replication. in Field's Virology (eds. D. M., K., Fields, B. N. & Howley, P. M.) Ch. 84 (Lippincott-Raven, Philadelphia, 2001).
69. Putz, M. M., Midgley, C. M., Law, M. & Smith, G. L. Quantification of antibody responses against multiple antigens of the two infectious forms of Vaccinia virus provides a benchmark for smallpox vaccination. Nat Med 12, 1310-5 (2006).
70. Symons, J. A., Adams, E., Tscharke, D. C., Reading, P. C., Waldmann, H. & Smith, G. L. The vaccinia virus 70. C12L protein inhibits mouse IL-18 and promotes virus virulence in the murine intranasal model. J Gen Virol 83, 2833-44 (2002).
71. Reading, P. C. & Smith, G. L. Vaccinia virus interleukin-18-binding protein promotes virulence by reducing gamma interferon production and natural killer and T-cell activity. J Virol 77, 9960-8 (2003).
72. Zhu, J., Smith, K., Hsieh, P. N., Mburu, Y. K., Chattopadhyay, S., Sen, G. C. & Sarkar, S. N. High-throughput screening for TLR3-IFN regulatory factor 3 signaling pathway modulators identifies several antipsychotic drugs as TLR inhibitors. Journal of Immunology 184, 5768-76 (2010).
73. Okamura, H., Tsutsi, H., Komatsu, T., Yutsudo, M., Hakura, A., Tanimoto, T., Torigoe, K., Okura, T., Nukada, Y., Hattori, K. & et al. Cloning of a new cytokine that induces IFN-gamma production by T cells. Nature 378, 88-91 (1995).
74. Wong, J. L., Mailliard, R. B., Moschos, S. J., Edington, H., Lotze, M. T., Kirkwood, J. M. & Kalinski, P. Helper Activity of Natural Killer Cells During the Dendritic Cell-mediated Induction of Melanoma-specific Cytotoxic T Cells. Journal of immunotherapy 34, 270-8 (2011).
75. Falivene, J., Del Medico Zajac, M. P., Pascutti, M. F., Rodriguez, A. M., Maeto, C., Perdiguero, B., Gomez, C. E., Esteban, M., Calamante, G. & Gherardi, M. M. Improving the MVA vaccine potential by deleting the viral gene coding for the IL-18 binding protein. PLoS One 7, e32220 (2012).
76. Kim, D. H., Wang, Y., Liang, W., Contag, C. H. & Thorne, S. H. Enhancing poxvirus oncolytic effects through increased spread and immune evasion. Cancer Res 68, 2071-5 (2008).
77. Puhlmann, M., Brown, C. K., Gnant, M., Huang, J., Libutti, S. K., Alexander, H. R. & Bartlett, D. L. Vaccinia as a vector for tumor-directed gene therapy: biodistribution of a thymidine kinase-deleted mutant. Cancer Gene Ther 7, 66-73 (2000).
78. Alvarez-Breckenridge, C. A., Yu, J., Price, R., Wojton, J., Pradarelli, J., Mao, H., Wei, M., Wang, Y., He, S., Hardcastle, J., Fernandez, S. A., Kaur, B., Lawler, S. E., Vivier, E., Mandelboim, O., Moretta, A., Caligiuri, M. A. & Chiocca, E. A. NK cells impede glioblastoma virotherapy through NKp30 and NKp46 natural cytotoxicity receptors. Nature Medicine 18, 1827-34 (2012).
79. Errington, F., Jones, J., Merrick, A., Bateman, A., Harrington, K., Gough, M., O'Donnell, D., Selby, P., Vile, R. & Melcher, A. Fusogenic membrane glycoprotein-mediated tumour cell fusion activates human dendritic cells for enhanced IL-12 production and T-cell priming. Gene Ther 13, 138-49 (2006).
80. Prestwich, R. J., Errington, F., Ilett, E. J., Morgan, R. S., Scott, K. J., Kottke, T., Thompson, J., Morrison, E. E., Harrington, K. J., Pandha, H. S., Selby, P. J., Vile, R. G. & Melcher, A. A. Tumor infection by oncolytic reovirus primes adaptive antitumor immunity. Clinical cancer research: an official journal of the American Association for Cancer Research 14, 7358-66 (2008).
81. Feoktistova, M., Geserick, P., Kellert, B., Dimitrova, D. P., Langlais, C., Hupe, M., Cain, K., MacFarlane, M., Hacker, G. & Leverkus, M. cIAPs block Ripoptosome formation, a RIP1/caspase-8 containing intracellular cell death complex differentially regulated by cFLIP isoforms. Molecular cell 43, 449-63 (2011).
82. Sato, S., Sugiyama, M., Yamamoto, M., Watanabe, Y., Kawai, T., Takeda, K. & Akira, S. Toll/IL-1 receptor domain-containing adaptor inducing IFN-beta (TRIF) associates with TNF receptor-associated factor 6 and TANK-binding kinase 1, and activates two distinct transcription factors, NF-kappa B and IFN-regulatory factor-3, in the Toll-like receptor signaling. Journal of Immunology 171, 4304-10 (2003).
83. Jiang, Z., Mak, T. W., Sen, G. & Li, X. Toll-like receptor 3-mediated activation of NF-kappaB and IRF3 diverges at Toll-IL-1 receptor domain-containing adapter inducing IFN-beta. Proceedings of the National Academy of Sciences of the United States of America 101, 3533-8 (2004).
84. Bahar, M. W., Kenyon, J. C., Putz, M. M., Abrescia, N. G., Pease, J. E., Wise, E. L., Stuart, D. I., Smith, G. L. & Grimes, J. M. Structure and function of A41, a vaccinia virus chemokine binding protein. PLoS Pathog 4, e5 (2008).
85. Smith, G. L. & Moss, B. Infectious poxvirus vectors have capacity for at least 25 000 base pairs of foreign DNA. Gene 25, 21-8 (1983).
86. Jones, S. A., Scheller, J. & Rose-John, S. Therapeutic strategies for the clinical blockade of IL-6/gp130 signaling. The Journal of clinical investigation 121, 3375-83 (2011).
87. Chang, C. L., Ma, B., Pang, X., Wu, T. C. & Hung, C. F. Treatment with cyclooxygenase-2 inhibitors enables repeated administration of vaccinia virus for control of ovarian cancer. Molecular therapy: the journal of the American Society of Gene Therapy 17, 1365-72 (2009).
88. Bernard, M. P., Bancos, S., Chapman, T. J., Ryan, E. P., Treanor, J. J., Rose, R. C., Topham, D. J. & Phipps, R. P. Chronic inhibition of cyclooxygenase-2 attenuates antibody responses against vaccinia infection. Vaccine 28, 1363-72 (2010).
89. Kalinski, P. Regulation of immune responses by prostaglandin E2. Journal of Immunology 188, 21-8 (2012).
90. Vella, L. A., Yu, M., Fuhrmann, S. R., El-Amine, M., Epperson, D. E. & Finn, O. J. Healthy individuals have T-cell and antibody responses to the tumor antigen cyclin B I that when elicited in mice protect from cancer. Proceedings of the National Academy of Sciences of the United States of America 106, 14010-5 (2009).
91. Weiss, V. L., Lee, T. H., Song, H., Kouo, T. S., Black, C. M., Sgouros, G., Jaffee, E. M. & Armstrong, T. D. Trafficking of high avidity HER-2/neu-specific T cells into HER-2/neu-expressing tumors after depletion of effector/memory-like regulatory T cells. PLoS One 7, e31962 (2012).
92. Ercolini, A. M., Ladle, B. H., Manning, E. A., Pfannenstiel, L. W., Armstrong, T. D., Machiels, J. P., Bieler, J. G., Emens, L. A., Reilly, R. T. & Jaffee, E. M. Recruitment of latent pools of high-avidity CD8(+) T cells to the antitumor immune response. The Journal of experimental medicine 201, 1591-602 (2005).
93. Pulido, J., Kottke, T., Thompson, J., Galivo, F., Wongthida, P., Diaz, R. M., Rommelfanger, D., Ilett, E., Pease, L., Pandha, H., Harrington, K., Selby, P., Melcher, A. & Vile, R. Using virally expressed melanoma cDNA libraries to identify tumor-associated antigens that cure melanoma. Nature biotechnology 30, 337-43 (2012).
94. Pol, J. G., Acuna, S., Stephenson, K., Tang, N., Kazdhan, N., Bramson, J. L., McCart, J. A., Stojdl, D., Bell, J., Wan, Y. & Lichty, B. Preclinical Evaluation of an Oncolytic Maraba Virus Vaccine in a Simian Model. in 7th International Oncolytic Viruses Meeting (Quebec City, 2013).
95. Belyakov, I. M. & Ahlers, J. D. What role does the route of immunization play in the generation of protective immunity against mucosal pathogens? Journal of Immunology 183, 6883-92 (2009).

96. Guy, C. T., Webster, M. A., Schaller, M., Parsons, T. J., Cardiff, R. D. & Muller, W. J. Expression of the neu protooncogene in the mammary epithelium of transgenic mice induces metastatic disease. Proceedings of the National Academy of Sciences of the United States of America 89, 10578-82 (1992).

97. Tsukamoto, A. S., Grosschedl, R., Guzman, R. C., Parslow, T. & Varmus, H. E. Expression of the int-1 gene in transgenic mice is associated with mammary gland hyperplasia and adenocarcinomas in male and female mice. Cell 55, 619-25 (1988).

98. Kelly, K. J., Brader, P., Woo, Y., Li, S., Chen, N., Yu, Y. A., Szalay, A. A. & Fong, Y. Real-time intraoperative detection of melanoma lymph node metastases using recombinant vaccinia virus GLV-1h68 in an immunocompetent animal model. International journal of cancer. Journal international du cancer 124, 911-8 (2009).

99. Eisenberg, D. P., Adusumilli, P. S., Hendershott, K. J., Chung, S., Yu, Z., Chan, M. K., Hezel, M., Wong, R. J. & Fong, Y. Real-time intraoperative detection of breast cancer axillary lymph node metastases using a green fluorescent protein-expressing herpes virus. Annals of surgery 243, 824-30; discussion 830-2 (2006).

100. Brader, P., Kelly, K., Gang, S., Shah, J. P., Wong, R. J., Hricak, H., Blasberg, R. G., Fong, Y. & Gil, Z. Imaging of lymph node micrometastases using an oncolytic herpes virus and [F]FEAU PET. PLoS One 4, e4789 (2009).

101. Kim, P. S., Armstrong, T. D., Song, H., Wolpoe, M. E., Weiss, V., Manning, E. A., Huang, L. Q., Murata, S., Sgouros, G., Emens, L. A., Reilly, R. T. & Jaffee, E. M. Antibody association with HER-2/neu-targeted vaccine enhances CD8 T cell responses in mice through Fe-mediated activation of DCs. The Journal of clinical investigation 118, 1700-11 (2008).

102. Le, D. T., Ladle, B. H., Lee, T., Weiss, V., Yao, X., Leubner, A., Armstrong, T. D. & Jaffee, E. M. CD8(+) Foxp3(+) tumor infiltrating lymphocytes accumulate in the context of an effective anti-tumor response. International journal of cancer. Journal international du cancer 129, 636-47 (2011).

103. Chen, H., Sampath, P., Hou, W. & Thorne, S. H. Regulating cytokine function enhances safety and activity of genetic cancer therapies. Molecular therapy: the journal of the American Society of Gene Therapy 21, 167-74 (2013).

104. Green, D. R., Ferguson, T., Zitvogel, L. & Kroemer, G. Immunogenic and tolerogenic cell death. Nature reviews. Immunology 9, 353-63 (2009).

105. Workenhe, S. T., Pol, J. G., Lichty, B. D., Cummings, D. T. & Mossman, K. L. Mitoxantrone synergizes with oncolytic herpes simplex virus to regress established breast tumors in part by increasing recruitment of CD8+T cells. in 7th International Oncolytic Viruses Meeting (Quebec City, 2013).

106. Fujita, M., Kohanbash, G., Fellows-Mayle, W., Hamilton, R. L., Komohara, Y., Decker, S. A., Ohifest, J. R. & Okada, H. COX-2 blockade suppresses gliomagenesis by inhibiting myeloid-derived suppressor cells. Cancer Research 71, 2664-74 (2011).

107. Godin-Ethier, J., Hanafi, L. A., Piccirillo, C. A. & Lapointe, R. Indoleamine 2,3-dioxygenase expression in human cancers: clinical and immunologic perspectives. Clinical cancer research: an official journal of the American Association for Cancer Research 17, 6985-91 (2011).

108. Terajima, M. & Leporati, A. M. Role of Indoleamine 2,3-Dioxygenase in Antiviral Activity of Interferon-gamma Against Vaccinia Virus. Viral immunology 18, 722-9 (2005).

109. Galon, J., Costes, A., Sanchez-Cabo, F., Kirilovsky, A., Mlecnik, B., Lagorce-Pages, C., Tosolini, M., Camus, M., Berger, A., Wind, P., Zinzindohoue, F., Bruneval, P., Cugnenc, P. H., Trajanoski, Z., Fridman, W. H. & Pages, F. Type, density, and location of immune cells within human colorectal tumors predict clinical outcome. Science 313, 1960-4 (2006).

110. Parato, K. A., Breitbach, C. J., Le Boeuf, F., Wang, J., Storbeck, C., Ilkow, C., Diallo, J. S., Falls, T., Burns, J., Garcia, V., Kanji, F., Evgin, L., Hu, K., Paradis, F., Knowles, S., Hwang, T. H., Vanderhyden, B. C., Auer, R., Kim, D. H. & Bell, J. C. The oncolytic poxvirus JX-594 selectively replicates in and destroys cancer cells driven by genetic pathways commonly activated in cancers. Molecular therapy: the journal of the American Society of Gene Therapy 20, 749-58 (2012).

111. Visus, C., Wang, Y., Lozano-Leon, A., Ferris, R. L., Silver, S., Szczepanski, M. J., Brand, R. E., Ferrone, C. R., Whiteside, T. L., Ferrone, S., DeLeo, A. B. & Wang, X. Targeting ALDH(bright) human carcinoma-initiating cells with ALDH1A1-specific CD8(+) T cells. Clinical cancer research: an official journal of the American Association for Cancer Research 17, 6174-84 (2011).

112. Silva, I. A., Bai, S., McLean, K., Yang, K., Griffith, K., Thomas, D., Ginestier, C., Johnston, C., Kueck, A., Reynolds, R. K., Wicha, M. S. & Buckanovich, R. J. Aldehyde dehydrogenase in combination with CD133 defines angiogenic ovarian cancer stem cells that portend poor patient survival. Cancer Research 71, 3991-4001 (2011).

113. Charafe-Jauffret, E., Ginestier, C., Iovino, F., Wicinski, J., Cervera, N., Finetti, P., Hur, M. H., Diebel, M. E., Monville, F., Dutcher, J., Brown, M., Viens, P., Xerri, L., Bertucci, F., Stassi, G., Dontu, G., Bimbaum, D. & Wicha, M. S. Breast cancer cell lines contain functional cancer stem cells with metastatic capacity and a distinct molecular signature. Cancer Research 69, 1302-13 (2009).

114. Ning, N., Pan, Q., Zheng, F., Teitz-Tennenbaum, S., Egenti, M., Yet, J., Li, M., Ginestier, C., Wicha, M. S., Moyer, J. S., Prince, M. E., Xu, Y., Zhang, X. L., Huang, S., Chang, A. E. & Li, Q. Cancer stem cell vaccination confers significant antitumor immunity. Cancer Research 72, 1853-64 (2012).

115. Cho, R. W., Wang, X., Diehn, M., Shedden, K., Chen, G. Y., Sherlock, G., Gurney, A., Lewicki, J. & Clarke, M. F. Isolation and molecular characterization of cancer stem cells in MMTV-Wnt-1 murine breast tumors. Stem Cells 26, 364-71 (2008).

116. Ginestier, C., Liu, S., Diebel, M. E., Korkaya, H., Luo, M., Brown, M., Wicinski, J., Cabaud, O., Charafe-Jauffret, E., Bimbaum, D., Guan, J. L., Dontu, G. & Wicha, M. S. CXCR1 blockade selectively targets human breast cancer stem cells in vitro and in xenografts. The Journal of clinical investigation 120, 485-97 (2010).

Various publications are cited herein, the contents of which are hereby incorporated by reference in their entireties.

What is claimed is:

1. An oncolytic vaccinia virus comprising a nucleic acid encoding a Toll/IL-1R domain-containing adapter inducing interferon beta (TRIF) protein or a functional domain thereof, wherein the oncolytic virus is thymidine kinase negative.

2. The oncolytic vaccinia virus of claim 1, further comprising a nucleic acid encoding 15-PGDH or a functional domain thereof.

3. The oncolytic vaccinia virus of claim 1, further comprising an envelope with reduced glycosylation relative to an otherwise identical unmodified virus.

4. The oncolytic vaccinia virus of claim 1, further comprising a C12L deletion.

5. The oncolytic vaccinia virus of claim 1, further comprising a deletion selected from the group consisting of a B8R deletion, a B18R deletion, an A35R deletion, a deletion or functional deletion of interleukin 18-binding protein and a combination thereof.

6. The oncolytic vaccinia virus of claim 1, further comprising a mutation or deletion selected from the group consisting of a A34R Lys151 to Glu mutation, a complete or partial deletion of B5R, a mutation or deletion of A36R, a mutation or deletion of A56R and a combination thereof.

7. The oncolytic vaccinia virus of claim 1, further comprising a nucleic acid encoding granulocyte macrophage colony stimulating factor.

8. The oncolytic vaccinia virus of claim 1, wherein thymidine kinase negative comprises a deletion of thymidine kinase gene.

9. The oncolytic vaccinia virus of claim 2, further comprising a C12L deletion.

10. The oncolytic vaccinia virus of claim 2, further comprising an envelope with reduced glycosylation relative to an otherwise identical unmodified virus.

11. The oncolytic vaccinia virus of claim 4, further comprising an envelope with reduced glycosylation relative to an otherwise identical unmodified virus.

12. The oncolytic vaccinia virus of claim 9, further comprising an envelope with reduced glycosylation relative to an otherwise identical unmodified virus.

13. A composition comprising the oncolytic vaccinia virus of claim 1 and an immunomodulatory agent, an anti-cancer agent, an agent that inhibits or reduces the level of myeloid derived suppressor cells or any combination thereof.

14. The composition of claim 13, wherein the immunomodulatory agent is selected from the group consisting of: an anti-CD33 antibody or a fragment thereof, an anti-CD11b antibody or a fragment thereof, a COX2 inhibitor, an immune checkpoint inhibitor, an agent capable of suppressing antiviral immunity and a combination thereof.

15. A method of reducing the growth of a cancer cell comprising administering, to the cancer cell, an effective amount of the oncolytic vaccinia virus of claim 1.

16. A method of reducing the growth of a tumor comprising administering, to the tumor, an effective amount of the oncolytic vaccinia virus of claim 1.

17. A method of treating a subject having cancer comprising administering, to the subject, an effective amount of the oncolytic vaccinia virus of claim 1.

18. The method of claim 17, further comprising administering an agent selected from the group consisting of an anti-cancer agent, an immunomodulatory agent, and a combination thereof.

19. A modified oncolytic vaccinia virus comprising an envelope with reduced sialylation relative to an otherwise identical unmodified virus, and a nucleic acid encoding a Toll/IL-1R domain-containing adapter inducing interferon beta (TRIF) protein or a functional domain thereof, wherein the modified oncolytic vaccinia virus is thymidine kinase negative.

20. The modified oncolytic vaccinia virus of claim 19, further comprising a nucleic acid encoding 15-PGDH or a functional domain thereof.

21. The modified oncolytic vaccinia virus of claim 20, further comprising a C12L deletion.

22. A composition comprising the oncolytic vaccinia virus of claim 19 and an immunomodulatory agent, an anti-cancer agent, an agent that inhibits or reduces the level of myeloid derived suppressor cells or any combination thereof.

23. The composition of claim 22, wherein the immunomodulatory agent is selected from the group consisting of: an anti-CD33 antibody or a fragment thereof, an anti-CD11b antibody or a fragment thereof, a COX2 inhibitor, and an immune checkpoint inhibitor, an agent capable of suppressing antiviral immunity and a combination thereof.

24. An oncolytic vaccinia virus comprising a nucleic acid encoding a Toll/IL-1R domain-containing adapter inducing interferon beta (TRIF) protein or a functional domain thereof and one or more of the following modifications:
(i) a viral backbone mutation;
(ii) a modification of viral glycosylation;
(iii) a modification that promotes T cell response;
(iv) a modification that inhibits immunosuppression; and
(v) modification that enhances virus spread and activity,
wherein the oncolytic vaccinia virus is thymidine kinase negative.

* * * * *